United States Patent

Fukunishi et al.

Patent Number: 6,114,325
Date of Patent: Sep. 5, 2000

[54] 1,2-DI-SUBSTITUTED BENZENE-CARBOXAMIDE DERIVATIVE, HAIR GROWTH PROMOTER AND EXTERNAL COMPOSITION FOR SKIN USING THE SAME

[75] Inventors: Hirotada Fukunishi; Kenichi Umishio; Masahiro Tajima; Koji Kobayashi, all of Kanagawa, Japan

[73] Assignee: Shiseido Co., Ltd., Tokyo, Japan

[21] Appl. No.: 09/176,947

[22] Filed: Oct. 22, 1998

[30] Foreign Application Priority Data

Oct. 23, 1997 [JP] Japan ................. 9-309335

[51] Int. Cl.[7] ............. A61K 31/495; A61K 31/5513; C07D 241/04; C07D 243/08
[52] U.S. Cl. .............. 514/218; 514/237.8; 514/255.01; 514/331; 514/399; 514/487; 514/489; 514/522; 514/620; 514/622; 540/575; 544/122; 544/169; 544/382; 544/389; 544/390; 544/400; 546/233; 548/338.1; 560/27; 560/32; 560/159; 560/163; 564/164; 564/165; 564/176
[58] Field of Search ............. 540/575; 544/169, 544/382, 389, 390, 400, 112; 546/233; 548/338.1; 560/27, 32, 159, 163; 564/164, 165, 176; 514/218, 237.8, 255, 331, 399, 487, 489, 522, 620, 622, 255.01

[56] References Cited

U.S. PATENT DOCUMENTS 5,872,115  2/1999  Binet et al. ............. 514/211

FOREIGN PATENT DOCUMENTS

| 0 627 410 A1 | 12/1994 | European Pat. Off. . |
|---|---|---|
| 07304736 | 11/1995 | Japan . |
| 07316022 | 12/1995 | Japan . |
| 07316023 | 12/1995 | Japan . |
| 08020521 | 1/1996 | Japan . |
| 08026942 | 1/1996 | Japan . |
| 96/34856 | 7/1998 | WIPO . |

*Primary Examiner*—Richard L. Raymond
*Attorney, Agent, or Firm*—Snider & Associates; Ronald R. Snider

[57] ABSTRACT

A 1,2-di-substituted benzene-carboxamide derivative or a salt thereof expressed by the following Formula (I);

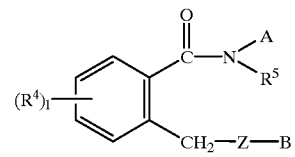

(I)

wherein each of A and B is $R^1$ or $-(CH_2)n-NR^2R^3$, wherein when A is $R^1$, B is $-(CH_2)n-NR^2R^3$ and when A is $-(CH_2)n-NR^2R^3$, B is $R^1$; Z is $-O-$, $-OCO-$, $-OCONR^6-$ or $-NR^6-$; $R^1$ is a hydrocarbon group of $C_{10-30}$; $R^2$ and $R^3$ individually represent a hydrogen atom, a lower alkyl group, a phenyl group or a benzyl group, or together represent a heterocyclic ring having 3–7 members; when A is $-(CH_2)n-NR^2R^3$, $R^2$ may be a hydrogen atom, a lower alkyl group, a phenyl group or a benzyl group, and $R^3$ and $R^5$ together may represent a heterocyclic ring of 6 or 7 members including two nitrogen atoms; when $-Z-B$ is $-OCONR^6-(CH_2)n-NR^2R^3$ or $-NR^6-(CH_2)n-NR^2R^3$, $R^2$ may be a hydrogen atom, a lower alkyl group, a phenyl group or a benzyl group, and $R^3$ and $R^6$ together may represent a heterocyclic ring of 6 or 7 members including two nitrogen atoms; $R^4$ is selected from the group consisting of a halogen atom, a lower alkyl group, a lower acyl group, a nitro group, a cyano group, a lower alkoxycarbonyl group, a carbamoyl group, a lower alkylcarbamoyl group, a lower alkylamino group, a lower acylamino group, a lower alkoxy group and a lower acyloxy group; $R^5$ is a hydrogen atom, a lower alkyl group, a lower acyl group or a lower alkylcarbamoyl group, or when A is $-(CH_2)n-NR^2R^3$, $R^5$ and $R^3$ together may represent a heterocyclic ring of 6 or 7 members including two nitrogen atoms; $R^6$ is a hydrogen atom, a lower alkyl group, a lower acyl group or a lower alkylcarbamoyl group, or when $-Z-B$ is $-OCONR^6-(CH_2)n-NR^2R^3$ or $-NR^6-(CH_2)n-NR^2R^3$, $R^6$ and $R^3$ together may represent a heterocyclic ring of 6 or 7 members including two nitrogen atoms; l is an integer of 0–2; and n is an integer of 0–5. The 1,2-di-substituted benzene-carboxamide derivative or the salt thereof has excellent hair growth and regrowth promoting effects, which are useful for care, improvement or prevention of hair loss in mammals and, in particular, in humans.

19 Claims, 21 Drawing Sheets

Fig. 2 Reaction Formula AB

Reaction Formula AC

Reaction Formula AD

Reaction Formula BA

Reaction Formula BB

Reaction Formula CA

Reaction Formula CB

Reaction Formula CC

Fig. 10 Reaction Formula DA

Fig. 11
Reaction Formula DB
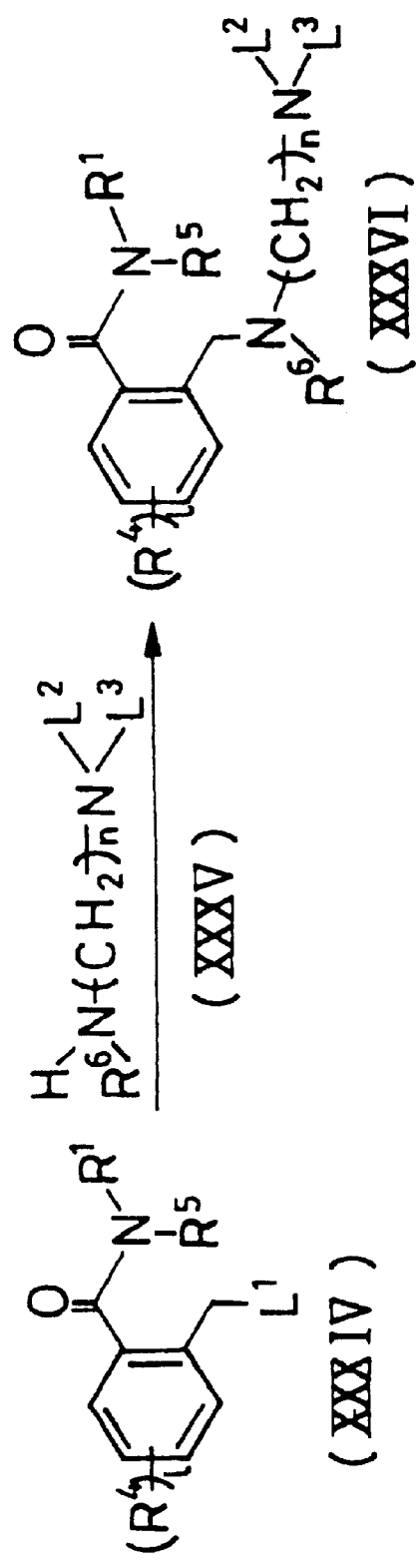
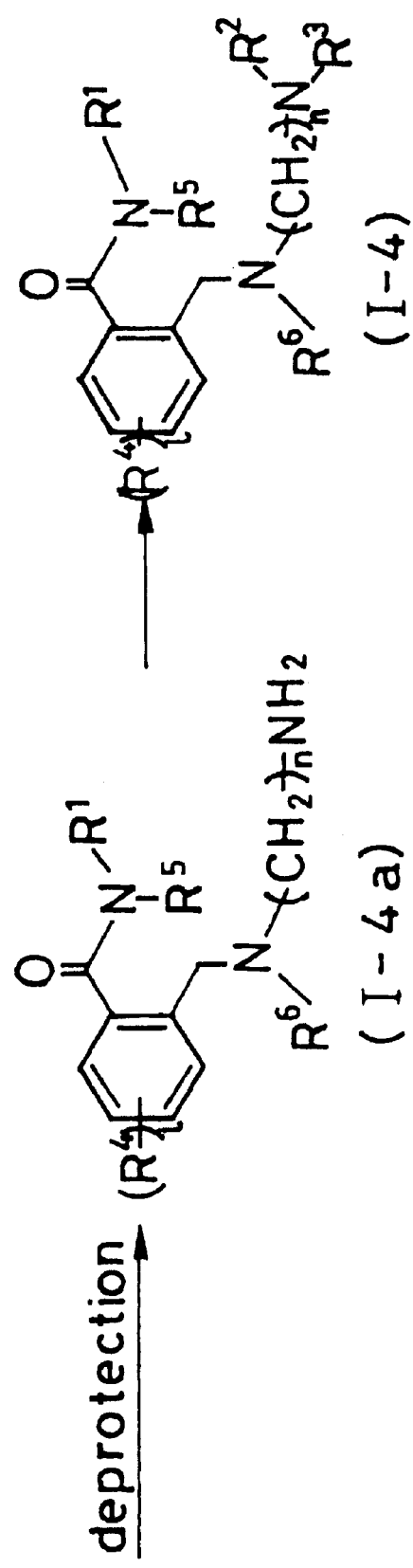

Reaction Formula EA

Reaction Formula EB

Reaction Formula EC

Reaction Formula FA

Reaction Formula FB

Fig. 17 Reaction Formula GA

Reaction Formula GB

Reaction Formula GC

Fig. 20
Reaction Formula HA
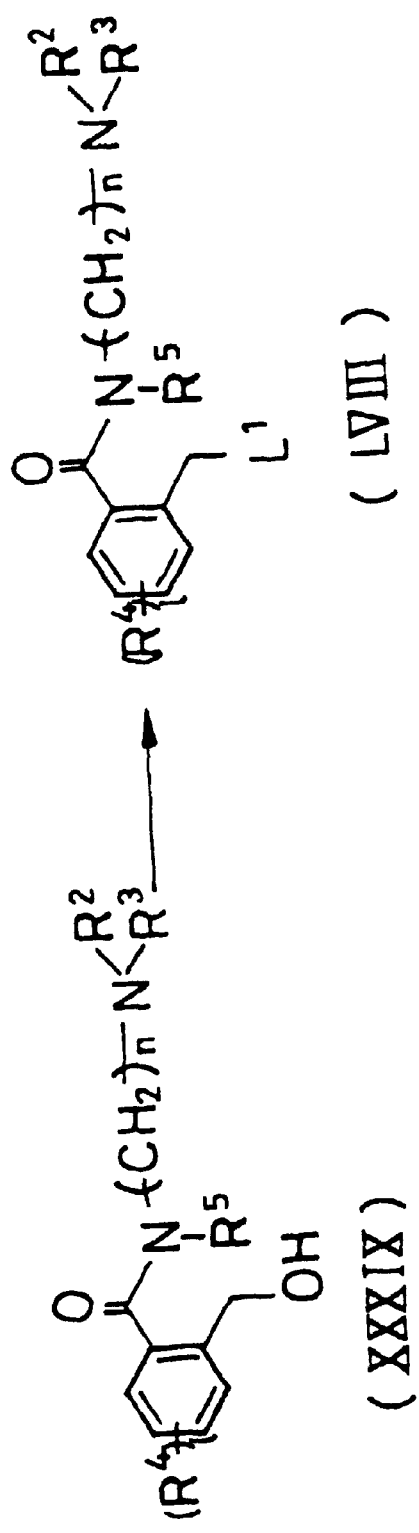
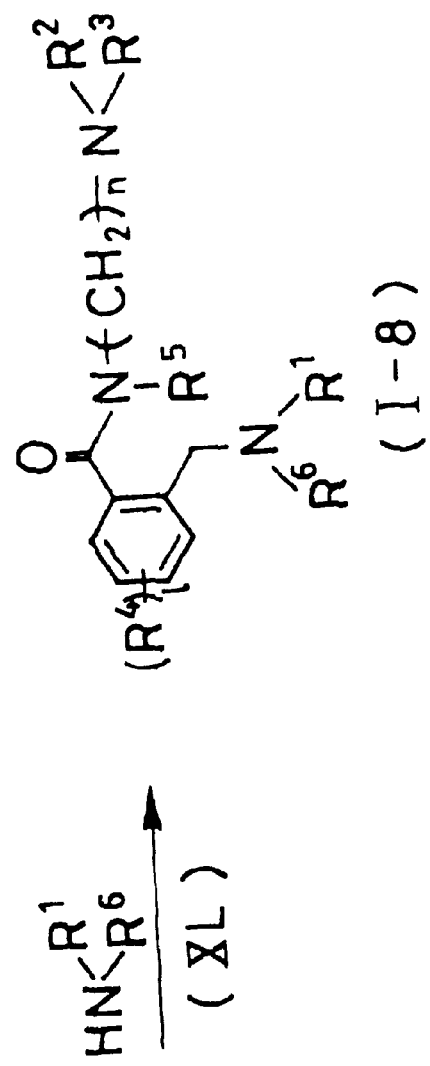

Reaction Formula HB

1,2-DI-SUBSTITUTED BENZENE-CARBOXAMIDE DERIVATIVE, HAIR GROWTH PROMOTER AND EXTERNAL COMPOSITION FOR SKIN USING THE SAME

RELATED APPLICATIONS

This application claims the priority of Japanese Patent Application No. 9-309335 filed on Oct. 23, 1997, which is incorporated herein by reference.

FIELD OF THE INVENTION

The present invention relates to a 1,2-di-substituted benzene-carboxamide derivative and, in particular, to a 1,2-di-substituted benzene-carboxamide derivative that has excellent hair growth effect.

BACKGROUND OF THE INVENTION

At the present time, scalp abnormality due to activation of androgen in an organ such as hair root or sebaceous gland, lowering of blood stream toward hair follicle, excess secretion of sebum, generation of peroxide and the like has been considered as a cause of baldness or hair loss. Accordingly, a compound or composition that can remove or reduce the above-mentioned problems has been generally included into a hair growth promoting composition to promote hair growth and regrowth and to prevent hair loss, for a long time (in the present invention, "hair growth promoting composition" includes hair regrowth promoting composition, and the like).

At present, compounds or crude drug extracts having various functions have been compounded to the hair growth promoting composition. These functions include blood flow promoting action, topical stimulation, hair follicle activating action, antiandrogen action, antiseborrheic action and the like have been known. Examples of drugs having blood flow promoting action include swertia herb extract, vitamin E and its derivative, and benzyl nicotinate. Examples of drugs which promote blood circulation by topical stimulation include capsicum tincture, cantharides tincture, camphor and vanillic acid nonylamide. Examples of drugs having hair follicle activating action include hinokitiol, placental extract, photosensitizing dye, pantothenic acid and derivative thereof. Examples of drugs having antiandrogen action include estradiol and estrone. Examples of drugs having antiseborrheic action include sulfur, thioxolone and vitamin $B_6$.

In addition to these drugs, salicylic acid, resorcine and the like that have corneocyte desquamating action and antibacterial action can be compounded to hair growth promoting composition for the purpose of preventing dandruff. Further, glycyrrhizic acid, menthol and the like can be compounded in order to prevent inflammation of scalp. Furthermore, amino acids, vitamins, extracts of crude drugs and the like can be compounded so as to aliment to hair follicle and activate enzyme activity.

Meanwhile, for example, D (L)-pantolactone (Unexamined Japanese Patent Publication No. Hei 8-26942), 2(1H)-pyridone derivative (Unexamined Japanese Patent Publication No. Hei 8-20521), $N^G$-nitro-L-arginine (Unexamined Japanese Patent Publication No. Hei 7-316023), 3-methyleneisoindolin-1-one derivative (Unexamined Japanese Patent Publication No. Hei 7-316022), indole derivative (Unexamined Japanese Patent Publication No. Hei 7-304736) are disclosed in recent patents as drugs having hair regrowth effect, hair growth effect, and hair loss protecting effect.

However, although the drugs described above are compounded to the conventional hair growth promoting compositions, they do not always exhibit sufficient hair regrowth and growth promoting effect.

SUMMARY OF THE INVENTION

In view of the foregoing problem in the prior art, an object of the present invention is to provide a compound, which is excellent in hair growth and regrowth promoting effect on human hair, and a hair growth promoting composition comprising the same as an active ingredient.

As a result of diligent studies of the inventors for attaining the above mentioned objects, it has been found that certain 1,2-di-substituted benzene-carboxamide derivative and its salt have excellent hair growth and regrowth promoting effect, thereby accomplishing the present invention.

Namely, a 1,2-di-substituted benzenecarboxamide derivative or a salt thereof in accordance with the present invention is expressed by the following Formula (I):

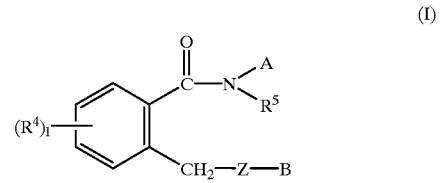

wherein
each of A and B is $R^1$ or $—(CH_2)n\text{-}NR^2R^3$, wherein when A is $R^1$, B is $—(CH_2)n\text{-}NR^2R^3$ and when A is $—(CH_2)n\text{-}NR^2R^3$, B is $R^1$;

Z is $—O—$, $—OCO—$, $—OCONR^6—$ or $—NR^6—$;

$R^1$ is a hydrocarbon group of $C_{10\text{-}30}$;

$R^2$ and $R^3$ individually represent a hydrogen atom, a lower alkyl group, a phenyl group or a benzyl group, or together represent a heterocyclic ring having 3–7 members;

when A is $—(CH_2)n\text{-}NR^2R^3$, $R^2$ may be a hydrogen atom, a lower alkyl group, a phenyl group or a benzyl group, and $R^3$ and $R^5$ together may represent a heterocyclic ring of 6 or 7 members including two nitrogen atoms;

when $—Z—B$ is $—OCONR^6—(CH_2)n\text{-}NR^2R^3$ or $—NR^6—(CH_2)n\text{-}NR^2R^3$, $R^2$ may be a hydrogen atom, a lower alkyl group, a phenyl group or a benzyl group, and $R^3$ and $R^6$ together may represent a heterocyclic ring of 6 or 7 members including two nitrogen atoms;

$R^4$ is selected from the group consisting of a halogen atom, a lower alkyl group, a lower acyl group, a nitro group, a cyano group, a lower alkoxycarbonyl group, a carbamoyl group, a lower alkylcarbamoyl group, a lower alkylamino group, a lower acylamino group, a lower alkoxy group and a lower acyloxy group;

$R^5$ is a hydrogen atom, a lower alkyl group, a lower acyl group or a lower alkylcarbamoyl group, or when A is $—(CH_2)n\text{-}NR^2R^3$, $R^5$ and $R^3$ together may represent a heterocyclic ring of 6 or 7 members including two nitrogen atoms;

$R^6$ is a hydrogen atom, a lower alkyl group, a lower acyl group or a lower alkylcarbamoyl group, or when $—Z—B$ is $—OCONR^6—(CH_2)n\text{-}NR^2R^3$ or $—NR^6—(CH_2)n\text{-}NR^2R^3$, $R^6$ and $R^3$ together may represent a heterocyclic ring of 6 or 7 members including two nitrogen atoms;

l is an integer of 0–2; and n is an integer of 0–5.

A hair growth promoting composition in accordance with the present invention is characterized by comprising said 1,2-di-substituted benzene-carboxamide derivative or the pharmacologically acceptable salt thereof as an effective ingredient.

An external preparation for skin in accordance with the present invention is characterized by comprising said 1,2-di-substituted benzene-carboxamide derivative or the pharmacologically acceptable salt thereof.

A method for promoting hair growth in accordance with the present invention is characterized by applying an effective amount of said 1,2-di-substituted benzene-carboxamide derivative or the pharmacologically acceptable salt thereof on the skin of mammals and, in particular, on human scalp.

BRIEF DESCRIPTION OF THE DRAWINGS

FIGS. 1–21 show examples of steps for manufacturing the 1,2-di-substituted benzene-carboxamide derivative in accordance with the present invention.

BEST MODE FOR CARRYING OUT THE INVENTION

Figure 1:
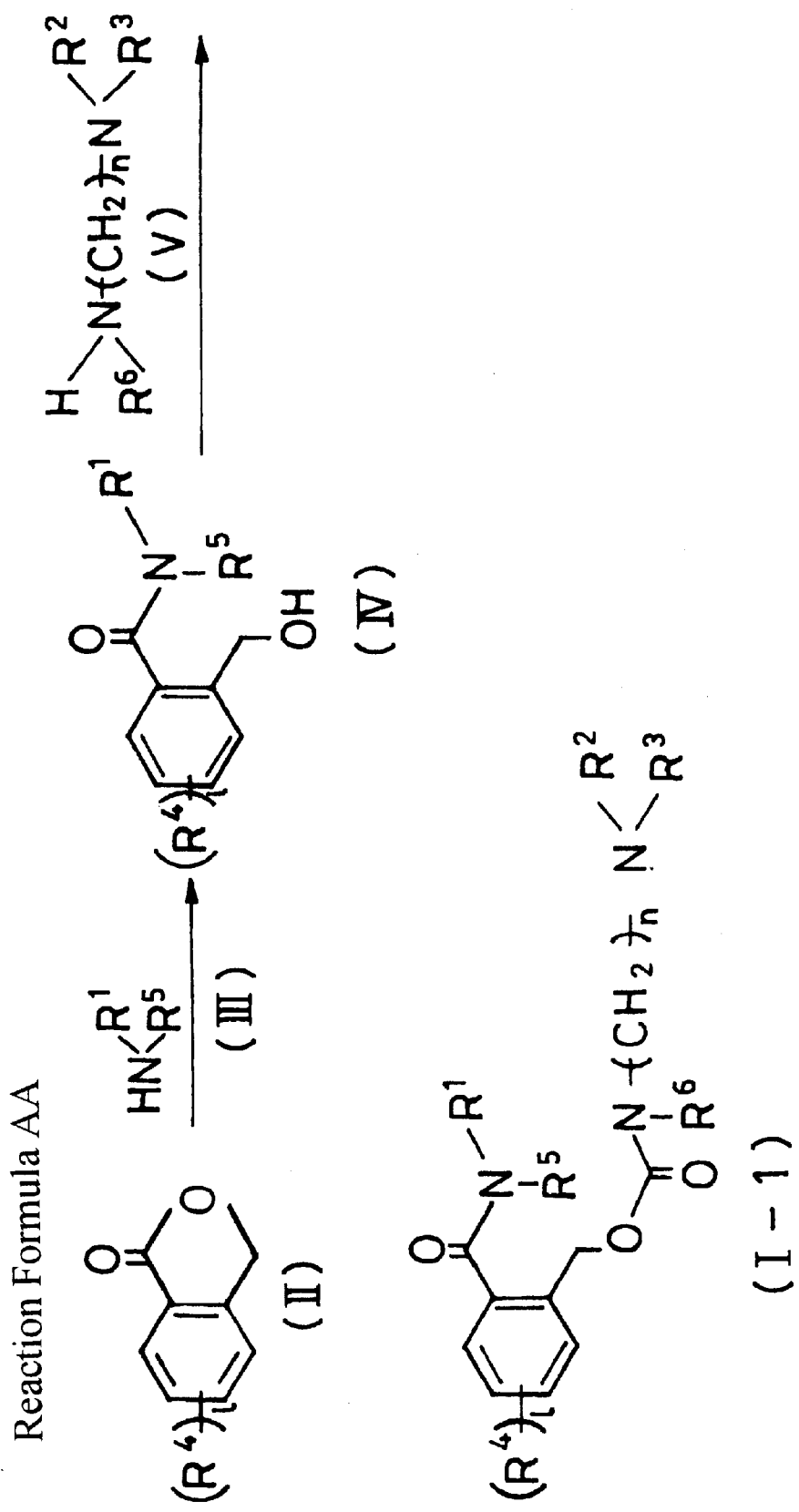

In a compound of the present invention, hydrocarbon group of $CO_{10-30}$ shown by $R^1$ refers to a straight or branched alkyl group having 10–30 carbon atoms, a straight or branched alkenyl group having 10–30 carbon atoms or a straight or branched alkynyl group having 10–30 carbon atoms and may have a saturated ring or aromatic ring in $R^1$.

Examples of the above-mentioned straight alkyl group include decyl, undecyl, dodecyl, tridecyl, tetradecyl, pentadecyl, hexadecyl, heptadecyl, octadecyl, nonadecyl, icosyl, henicosyl, docosyl, tetracosyl, hexacosyl octacosyl and the like.

Examples of the above-mentioned branched alkyl group include 6-methyldecyl, 9-methyldecyl, 6-ethylnonyl, 5-propyloctyl, 11-methyldodecyl, 12-methyltridecyl, 4-methyltetradecyl, 13-methyltetradecyl, 14-ethylhexadecyl, 10-methyloctadecyl, 15-ethylheptadecyl, 10-methyldococyl, 2-pentyloctadecyl, 22-methyltricosyl, 12-hexyloctadecyl, 6-methyltetracosyl, 24-methylheptacosyl, 2-decylhexadecyl, 2-nonyloctadecyl, 2-dodecyloctadecyl and the like.

Examples of straight or branched alkenyl group having 10–30 carbon atoms and straight or branched alkynyl group having 10–30 carbon atoms include the alkenyl groups or alkynyl groups corresponding to the above-mentioned alkyl groups such as 4-decenyl, 7-dodecenyl, 9-octadodecenyl or 3-clodecynyl.

Also, examples of hydrocarbon group having a saturated ring or an aromatic ring in $R^1$ include 12-cyclohexyldodecyl, 4-butylphenyl, 8-phenyloctyl, biphenylyl, and the like.

Among these groups, $R^1$ is preferably a straight or branched alkyl group having 10–30 carbon atoms and, more preferably, a straight or branched alkyl group having 10–20 carbon atoms and, particularly preferably, a straight alkyl group having 10–20 carbon atoms. The hair growth effect tends to deteriorate in the case where the carbon number of $R^1$ is too small.

Each of $R^2$ and $R^3$, which may be identical or different from each other, can be a hydrogen, a lower alkyl, a phenyl or a benzyl group. Also, $R^2$ and $R^3$ together can represent a heterocycle having 3–7 members. Further, when A is —$(CH_2)$n-$NR^2R^3$, $R^2$ may be a hydrogen atom, a lower alkyl group, a phenyl group or a benzyl group, and $R^3$ and $R^5$ together may represent a heterocyclic ring of 6 or 7 members including two nitrogen atoms. Also, when —Z—B is —$OCONR^6$—$(CH_2)$n-$NR^2R^3$ or —$NR^6$—$(CH_2)$n-$NR^2R^3$, $R^2$ may be a hydrogen atom a lower alkyl group, a phenyl group or a benzyl group, and $R^3$ and $R^6$ together may represent a heterocyclic ring of 6 or 7 members including two nitrogen atoms.

In $R^2$ and $R^3$, the lower alkyl group refers to a straight or branched alkyl group having 1–6 carbon atoms. Examples of the lower alkyl group include methyl, ethyl, propyl, butyl, isopropyl, isobutyl, 1-methylpropyl, tert-butyl, pentyl, 1-ethylpropyl, isoamyl, hexyl and the like. Methyl, ethyl, isopropyl, or butyl group is preferable for the lower alkyl group in $R^2$ and $R^3$. In the present invention, the definition of lower alkyl group is the same as mentioned above if there is no further description.

Also, the lower alkyl group in $R^2$ and $R^3$ may be substituted by a hydroxyl group. Examples of such a hydroxy lower alkyl group include 2-hydroxyethyl group.

In $R^2$ and $R^3$, a phenyl and a benzyl group may be unsubstituted or substituted by a halogen, a lower alkyl, a lower acyl, a nitro, a cyano, a lower alkoxycarbonyl, a lower alkylamino, a lower alkoxy or a lower acyloxy group, respectively. The definition of each substituent referred in here is explained as follows:

The halogen atom represents chlorine, bromine, iodine or fluorine.

The lower alkyl group is as mentioned above and, preferably, is methyl or ethyl group.

The lower acyl group is a straight or branched acyl group having 2–7 carbon atoms. Examples of the lower acyl group include acetyl, propionyl, butyryl, isobutyryl, pivaloyl, benzoyl group and the like.

The lower alkoxycarbonyl group represents a carboxyl group whose hydrogen atom is substituted by a lower alkyl group. A preferable example of the lower alkoxycarbonyl group is methoxycarbonyl or ethoxycarbonyl group.

The lower alkylamino group represents an amino group whose hydrogen atom is substituted by one or two of the same or different lower alkyl group. A preferable example of the lower alkylamino group is methylamino or dimethylamino group.

The lower alkoxy group represents a hydroxyl group whose hydrogen atom is substituted by a lower alkyl group. A preferable example of the lower alkoxy group is methoxy or ethoxy group.

The lower acyloxy group represents a hydroxyl group whose hydrogen atom is substituted by a lower acyl group, wherein said lower acyl group is as above-mentioned. A preferable example of the lower acyloxy group is acetoxy or propionyloxy group.

In $R^2$ and $R^3$ the heterocycle having 3–7 members which is formed by $R^2$ and $R^3$ together represents a saturated or unsaturated heterocycle having 3–7 members containing nitrogen atom to which $R^2$ and $R^3$ are bonded. In addition to the nitrogen atom, a hetero atom such as nitrogen atom or oxygen atom may be contained in the heterocycle. Examples of the heterocycle include aziridine, azetidine, pyrrolidine, piperidine, homopiperidine, piperazine, morpholine, pyrrole, pyrazole, and imidazole ring. Among these heterocycles, pyrrolidine, piperidine, piperazine or morpholine ring is preferable. The heterocycle may be substituted by one or two of the same or different substituent. Such a substituent can be selected from the group consisting of a lower alkyl, a lower alkoxy, a lower acyl and a nitro group. The lower alkyl group is preferably methyl or ethyl group. The lower alkoxy group is preferably methoxy or ethoxy group. The lower acyl group is preferably acetyl, propionyl or butyryl group.

The heterocyclic ring of 6–7 members which is formed by $R^3$ and $R^5$ or by $R^3$ and $R^6$ contains two nitrogen atoms. Examples of compounds of the present invention containing the heterocyclic ring of 6–7 members may be expressed by the following Formula (IA), (IB), (IC), or (ID):

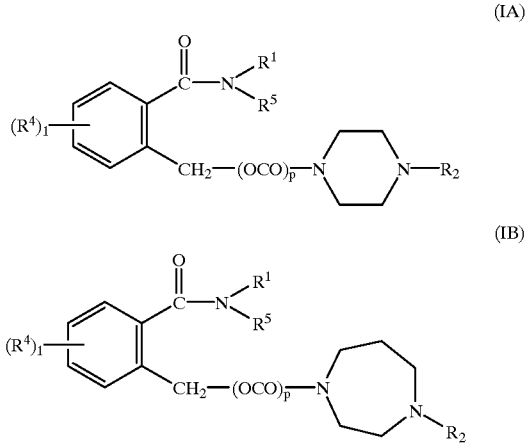

(IA)

(IB)

wherein
$R^2$ is a hydrogen atom, a lower alkyl group, a phenyl group or a benzyl group;
$R^5$ is a hydrogen atom, a lower alkyl group, a lower acyl group or a lower alkylcarbamoyl group;
p is 0 or 1; and
$R^1$, $R^4$ and l are as defined in Formula (I):

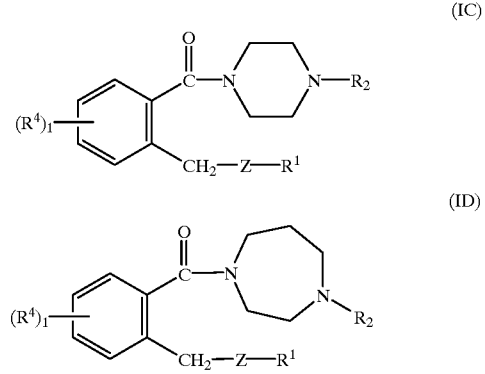

(IC)

(ID)

wherein
$R^2$ is a hydrogen atom, a lower alkyl group, a phenyl group or a benzyl group;
Z is —O—, —OCO—, —OCONR$^6$— or —NR$^6$—, wherein $R^6$ is a hydrogen atom, a lower alkyl group, a lower acyl group or a lower alkylcarbamoyl group; and
$R^1$, $R^4$ and l are as defined in Formula (I).

Among compounds expressed by Formula (IA) to (ID), a compound expressed by Formula (IA) or (IC) is preferable. Also, p is preferably 1.

In the present invention, it is preferable that $R^2$ and $R^3$ are lower alkyl groups or a heterocycle having 3–7 members, or that $R^2$ is a lower alkyl group, while $R^3$ and either $R^5$ or $R^6$ together form a heterocyclic ring of 6–7 members containing two nitrogen atoms.

$R^4$ can be a halogen atom, a lower alkyl group, a lower acyl group, a nitro group, a cyano group, a lower alkoxycarbonyl group, a carbamoyl group, a lower alkylcarbamoyl group, a lower alkylamino group, a lower acylamino group, a lower alkoxy group or a lower acyloxy group.

As for $R^4$, the definitions for halogen, lower alkyl, lower acyl, lower alkoxycarbonyl, lower alkylamino, lower alkoxy and lower acyloxy groups are identical to those in $R^2$ and $R^3$.

The lower alkylcarbamoyl group in $R^4$ represents a carbamoyl group whose one or two hydrogen atoms are substituted by a lower alkyl group. A preferable example of the lower alkylcarbamoyl group is methylcarbamoyl or ethylcarbamoyl group.

The lower acylamino group in $R^4$ represents an amino group whose one or two hydrogen atoms are substituted by a lower acyl group. The lower acyl group is as mentioned above. A preferable example of the lower acylamino group is acetylamino, propionylamino or benzoylamino group.

Preferably, $R^4$ is a lower alkoxy group and, more preferably, methoxy group.

$R^5$ is a hydrogen atom, a lower alkyl group, a lower acyl group or a lower alkylcarbamoyl group. Also, when A is —(CH$_2$)n-NR$^2$R$^3$, $R^5$ and $R^3$ together may represent a heterocyclic ring of 6 or 7 members including two nitrogen atoms as mentioned above.

$R^5$ is preferably a hydrogen atom or a heterocyclic ring of 6 or 7 members which is formed by $R^5$ and $R^3$ together.

$R^6$ is a hydrogen atom, a lower alkyl group, a lower acyl group or a lower alkylcarbamoyl group. Also, when —Z—B is —OCONR$^6$—(CH$_2$)n-NR$^2$R$^3$ or —NR$^6$—(CH$_2$)n-NR$^2$R$^3$, $R^6$ and $R^3$ together may represent a heterocyclic ring of 6 or 7 members including two nitrogen atoms as mentioned above.

$R^6$ is preferably a hydrogen atom or a heterocyclic ring of 6 or 7 members which is formed by $R^6$ and $R^3$ together.

As for $R^5$ and $R^6$, the definitions for lower alkyl and lower acyl groups are identical to those in $R^2$ and $R^3$ and the definition for lower alkylcarbamoyl group is identical to that in $R^4$.

Z is a divalent group expressed by —O—, —OCO—, —OCONR$^6$— or —NR$^6$— and, preferably, —OCONR$^6$—.

In the present invention, l is an integer of 0–2 and, preferably, 0.

Also, n is an integer of 0–5 and, preferably, an integer of 2–5 in point of stability or the like.

In the compound of the present invention shown by Formula (I), an asymmetric carbon may exist in any group of $R^1$, $R^2$, $R^3$, $R^4$, $R^5$ or $R^6$. In addition to the various optical isomers based on such asymmetric carbon, the present invention can comprise geometrical isomers, conformational isomers, the other isomers and the mixture thereof.

The Compound (I) provided in the present invention can be manufactured by using well-known reactions. Although, as for the representative examples, a synthetic method will be shown in the following, the present invention should not be restricted thereto. Also, in the following manufacturing methods, $R^1$, $R^2$, $R^3$, $R^4$, $R^5$, $R^6$, l and n are the same as shown in the definitions of Formula (I), unless otherwise indicated.

Compound (I-1)
(A=R$^1$, B=—(CH$_2$)n-NR$^2$R$^3$, Z=—OCONR$^6$—)

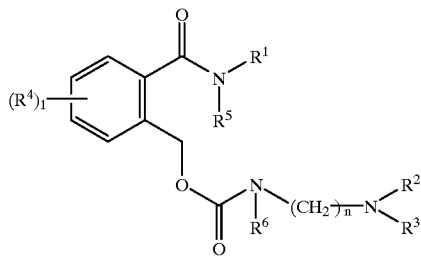

(I-1)

Compound (I-1) of the present invention can be synthesized as shown in Reaction Formula AA in FIG. 1. Namely, a phthalide (II) is reacted with an amine (III) to produce Compound (IV). Then, Compound (IV) is reacted with an amine (V), thereby producing Compound (I-1).

The reaction at the first step can be effected with or without a solvent. As a solvent, for example, a halogenated hydrocarbon such as dichloromethane or chloroform; an aromatic compound such as benzene, toluene, xylene, or pyridine; an ether such as tetrahydrofuran or 1,4-dioxane; or an amide such as N,N-dimethylformamide or N,N-dimethylacetamide can be used. The reaction temperature can be within the range of room temperature to 150° C. Preferably, the reaction is effected without solvent at a temperature within the range of room temperature to 100° C.

At the second step, using phenyl chlorocarbonate, phosgene, diphosgene, triphosgene, di-2-pyridylketone or the like, Compound (IV) is converted into its corresponding carbonate. Then, the carbonate is reacted with the amine (V). As an additive, for example, a base such as triethylamine, N,N-diisopropylethylamine, pyridine or sodium carbonate can be used. As a solvent, for example, a halogenated hydrocarbon such as dichloromethane or chloroform; an aromatic compound such as benzene, toluene, or xylene; or an ether such as tetrahydrofuran or 1,4-dioxane can be used. While the reaction temperature and reaction time may be changed according to the material compounds used, the reaction is usually effected at a temperature within the range of −15° C. to the reflux temperature of the solvent. Specifically, for example, by using pyridine or N,N-diisopropylethylamine as an additive, Compound (IV) is reacted with phenyl chlorocarbonate or triphosgene in a solvent such as chloroform or dichloromethane at a temperature within the range of −15° C. to room temperature to produce its corresponding carbonate. Then, the carbonate is reacted with the amine (V) in the absence or presence of a solvent such as chloroform or dichloromethane at a temperature of room temperature to 100° C., thereby attaining the aimed object.

In this second step reaction, Compound (I-1) wherein R$^6$ is a hydrogen atom can be also synthesized by addition reaction of Compound (IV) with the corresponding isocyanate, OCN—(CH$_2$)n-NR$^2$R$^3$. In this addition reaction, the isocyanate group is added to a hydroxyl group of Compound (IV) to form a carbamoyloxy group, —OCONH—. As an additive, for example, an acid such as boron trifluoride-ethyl etherate, hydrochloric acid, aluminum chloride, dialkyltin dichloride or dialkyltin acetate, or a base such as triethylamine, N,N-diisopropylethylamine, pyridine, N-methylmorpholine, N-methylpiperidine, or sodium acetate can be used. As a solvent, for example, a halogenated hydrocarbon such as dichloromethane or chloroform; an aromatic compound such as benzene, toluene, or xylene; an ether such as tetrahydrofuran or 1,4-dioxane; or an amide such as N,N-dimethylformamide or N,N-dimethylacetamide can be used. While the reaction temperature and reaction time may be changed according to the material compounds used, the reaction is usually effected at a temperature within the range of 0° C. to the reflux temperature of the solvent. Specifically, for example, by using triethylamine as an additive, Compound (IV) is reacted with the isocyanate in a solvent such as dichloromethane at a temperature within the range of 0° C. to room temperature, thereby attaining the aimed object.

Such isocyanates can be commercially available or obtained by a reaction wherein the corresponding amine (V) is reacted with phosgene, diphosgene, triphosgene or the like in the absence or presence of a base, or by a reaction wherein a corresponding carboxylic acid HO$_2$C—(CH$_2$)n-NR$^2$R$^3$, is reacted with diphenylphosphoryl azide or the like in the presence of a base. As a base in this reaction, for example, an organic base such as triethylamine, N,N-diisopropylethylamine or pyridine can be used. As a solvent, for example, a halogenated hydrocarbon such as dichloromethane or chloroform; an aromatic compound such as benzene, toluene, or xylene; an ether such as tetrahydrofuran or 1,4-dioxane; or an amide such as N,N-dimethylformamide or N,N-dimethylacetamide can be used.

This carbamoyloxy group forming reaction by a hydroxyl group and an isocyanate can be used in Reaction Formulas AB to AC and EA to EC mentioned below. Also, the isocyanates used in each Reaction Formulas can be synthesized in the similar manner to the above.

Figure 2:
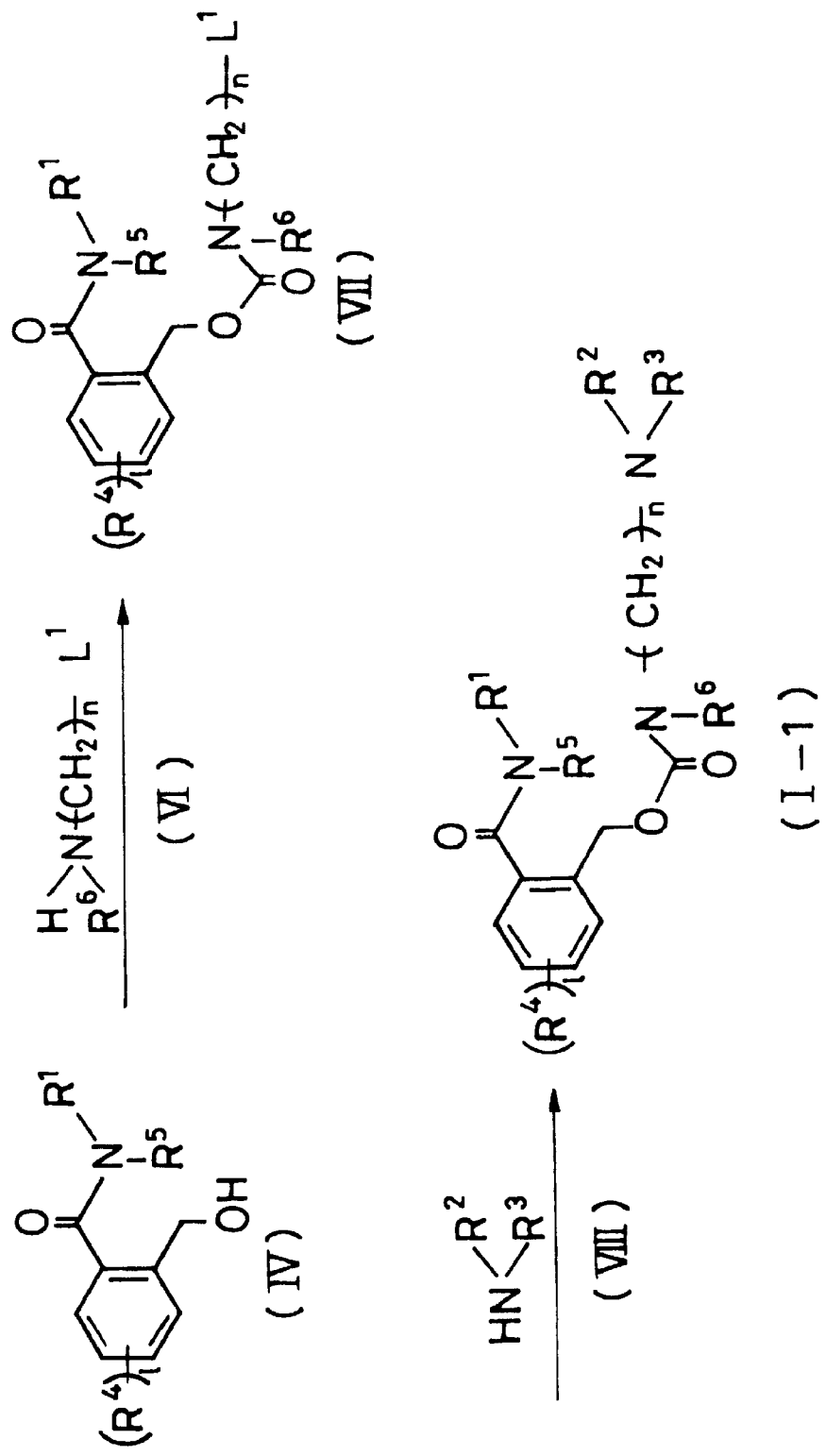

The Compound (I-1) can be also synthesized as shown in Reaction Formula AB of FIG. 2. First, Compound (IV) is reacted with an amine (VI) to produce Compound (VII). Then, Compound (VII) is reacted with an amine (VIII), thereby producing Compound (I-1). Here, L$^1$ represents an atom or a group which is substituted by nitrogen easily and can be a halogen, tosyloxy, mesyloxy group or the like. The definition of L$^1$ throughout the rest of this specification is the same as stated above.

The first step of Reaction Formula AB can be effected according to the reaction of the second step in Reaction Formula AA.

The reaction at the second step in Reaction Formula AB can be effected in the presence of a base. As a base, for example, an inorganic base such as potassium carbonate, potassium hydroxide, sodium hydroxide or sodium hydride, or an organic base such as triethylamine or pyridine can be used. As a solvent, toluene, ether, tetrahydrofuran, acetone, N,N-dimethylformamide or the like can be used. Specifically, for example, by using potassium carbonate as a base, the reaction is effected in a solvent such as acetone or N,N-dimethylformamide at the temperature with the range of room temperature to the reflux temperature of the solvent, thereby attaining the aimed object.

Figure 3:
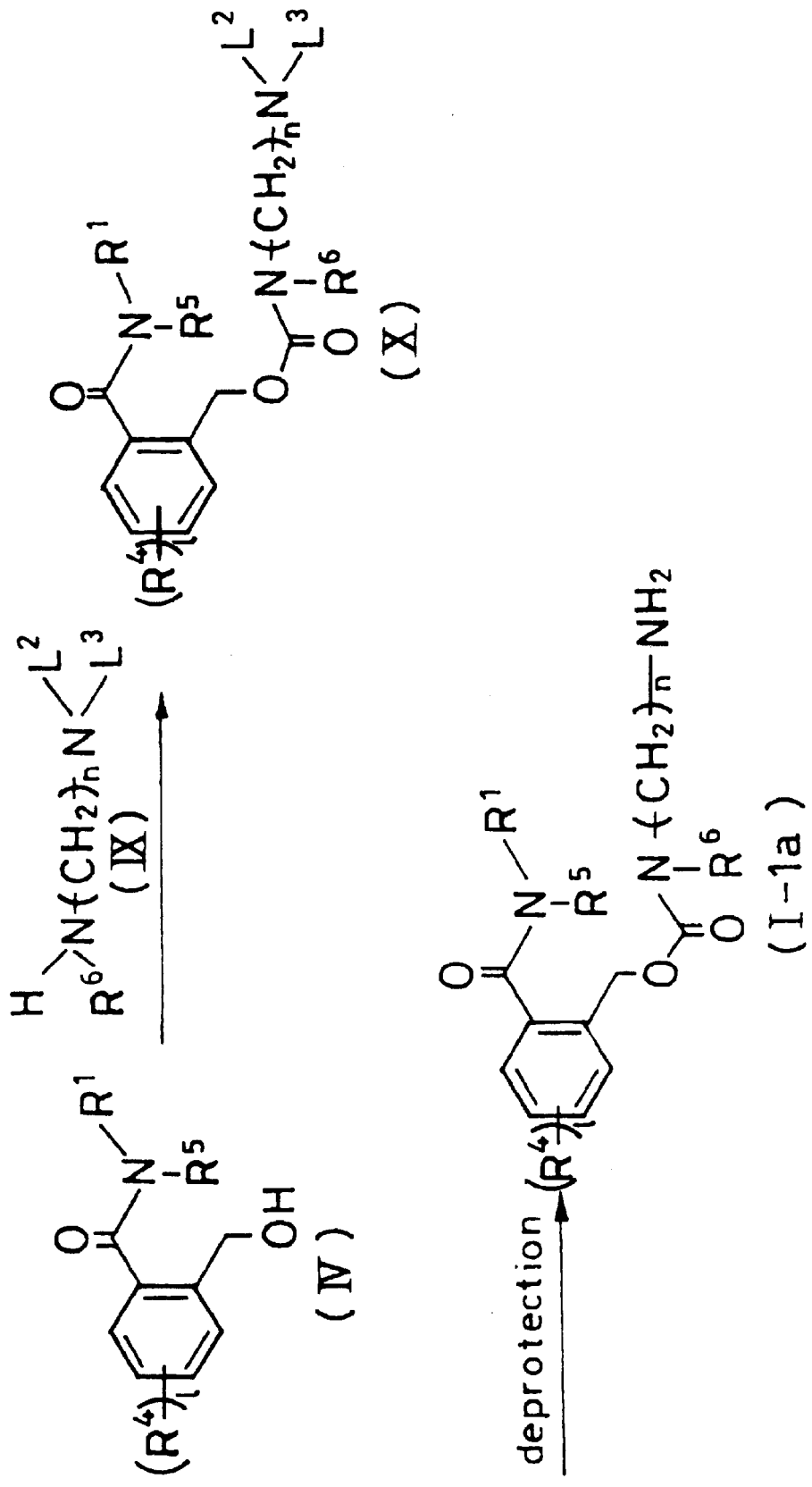

Also, Compound (I-1a) wherein R$^2$ and R$^3$ in Compound (I-1) are hydrogen atoms can be synthesized as shown in Reaction Formula AC of FIG. 3. First, Compound (IV) is reacted with an amine (IX) to produce Compound (X). Then, Compound (X) is deprotected to produce Compound (I-1a). In Reaction Formula AC, either L$^2$ or L$^3$ can be an amino protecting group such as an urethane type protecting group (e.g., tert-butoxycarbonyl, benzyloxycarbonyl or 9-fluorenylmethyloxycarbonyl group), a sulfonyl type protecting group (e.g., 2-(trimethylsilyl)ethanesulfonyl group), a sulfenyl type protecting group (e.g., 2,2,2-trifluoro-1,1-diphenylethanesulfenyl group), or an alkyl type protecting group (e.g., benzyl, trityl or 9-phenylfluorenyl group), while the other can be a hydrogen atom. Also, $L^2$ and $L^3$ together can form a phthalimide type amino protecting group. Further, other protecting group can be used unless it is adverse to the object of this Reaction Formula. The definition of $L^2$ and $L^3$ throughout the rest of this specification is the same as stated above.

The first step in Reaction Formula AC can be effected according to the reaction of the second step in Reaction Formula AA.

For the deprotection at the second step in Reaction Formula AC, various kind of known methods can be used according to the type of amino protecting group $L^2$ and $L^3$. Specifically, for example, in the case where $L^2$ is a benzyloxycarbonyl group and $L^3$ is a hydrogen atom, the reaction is effected in a solvent such as ethanol or ethyl acetate by using palladium-carbon as a catalyst at a temperature within the range of room temperature to the reflux temperature of the solvent, thereby attaining the aimed object. Also, in the case where $L^2$ and $L^3$ together form a phthalimide type amino protecting group, by using hydrazine as a deprotection agent, the reaction is effected in ethanol at a temperature within the range of room temperature to the reflux temperature of the solvent, thereby attaining the aimed object.

Figure 4:
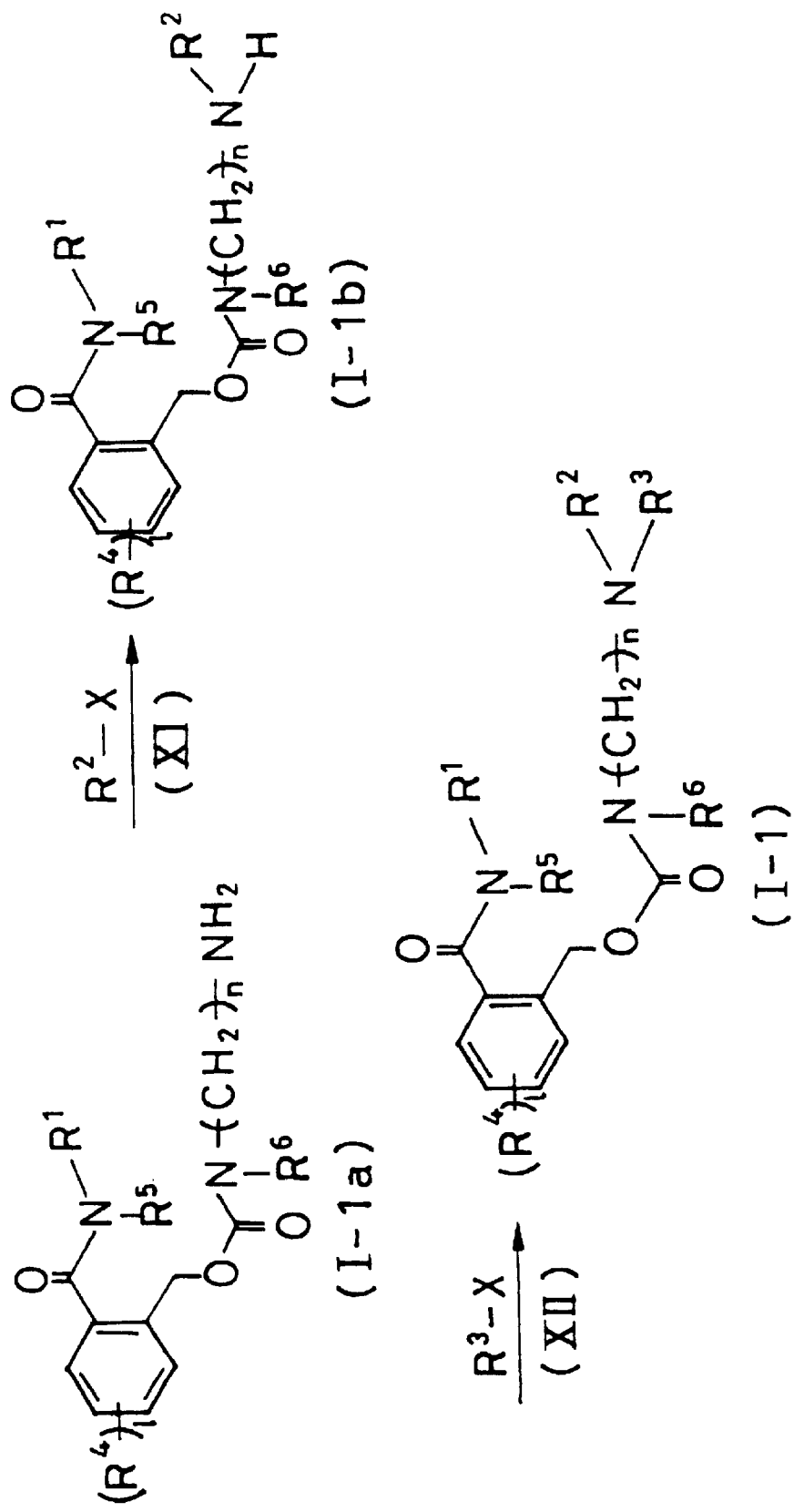

This Compound (I-1a), as shown in Reaction Formula AD of FIG. 4, can be converted into Compound (I-1b) by reacting with about one equivalent amount of halogenated compound (XI) in the presence of a base. Further, Compound (I-1) can be obtained by reacting Compound (I-1b) with halogenated compound (XII) in the similar manner to the above. X represents a halogen atom. The definition of X throughout the rest of this specification remains the same.

In this reaction, when $R^2$ and $R^3$ are lower alkyl, phenyl or benzyl groups, an inorganic base such as potassium carbonate, potassium hydroxide, sodium hydroxide or sodium hydride; or an organic base such as triethylamine or pyridine can be used as a base. Specifically, for example, by using potassium carbonate as a base, the reaction is effected in a solvent such as acetone or N,N-dimethylformamide at a temperature within the range of room temperature to the reflux temperature of the solvent, thereby attaining the aimed object.

In the similar manner to this Reaction Formula AD, by reacting Compound (I-1a) with about twice equivalent amount of halogenated compound (XI) in the presence of a base, a compound wherein $R^2$ and $R^3$ in Compound (I-1) are the same can be obtained. Also, by reacting Compound (I-1a) with a suitable dihalogenated compound, a compound wherein $R^2$ and $R^3$ in Compound (I-1) together form a heterocycle having 3–7 members can be obtained.

Although a compound wherein $R^5$ or $R^6$ in Compound (I-1) is a lower alkyl, a lower acyl, or a lower alkylcarbamoyl group can be synthesized according to the above-mentioned Reaction Formula, it can be also synthesized as follows. First, a compound wherein $R^5$ or $R^6$ in Compound (I-1) is a hydrogen atom is synthesized according to the above-mentioned Reaction Formula. Then, the resulting compound is reacted with the corresponding halide such as alkyl halide, acyl halide, or alkylcarbamoyl halide in the absence or presence of a base. This is the same in the synthesis of Compounds (I-2) to (I-8) mentioned below.

Compound (I-2)

$(A=R^1, B=—(CH_2)n-NR^2R^3, Z=—O—)$

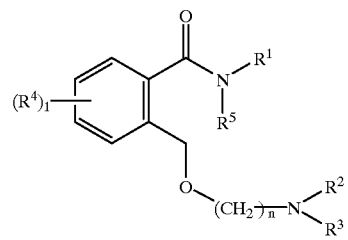

(I-2)

Figure 5:
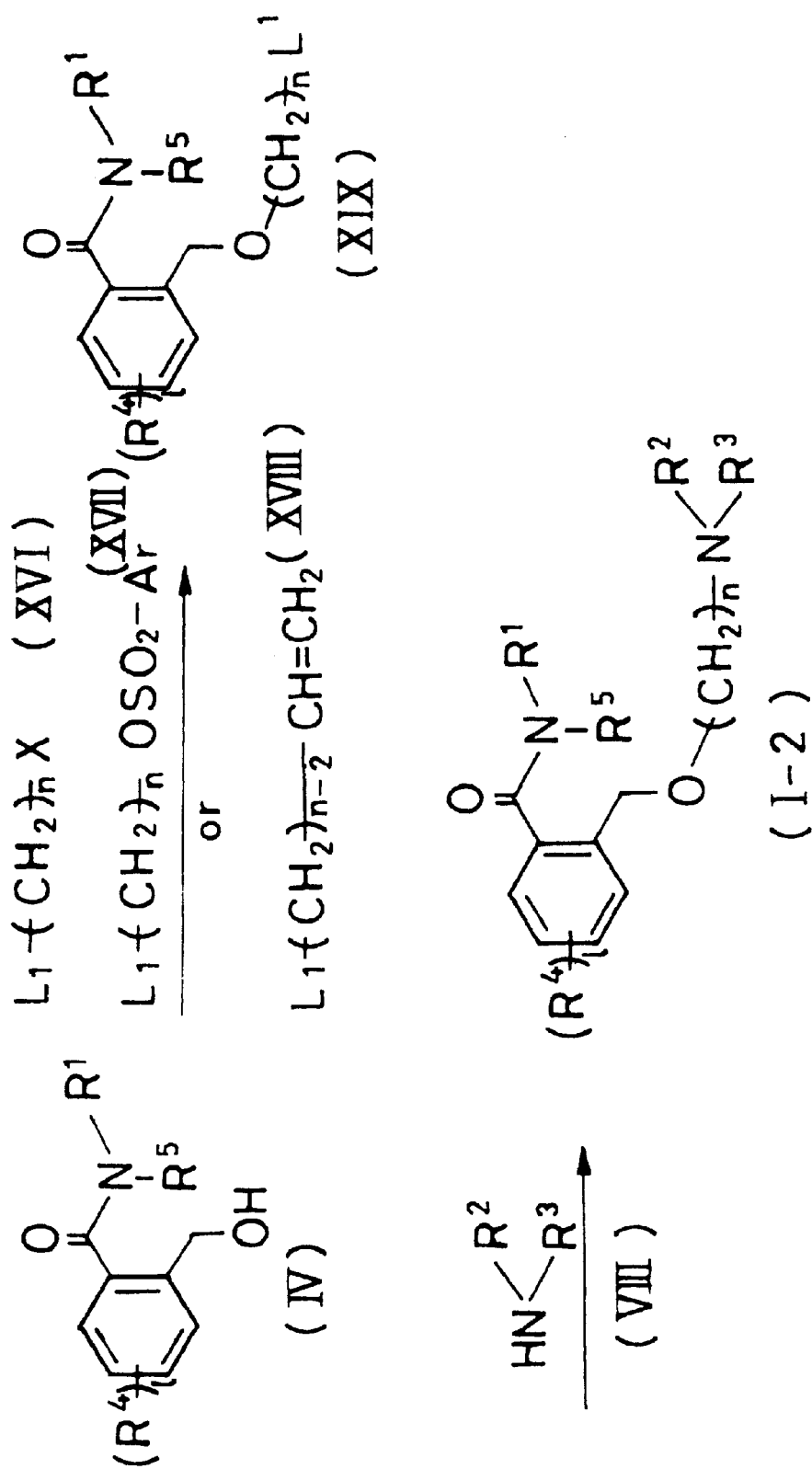

Compound (I-2) of the present invention can be synthesized as shown in Reaction Formula BA of FIG. 5. Namely, a hydroxyl group of Compound (IV) is alkylated to produce Compound (XIX). Then, Compound (XIX) is reacted with amine (VIII), thereby producing Compound (I-2).

The reaction at the first step in Reaction Formula BA can be effected by substitution reaction of Compound (IV) with an halide (XVI) or a sulfonate (XVII), or when n is an integer of 3 or more, by addition reaction with an alkene (XVIII).

In the substitution reaction with the halide (XVI), Compound (IV) is converted into its corresponding alkoxide by using metallic sodium, sodium hydride or the like and then the alkoxide is reacted with halide (XVI). Also, Compound (IV) can be reacted with halide (XVI) in the presence of a base directly. As a base, sodium amide, potassium carbonate, sodium hydroxide, barium oxide, silver oxide, or the like can be used. As a solvent, an aromatic compound such as benzene, toluene, or xylene; an ether such as tetrahydrofuran or 1,4-dioxane; an amide such as N,N-dimethylformamide or N,N-dimethylacetamide; acetonitrile; dimethyl sulfoxide; or the like can be used. While the reaction temperature and reaction time may be changed according to the material compounds used, the reaction is usually effected at a temperature within the range of 0° C. to the reflux temperature of the solvent. Specifically, for example, Compound (IV) is reacted with the halide (XVI) in acetone in the presence of potassium carbonate at a temperature within the range of room temperature to the reflux temperature of the solvent, thereby attaining the aimed object.

In the substitution reaction with the sulfonate (XVII), as a solvent, benzene, tetrahydrofuran, 1,4-dioxane, N,N-dimethylformamide, dimethyl sulfoxide, dichloromethane, water or the like can be used. While the reaction temperature and reaction time may be changed according to the material compounds used, the reaction is usually effected at a temperature within the range of 0° C. to the reflux temperature of the solvent. The sulfonate (XVII) can be easily synthesized from the corresponding alcohol and p-toluenesulfonyl chloride in the presence of a base such as pyridine. Specifically, for example, a solution of the corresponding alcohol and p-toluenesulfonyl chloride in 1,4-dioxane is added to sodium hydroxide aqueous solution at a temperature within the range of 0° C. to room temperature and then Compound (IV) is added thereto, thereby attaining the aimed object. Ar in the sulfonate (XVII) represents 4-methylphenyl or naphtyl group. The definition of Ar throughout the rest of this specification remains the same.

Also, by using other ester type compound in place of the sulfonate (XVII) a substitution reaction is effected in the similar manner to this method to obtain Compound (I-2). For example, a carbonate or a trichloroacetoimidate corresponding to the sulfonate (XVII) can be used therefor.

The addition reaction with the alkene (XVIII) can be effected in the presence of an acidic catalyst. Examples thereof include hydrochloric acid, sulfuric acid, boron trifluoride, trifluoromethanesulfonic acid, and tetrafluoroboric acid. In place of the acidic catalyst, an organometallic compound can be used. This reaction can be effected with or without a solvent which can be benzene, tetrahydrofuran, diethyl ether, 1,4-dioxane, N,N-dimethylformamide, dichloromethane or the like. While the reaction temperature and reaction time may be changed according to the material compounds used, the reaction is usually effected at a temperature within the range of −100° C. to 200620 C. Specifically, for example, trifluoromethanesulfonic acid is added to a solution of Compound (IV) and the alkene (XVIII) in dichloromethane at a temperature within the range of −78° C. to 0°C., thereby attaining the aimed object.

The second step of Reaction Formula BA can be effected according to the reaction of the second step in Reaction Formula AB.

Figure 6:
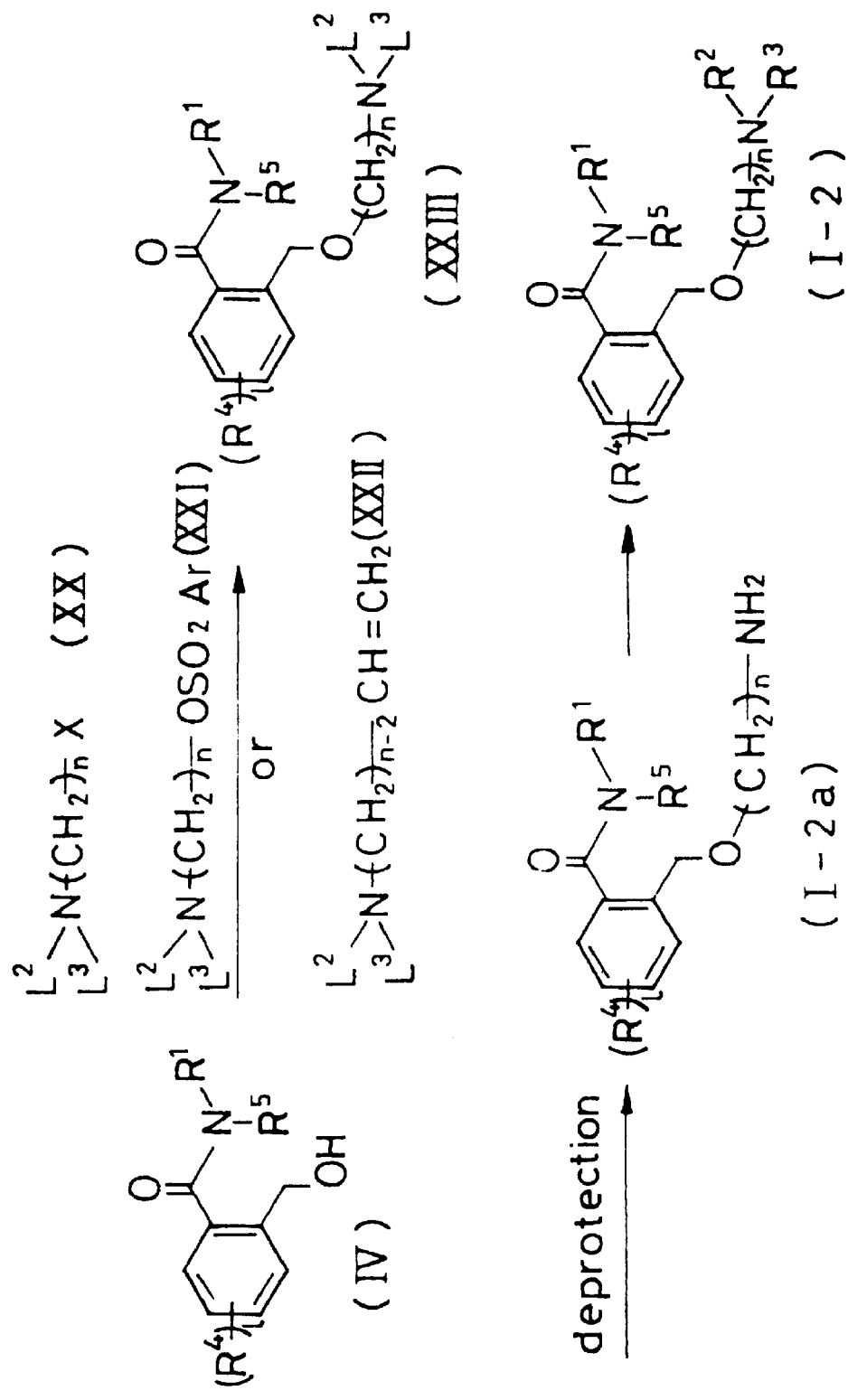

Also, Compound (I-2a) wherein $R^2$ and $R^3$ in Compound (I-2) are hydrogen atoms can be synthesized as shown in Reaction Formula BB of FIG. 6. First, a hydroxyl group of Compound (IV) is alkylated to produce Compound (XXIII). Then, Compound (XXIII) is deprotected, thereby producing Compound (I-2a). The alkylation at the first step in Reaction Formula BB can be effected according to the reaction of the first step in Reaction Formula BA. The deprotection at the second step of Reaction Formula BB can be effected according to the reaction of the second step in Reaction Formula AC. Further, in the similar manner to Reaction Formula AD, Compound (I-2a) can be converted into Compound (I-2).

Compound (I-3)
(A=$R^1$, B=—(CH$_2$)n-NR$^2$R$^3$, Z=—OCO—)

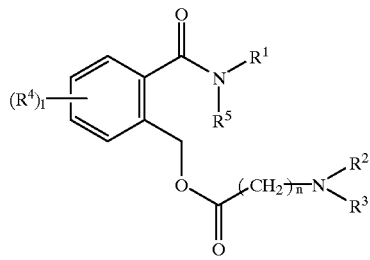

(I-3)

Figure 7:
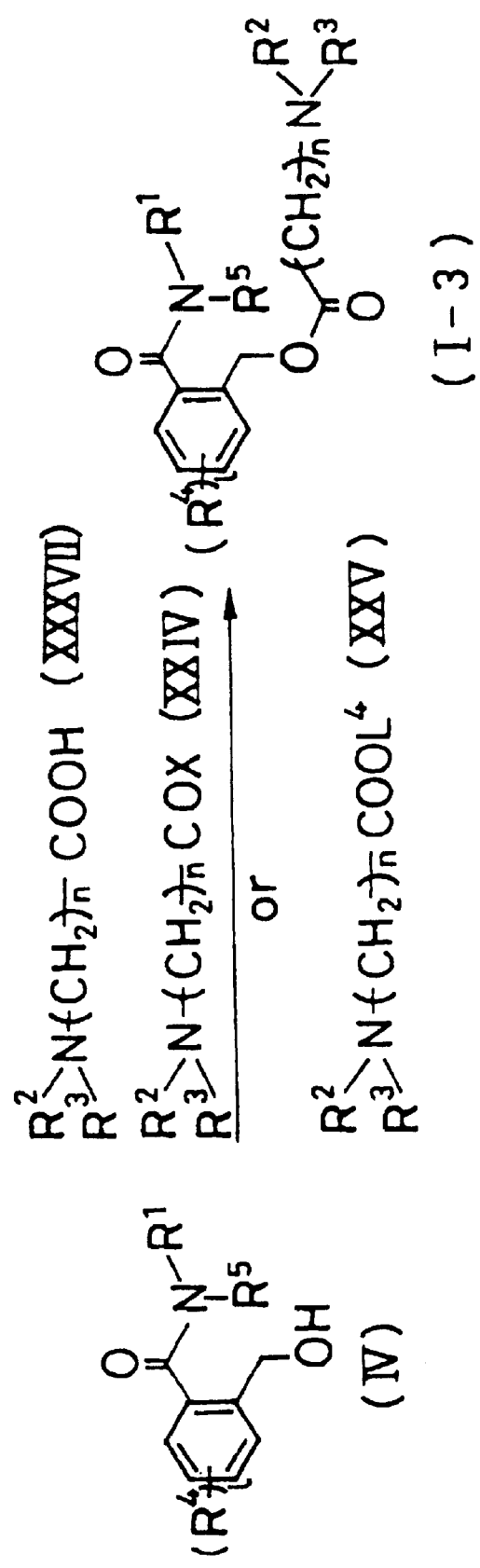

Compound (I-3) of the present invention can be synthesized, as shown in Reaction Formula CA of FIG. 7, by acylating a hydroxyl group of Compound (IV). A dehydrating condensation reaction of Compound (IV) with a carboxylic acid (XXXVII), a reaction with an acid halide (XXIV), an ester interchange reaction with an ester (XXV), or the like can be used therefor.

As for the dehydrating condensation reaction with the carboxylic acid (XXXVII), a method that the both compounds are directly reacted in the presence of an acidic catalyst, a method that the carboxylic acid (XXXVII) is converted into an active ester derivative and then the active ester is reacted with Compound (IV), or the like can be used. In the former method, as an acidic catalyst, a mineral acid such as hydrochloric acid, sulfuric acid, or boric acid, an organic acid such as aromatic sulfonic acid, a Lewis acid such as boron fluoride-etherate, or the like can be used. As a solvent, an aromatic compound such as benzene, toluene, or xylene; an ether such as tetrahydrofuran or 1,4-dioxane; an amide such as N,N-dimethylformamide or N,N-dimethylacetamide; a halogenated hydrocarbon such as dichloromethane or chloroform; or the like can be used. While the reaction temperature and reaction time may be changed according to the material compounds used, the reaction is usually effected at a temperature within the range of 0° C. to the reflux temperature of the solvent. Specifically, for example, concentrated sulfuric acid is added to a solution of Compound (IV) and the carboxylic acid (XXXVII) in dichloroethane and then reaction is effected at a temperature within the range of room temperature to the reflux temperature of the solvent, thereby attaining the aimed object. Also, a mixture of Compound (IV), the carboxylic acid (XXXVII) and boron trifluoride-etherate is reacted at a temperature within the range of room temperature to the reflux temperature of the solvent, thereby attaining the aimed object.

In the latter method proceeding by way of the active ester of the carboxylic acid (XXXVII), by using trifluoroacetic acid anhydride, N,N-dicyclohexylcarbodiimide (DCC) or the like, the carboxylic acid (XXXVII) is converted into its corresponding active ester and then the active ester is reacted with Compound (IV). As a solvent, benzene, tetrahydrofuran, N,N-dimethylformamide, dichloromethane or the like can be used. While the reaction temperature and reaction time may be changed according to the material compounds used, the reaction is usually effected at a temperature within the range of 0° C. to the reflux temperature of the solvent. Specifically, for example, trifluoroacetic acid anhydride is added to a solution of the carboxylic acid (XXXVII) in benzene at a temperature within the range of 0° C. to room temperature to convert the carboxylic acid (XXXVII) to its active ester and then the latter is reacted with Compound (IV), thereby attaining the aimed object.

The reaction with acid halide (XXIV) can be usually effected in the presence of a base. As a base, for example, an inorganic base such as sodium hydroxide or potassium hydroxide; or an organic base such as pyridine, dimethylaniline, or triethylamine can be used. As a solvent, benzene, tetrahydrofuran, 1,4-dioxane, N,N-dimethylformamide, or the like can be used. While the reaction temperature and reaction time may be changed according to the material compounds used, the reaction is usually effected at a temperature within the range of 0° C. to the reflux temperature of the solvent.Specifically, for example, acid halide (XXIV) is added to a solution containing Compound (IV) and pyridine in dichloromethane and then the reaction is effected at a temperature within the range of 0° C. to room temperature, thereby attaining the aimed object. Also, sodium hydroxide aqueous solution is dropwise added to a mixture of Compound (IV) and acid halide (XXIV), thereby attaining the aimed object.

In the ester interchange reaction with the ester (XXV), as a catalyst, an acid such as sulfuric acid or p-toluenesulfuric acid, or a base such as potassium alkoxide or titanium (IV) alkoxide can be used. The reaction can be effected with or without a solvent. In this reaction, it is preferable that either Compound (IV) or the ester (XXV) is used excessively, or that an alcohol L$^4$OH produced during the reaction is removed from the reaction system. As a solvent, benzene, toluene, tetrahydrofuran, 1,4-dioxane, N,N-dimethylformamide, dichloromethane or the like can be used. While the reaction temperature and reaction time may be changed according to the material compounds used, the reaction is usually effected at a temperature within the range of 0°C. to 200° C. and, preferably, room temperature to the reflux temperature of the solvent. Specifically, for example, titanium(IV) alkoxide is added to a solution containing Compound (IV) and the ester (XXV) in benzene and then the reaction is effected at a temperature within the range of room temperature to the reflux temperature of the solvent, thereby attaining the aimed object. As for L$^4$ of the ester (XXV), any of groups can be used if they form esters normally used for this ester interchange reaction. Examples of $L^4$ include an alkyl group such as methyl or ethyl group. The definition of $L^4$ throughout the rest of this specification remains the same.

Figure 8:
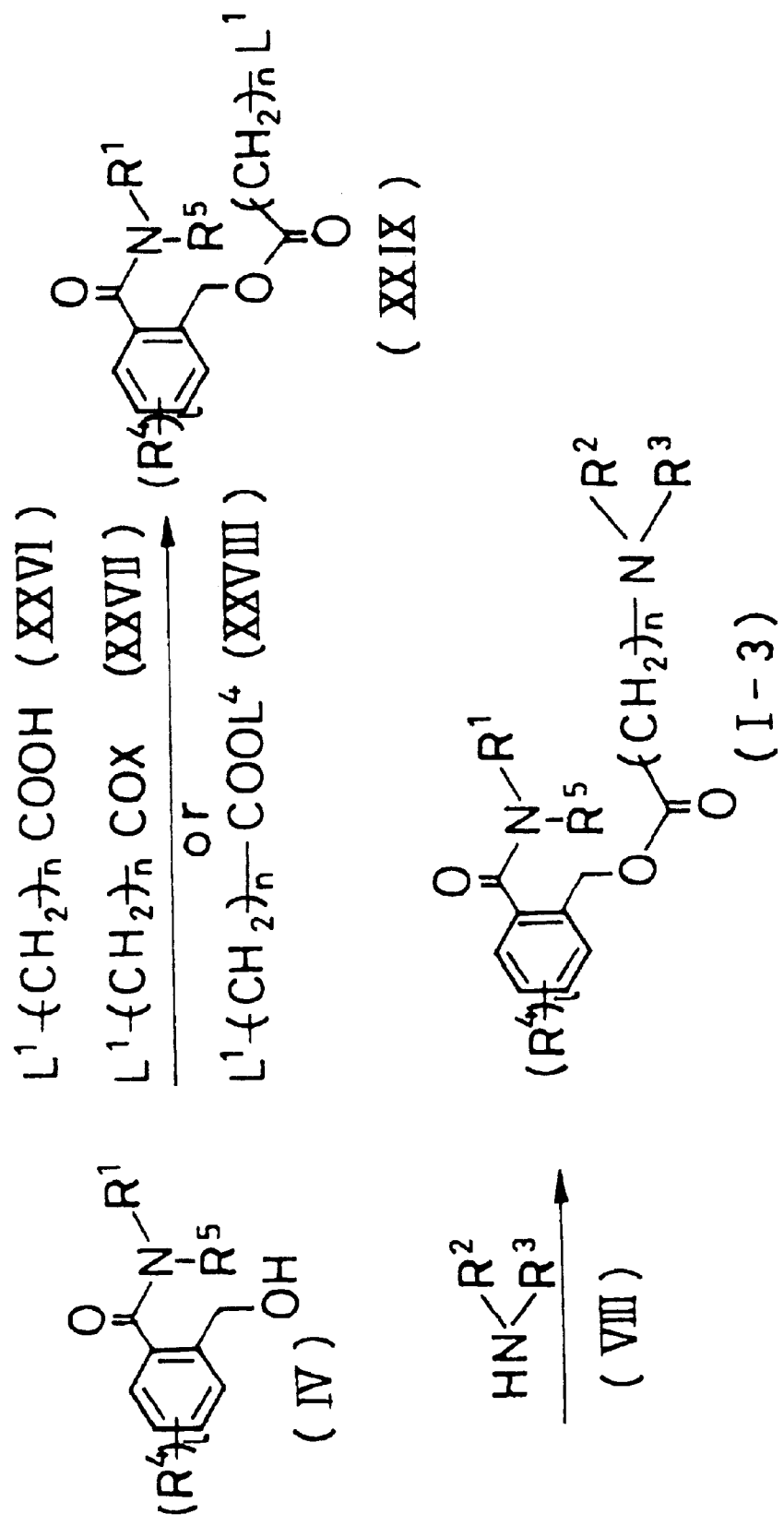

Also, Compound (I-3) can be synthesized as shown in Reaction Formula CB of FIG. 8. First, a hydroxyl group of Compound (IV) is acylated to produce Compound (XXIX). Then, Compound (XXIX) is reacted with an amine (VIII), thereby producing Compound (I-3). The first step in this Reaction Formula CB can be effected according to Reaction Formula CA. The second step can be effected according to the second step in Reaction Formula AB.

Figure 9:
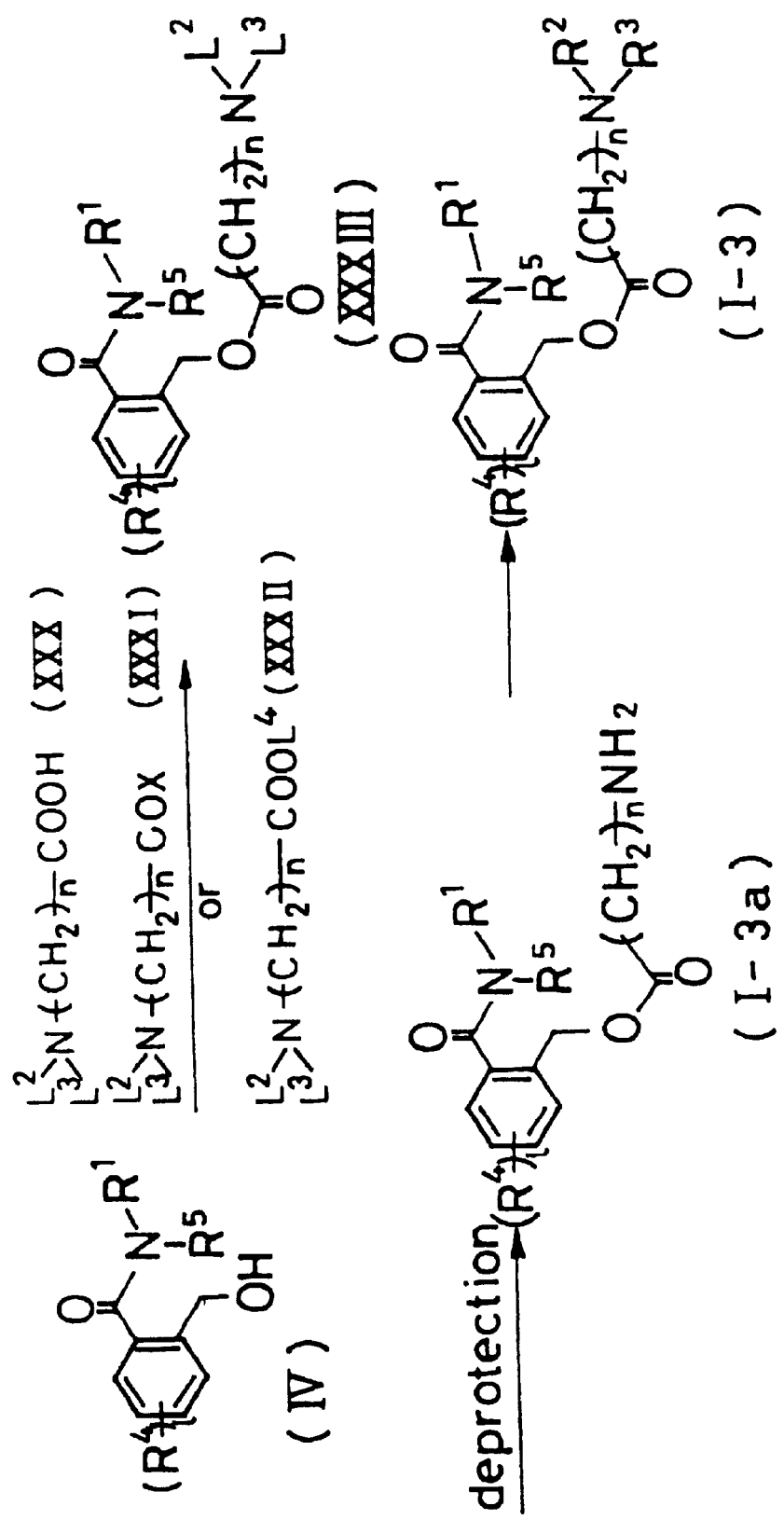

Also, Compound (I-3a) wherein $R^2$ and $R^3$ in Compound (I-3) are hydrogen atoms can be synthesized as shown in Reaction Formula CC of FIG. 9. First, a hydroxyl group of Compound (IV) is acylated to produce Compound (XXXIII). Then, Compound (XXXIII) is deprotected, thereby producing Compound (I-3a). The acylation reaction at the first step in Reaction Formula CC can be effected according to Reaction Formula CA. The deprotection at the second step in Reaction Formula CC can be effected according to the reaction of the second step in Reaction Formula AC. Further, in the similar manner to Reaction Formula AD, Compound (I-3a) can be converted into Compound (I-3).

Compound (I-4)
($A=R^1$, $B=$—$(CH_2)n\text{-}NR^2R^3$, $Z=$—$NR^6$—)

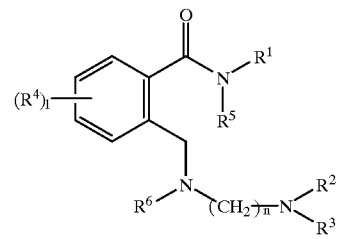

(I-4)

Figure 10:
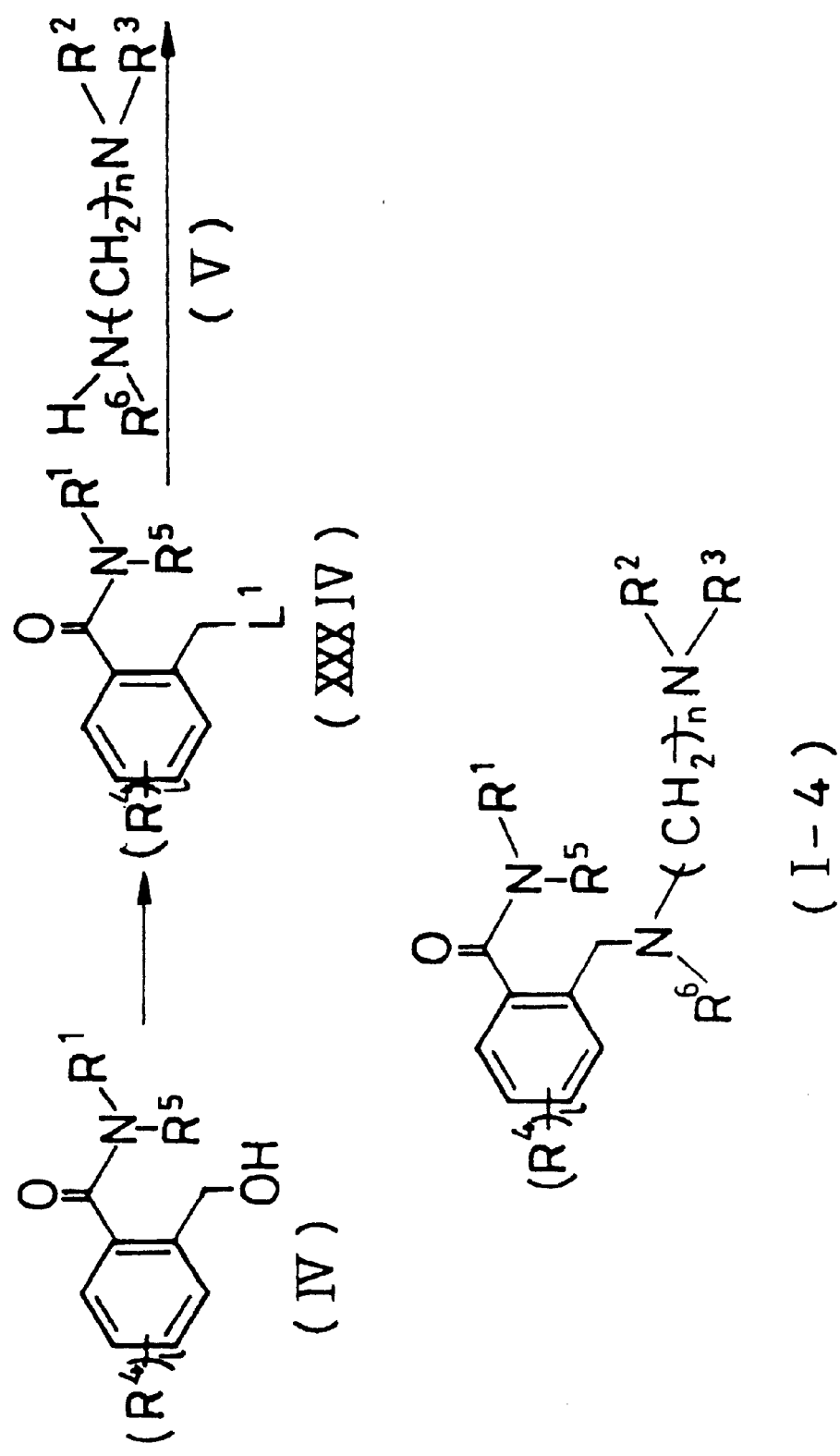

Compound (I-4) of the present invention can be synthesized as shown in Reaction Formula DA in FIG. 10. Namely, a hydroxyl group of Compound (IV) is substituted with $L^1$, wherein $L^1$ is an atom or a group which can be easily substituted with nitrogen atom, to produce Compound (XXXIV). Then, Compound (XXXIV) is reacted with an amine (V), thereby producing Compound (I-4).

At the first step in Reaction Formula DA, when $L^1$ is a halogen atom, phosphorus pentachloride, phosphorus trichloride, thionyl chloride or the like can be used therefor. As an additive, for example, an organic base such as triethylamine, pyridine or N-methylmorpholine can be used. As a solvent, for example, a halogenated hydrocarbon such as dichloromethane or chloroform; an aromatic compound such as benzene, toluene, xylene, or pyridine; an ether such as diethyl ether, tetrahydrofuran or 1,4-dioxane; an amide such as N,N-dimethylformamide or N,N-dimethylacetamide; an sulfoxide such as dimethyl sulfoxide; or a mixed solvent thereof can be used. While the reaction temperature and reaction time may be changed according to the material compounds used, the reaction is usually effected at a temperature within the range of 0° C. to the reflux temperature of the solvent.

When $L^1$ is a group such as tosyloxy or mesyloxy, the reaction can be effected by reacting Compound (IV) with p-toluenesulfonyl chloride, methanesulfonyl chloride, or the like in the presence of a base such as pyridine. Specifically, for example, a solution containing Compound (IV) and p-toluenesulfonyl chloride in 1,4-dioxane is added to sodium hydroxide aqueous solution at a temperature within the range of 0°C. to room temperature, thereby attaining the aimed object.

The second step in Reaction Formula DA can be effected according to the reaction at the second step in Reaction Formula AB.

Also, Compound (I-4a) wherein $R^2$ and $R^3$ in Compound (I-4) are hydrogen atoms can be synthesized as shown in Reaction Formula DB of FIG. 11. First, Compound (XXXIV) is reacted with an amine (XXXV) to produce Compound (XXXVI). Then, Compound (XXXVI) is deprotected, thereby producing Compound (I-4a). The first step of Reaction Formula DB can be effected according to the reaction at the second step in Reaction Formula DA. The deprotection at the second step of Reaction Formula DB can be effected according to the reaction of the second step in Reaction Formula AC. Further, in the similar manner to Reaction Formula AD, Compound (I-4a) can be converted into Compound (I-4).

Compound (I-5)
($A=$—$(CH_2)n\text{-}NR^2R^3$, $B=R^1$, $Z=$—$OCONR^6$—)

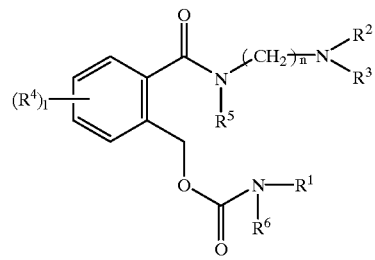

(I-5)

Figure 12:
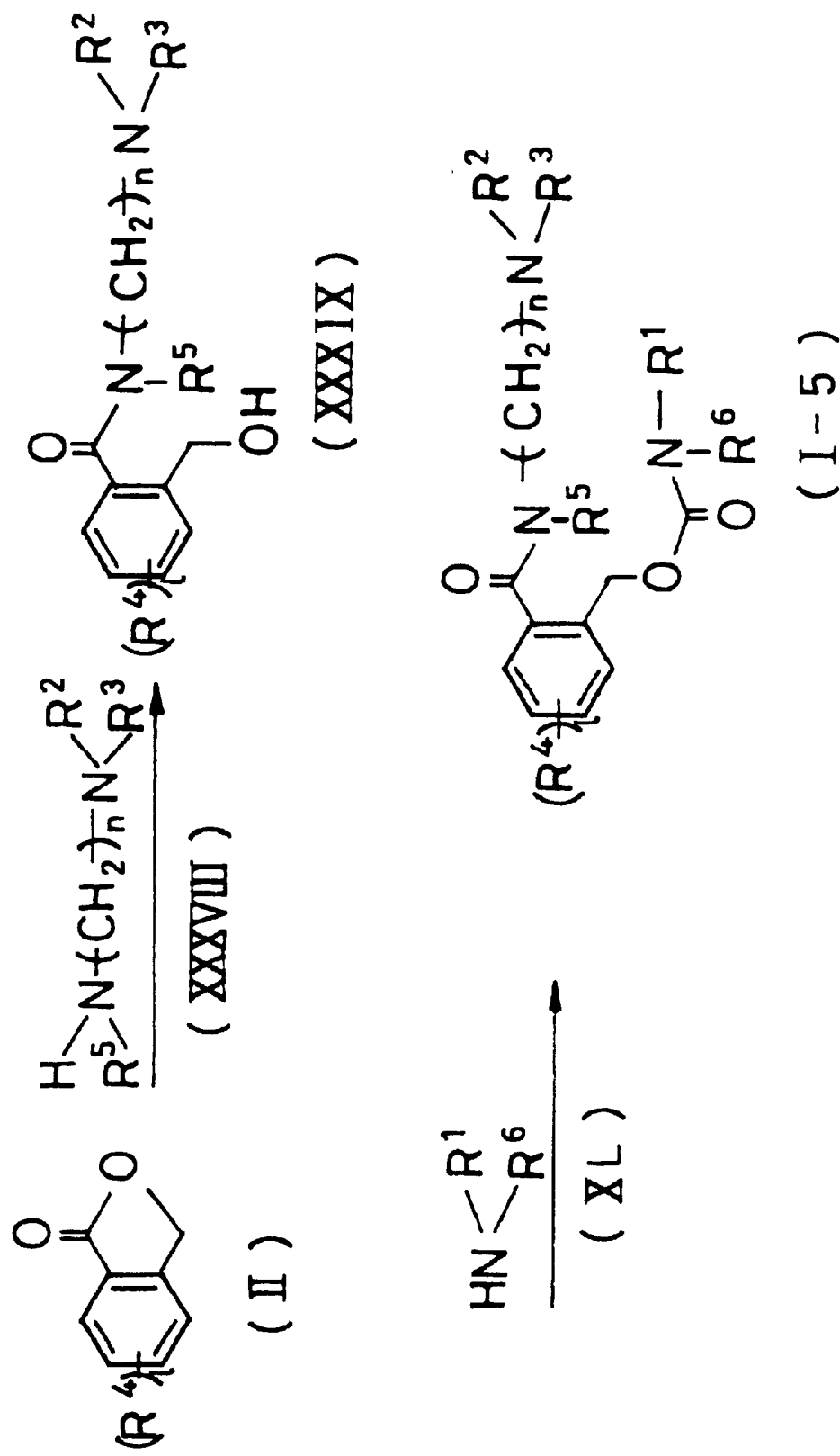

Compound (I-5) of the present invention can be synthesized as shown in Reaction Formula EA in FIG. 12. First, phthalide (II) is reacted with an amine (XXXVIII) to produce Compound (XXXIX). Then, Compound (XXXIX) is reacted with an amine (XL), thereby producing Compound (I-5). The first and second steps in this Reaction Formula EA can be effected according to the reactions at the first and second steps in Reaction Formula AA, respectively.

Figure 13:
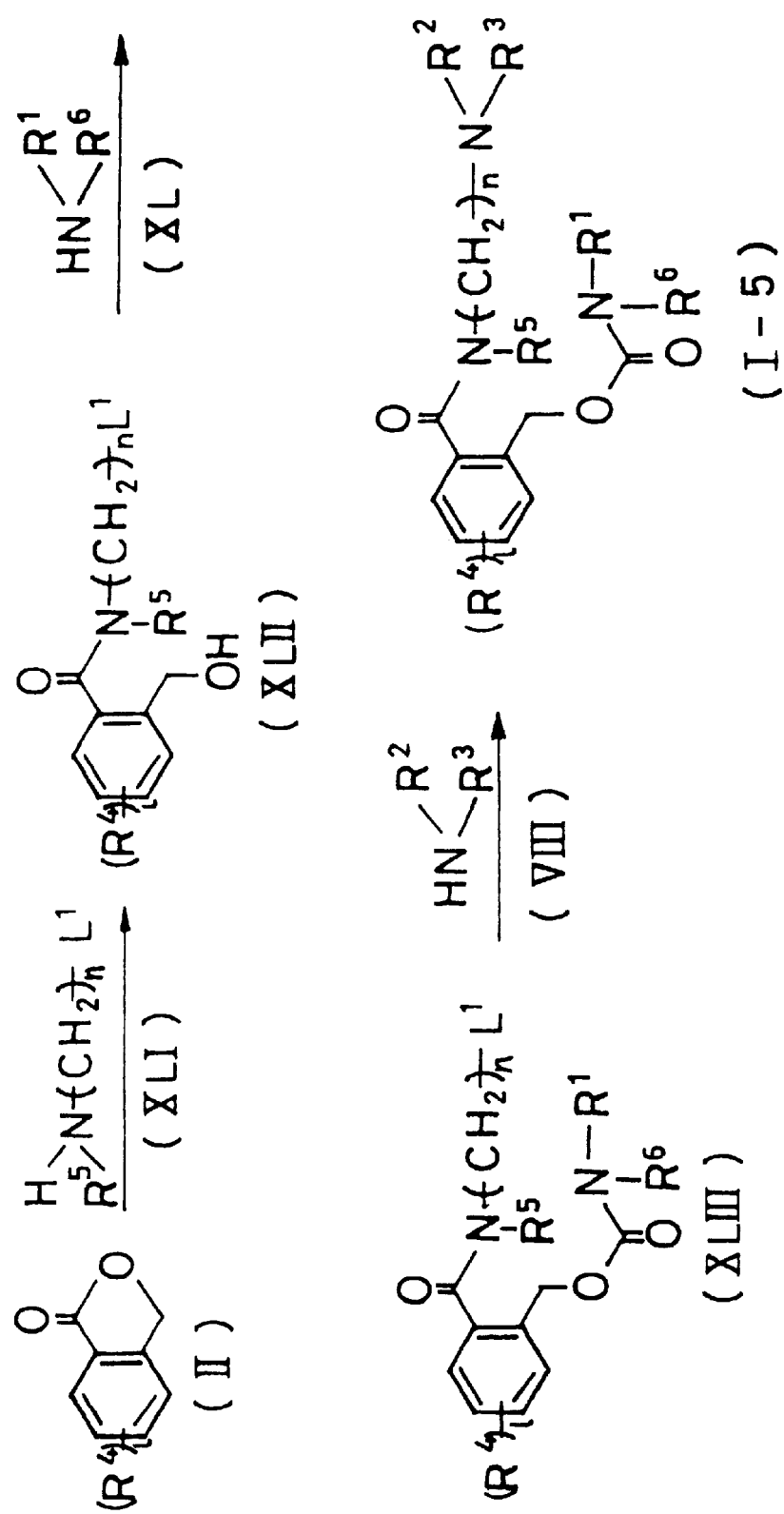

Also, Compound (I-5) can be synthesized as shown in Reaction Formula EB of FIG. 13. First, Compound (XLII) is synthesized from phthalide (II). Second, Compound (XLII) is reacted with an amine (XL) to produce Compound (XLIII). Finally, Compound (XLIII) is reacted with an amine (VIII), thereby producing Compound (I-5).

The first and second steps in Reaction Formula EB can be effected according to the reactions at the first and second steps in Reaction Formula AA, respectively. The third step in Reaction Formula EB can be effected according to the reaction at the second step in Reaction Formula AB.

Figure 14:
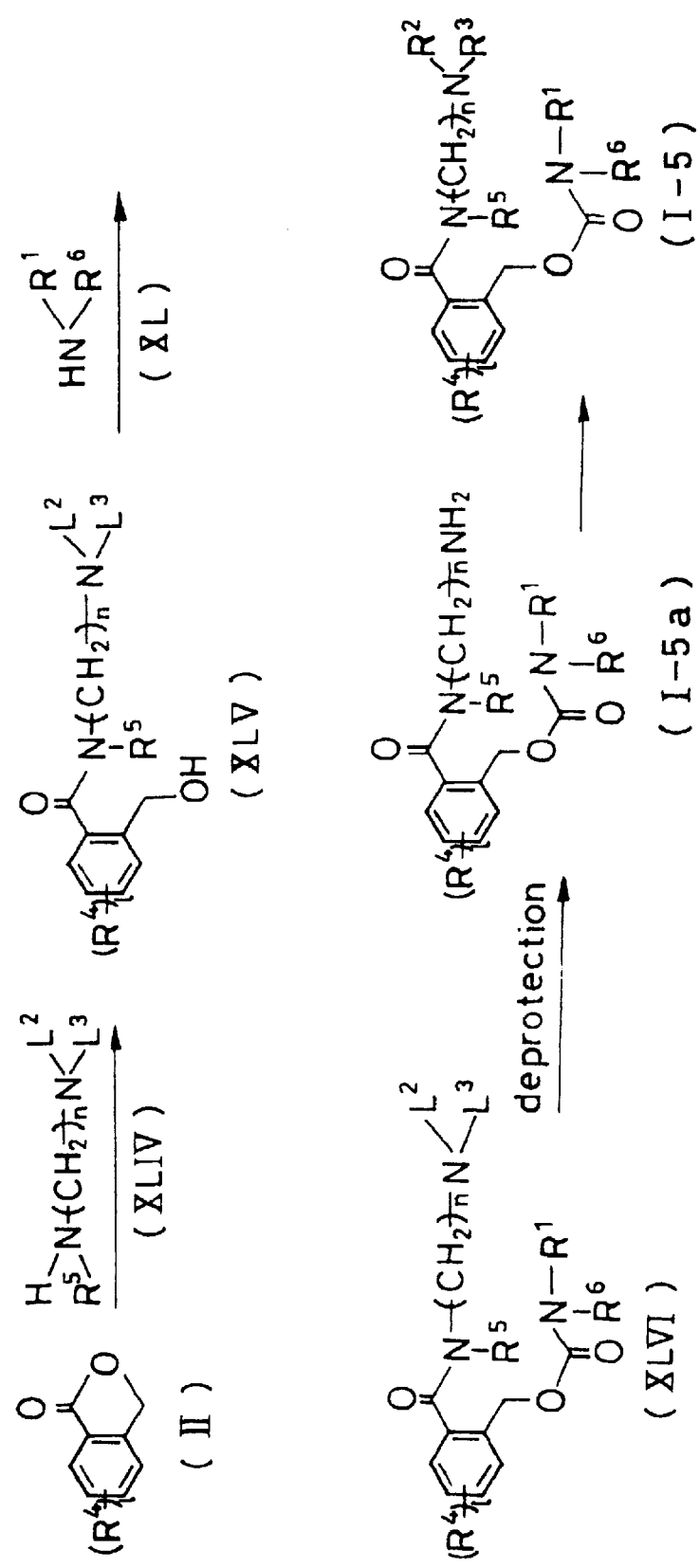

Also, Compound (I-5a) wherein $R^2$ and $R^3$ in Compound (I-5) are hydrogen atoms can be synthesized as shown in Reaction Formula EC of FIG. 14. First, Compound (XLV) is synthesized from phthalide (II). Second, Compound (XLV) is reacted with the amine (XL) to produce Compound (XLVI). Finally, Compound (XLVI) is deprotected, thereby producing Compound (I-5a). The first and second steps in Reaction Formula EC can be effected according to the reactions at the first and second steps in Reaction Formula AA, respectively. The deprotection at the third step of Reaction Formula EC can be effected according to the reaction of the second step in Reaction Formula AC. Further, in the similar manner to Reaction Formula AD, Compound (I-5a) can be converted into Compound (I-5).

Compound (I-6)
(A=—(CH$_2$)n-NR$^2$R$^3$, B=R$^1$, Z=—O—)

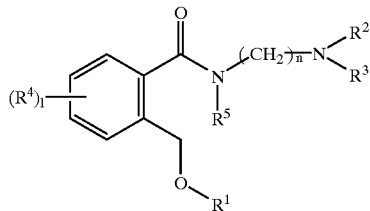

(I-6)

Figure 15:
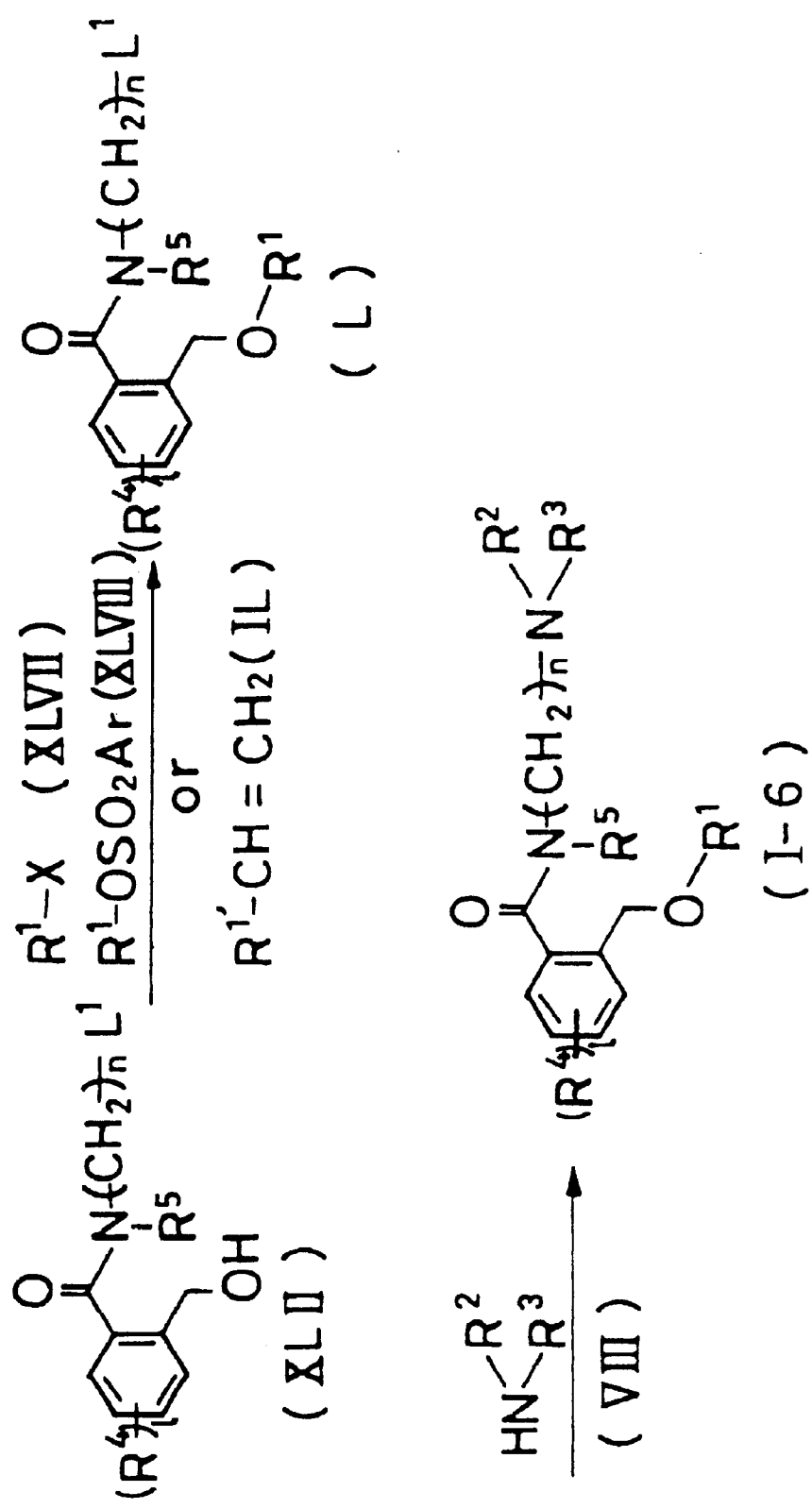
Figure 16:
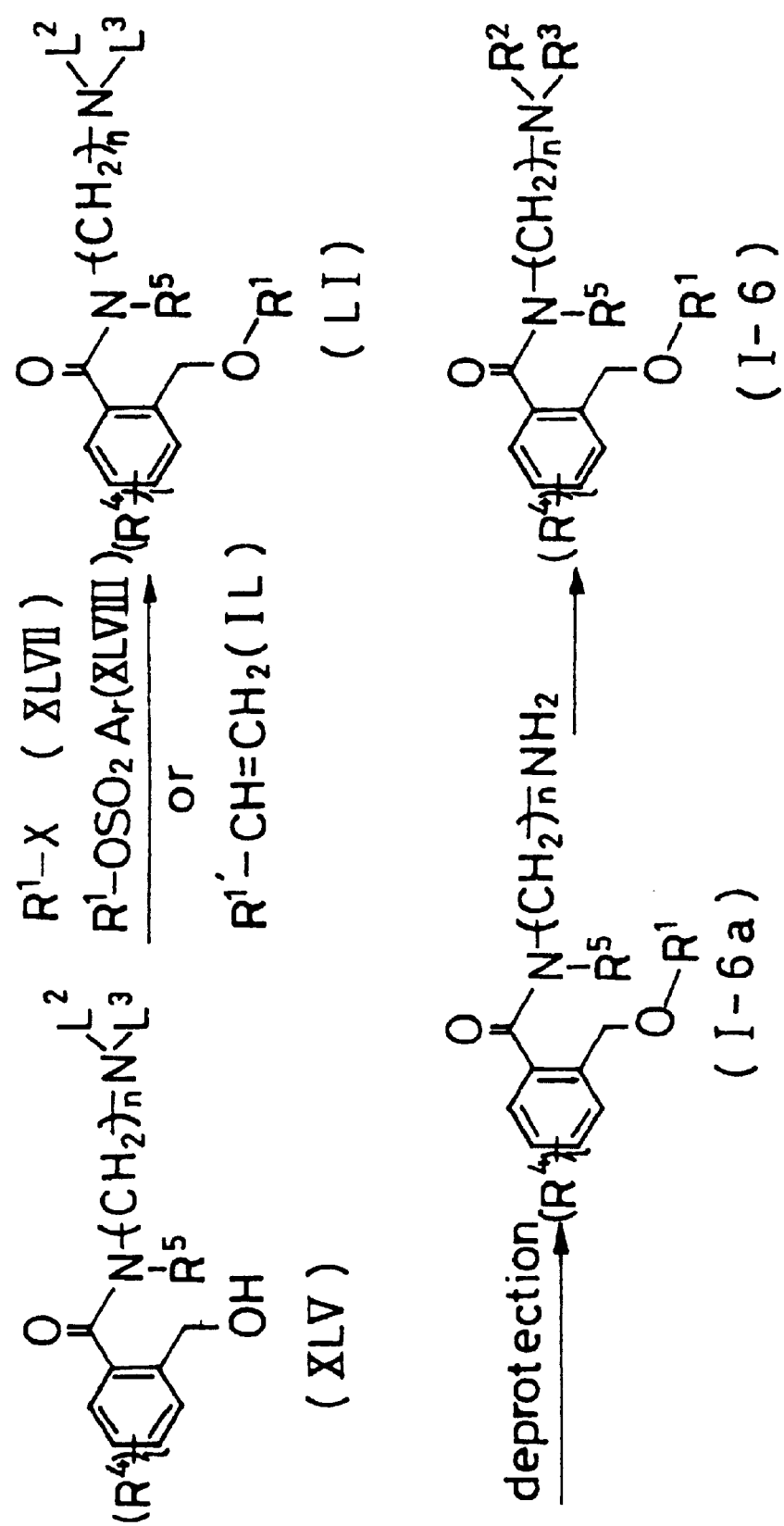

Compound (I-6) of the present invention can be synthesized as shown in Reaction Formula FA or FB of FIG. 15 or 16. These Reaction Formnulas can be effected according to Reaction Formulas BA and BB, respectively.

R$^{1'}$ in an alkene (IL) can be selected in order that this alkene (IL) corresponds to R$^1$. For example, when R$^1$ is octadecyl group, R$^{1'}$ represents hexadecyl group.

Compound (I-7)
(A=—(CH$_2$)n-NR$^2$R$^3$, B=R$^1$, Z=—OCO—)

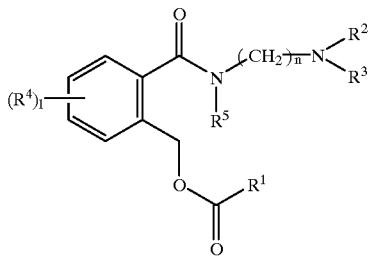

(I-7)

Figure 17:
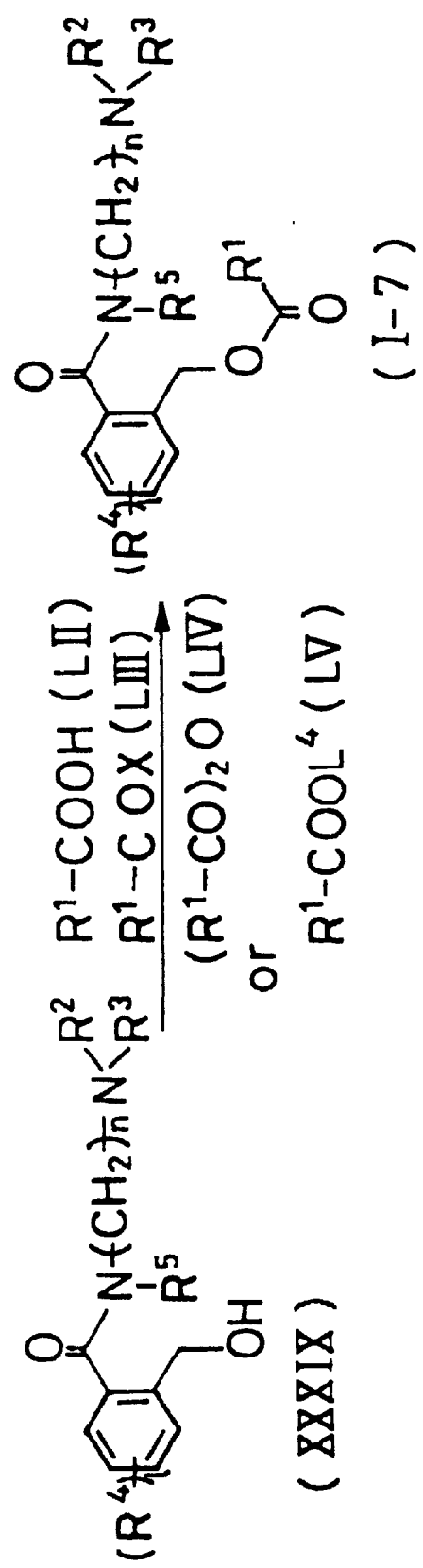
Figure 18:
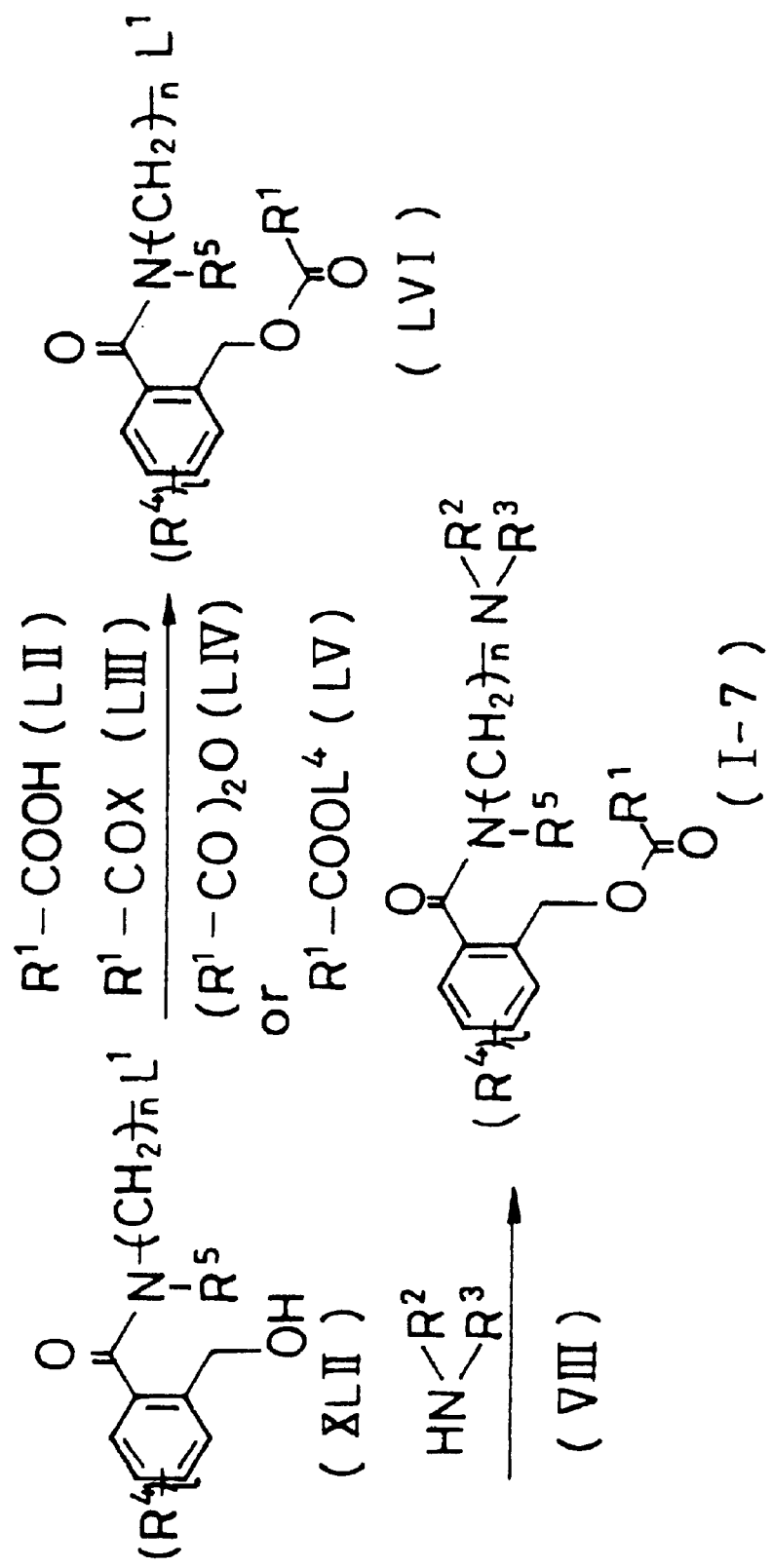
Figure 19:
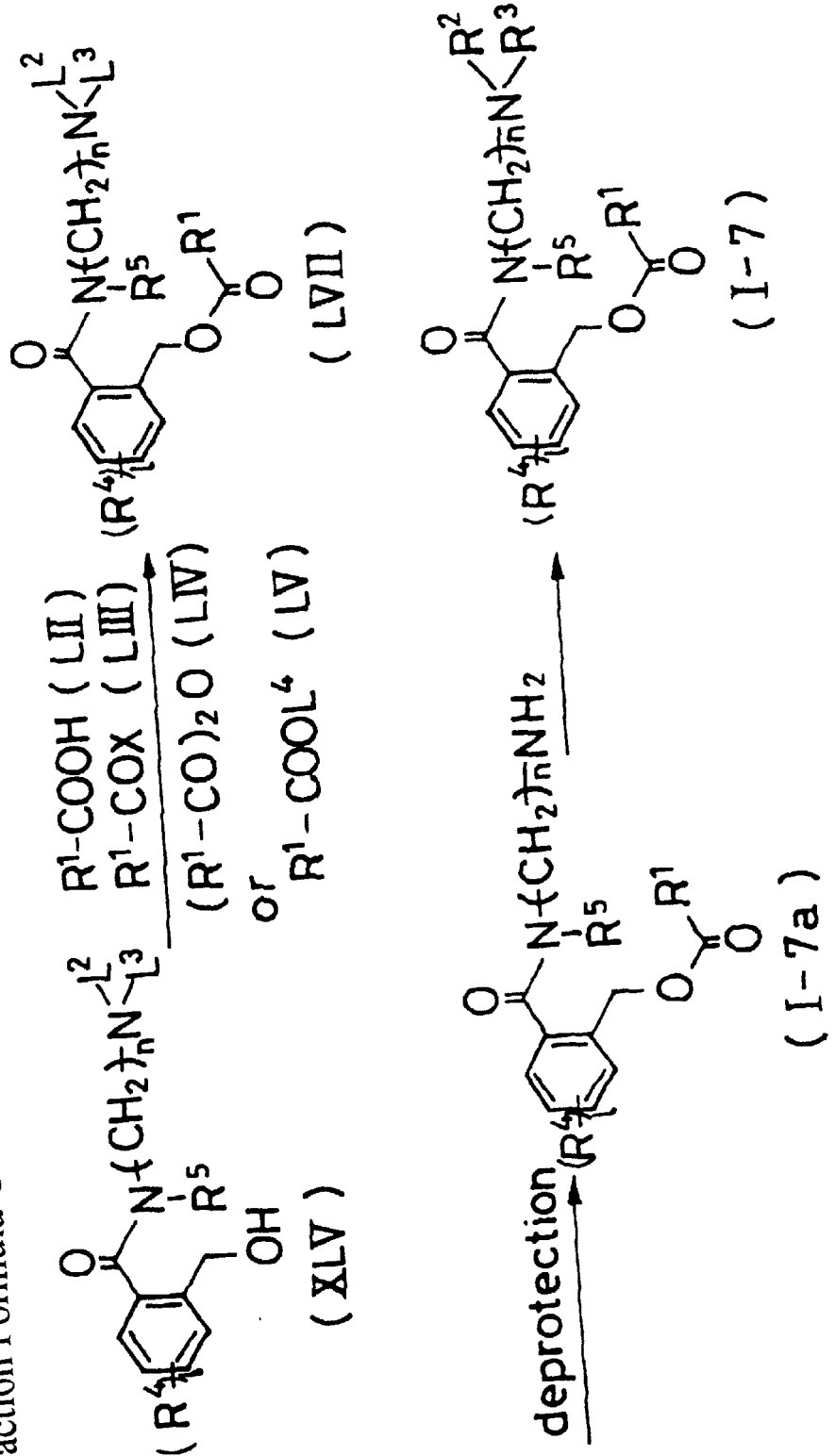

Compound (I-7) of the present invention can be synthesized as shown in Reaction Formulas GA to GC in FIGS. 17 to 19. These Reaction Formulas can be effected according to Reaction Formulas CA to CC, respectively.

The method using acid anhydride (LIV) can be effected in the similar manner to the case using acid halide (LIII).

Compound (I-8)
(A=—(CH$_2$)n-NR$^2$R$^3$, B=R$^1$, Z=—NR$^6$—)

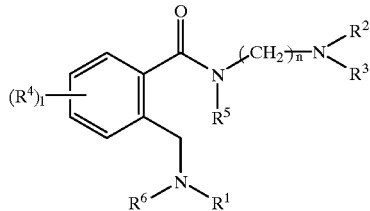

(I-8)

Figure 21:
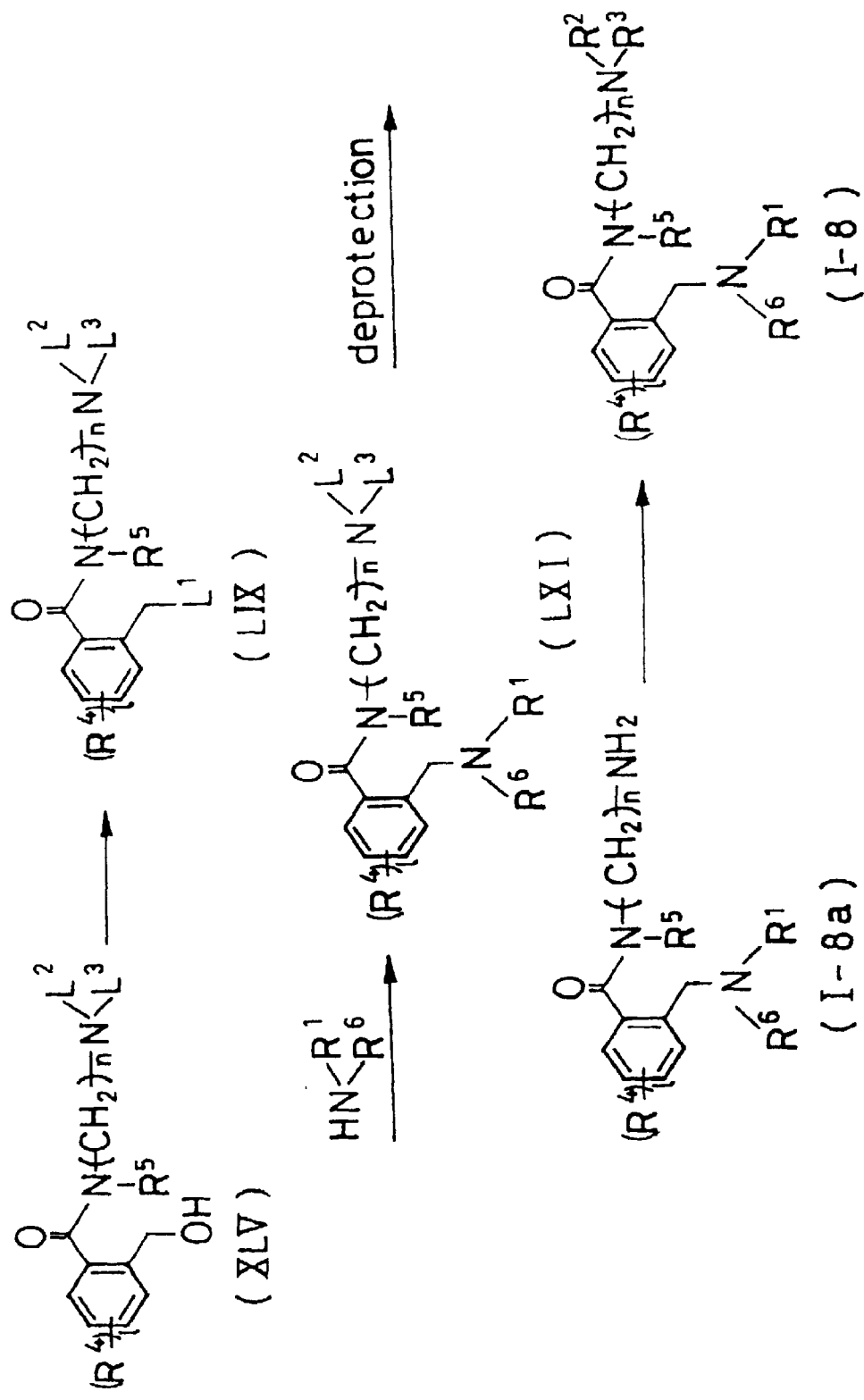

Compound (I-8) of the present invention can be synthesized as shown in Reaction Formula HA or HB of FIG. 20 or 21.

Reaction Formula HA can be effected according to Reaction Formula DA.

The first and second steps of Reaction Formula HB can be effected according to the reactions at the first and second steps in Reaction Formula DA, respectively. The third step in Reaction Formula HB can be effected according to the reaction at the second step in Reaction Formula AC. Also, in the similar manner to Reaction Formula AD, Compound (I-8a) wherein R$^2$ and R$^3$ of Compound (I-8) are hydrogen atoms can be converted into Compound (I-8).

Among the starting materials used in the foregoing Reaction Formulas, materials which are not described above are commercially available or can be easily synthesized from a suitable starting material by using known methods.

Also, according to the above Reaction Formulas, a compound wherein —CO—N(R$^5$)A in Formula (I) is —CH$_2$—CO—N(R$^5$)A can be synthesized. For example, in Reaction Formula AA, 3-isochromanone may be used in the place of phthalide (II).

The 1,2-di-substituted benzene-carboxamide derivative (I) provided in the present invention can be changed to an acid-added salt if necessary. Examples of the acid-added salt include salt with an inorganic acid such as hydrochloric acid, hydrobromic acid, sulfuric acid or phosphoric acid and salts with an organic acid such as acetic acid, propionic acid, citric acid, lactic acid, oxalic acid, maleic acid, fumaric acid, succinic acid, tartaric acid or methanesulfonic acid. These salts can be easily manufactured by common methods.

The 1,2-di-substituted benzene-carboxamide derivatives in accordance with the present invention, which mechanism of action has not been made clear, have an excellent hair growth and regrowth promoting effect. Accordingly, by applying the compound on skin of mammals such as human scalp, care, improvement, or prevention of hair loss can be expected.

The 1,2-di-substituted benzene-carboxamide derivative of the present invention can apply to pathological alopecia such as alopecia areata, alopecia pityrodes or alopecia seborrheica in addition to thin hair or hair loss what is called male pattern baldness or androgenic alopecia. The dosage of the 1,2-di-substituted benzene-carboxamide derivative in accordance with the present invention must be determined suitably according to sex, age and degree of symptom in hair loss or thin hair. Usually 0.01–20 mg/cm$^2$ is applied on scalp per day for an adult in a single dose or several doses.

When the 1,2-di-substiltuted benzene-carboxamide derivative of the present invention is used as a drug, quasi-drug or cosmetic for hair growth and regrowth promoting and prevention of hair loss, its pharmaceutical form can be selected voluntarily as long as the effects of the present invention can be exhibited. Examples of the pharmaceutical forms include tonic, lotion, milky lotion, cream, ointment, gel, spray and mousse.

In addition to the 1,2-di-substituted benzene-carboxamide derivative in accordance with the present invention, various pharmaceutically acceptable ingredients, which are generally compounded to hair growth promoting composition in the field of drug, quasi-drug and cosmetic, can be compounded to these preparations.

For example, as a drug having a blood flow promoting action, swertia herb extract, vitamin E and derivatives thereof, nicotinates such as benzyl nicotinate, and the like can be used. Examples of drugs which promote blood circulation by topical stimulation include capsicum tincture, cantharides tincture, camphor and vanillic acid nonylamide. Examples of drugs having hair follicle activating action include hinokitiol, placental extract, photosensitizing dye, pantothenic acid and derivatives thereof. Examples of drugs having antiandrogen action include a hormone such as estradiol or estrone. Examples of drugs having antiseborrheic action include sulfur, thioxolone and vitamin B$_6$.

In addition, salicylic acid, resorcine and the like which has corneocycle desquamating and antibacterial action can be compounded therein so as to prevent the generation of dandruff. Also, glycyrrhizic acid and derivatives thereof, menthol, and the like can be compounded therein so as to prevent inflammation of scalp. Further, an amino acid such as serine, methionine or arginine, a vitamin such as biotin, extracts of crude drugs and the like can be compounded therein in order to supplement nutrition for hair follicle and activate enzyme activity.

Also, extracts from plants such as althea, coix, peppermint, leaf base, capsicum, aloe, lycium, mugwort, oryza, seashore vitex, rosmarinus officinalis, drynaria, cytisus scoparius, gentiana, salviae miltiorrhizeae radix, sponge gourd, platycodon, pinus, sophora root, Japanese angelica root, safflower, Japanese barberry, areca, eucalyptus, prunella spike, akebia stem, achyranthes root, bupleurum root, tea, licorice, hop, Chrysanthemum, senega, sesame, cnidium rhizome, cashew, pueraria root, rosae rugosae flos, saffron, rosemary, rehmannia root, or mallow can be compounded.

Also, a vasodilator such as alkoxycarbonylpyridine N-oxide, carpronium chloride or acetylcholine derivative; a cutaneous hyperfunctioning agent such as cephalanthin; an antibacterial agent such as hexachlorophene, benzalkonium chloride, cetylpyridinium chloride, undecylenic acid, trichlorocarbanilide or bithionol; zinc and its derivatives; lactic acid and its alkyl ester; an organic acid such as citric acid; a protease inhibitor such as tranexamic acid; and the like can be compounded.

Further, an alcohol such as ethanol or isopropyl alcohol; a polyvalent alcohol such as glycerine, propylene glycol or polyethylene glycol; an oily ingredient such as higher fatty acids, higher alcohols, hydrogenated castor oils, natural oils and fats, ester oils or silicone oils; surfactants; perfumes; chelating agents; humectants such as 1,3-butyleneglycol, hyaluronic acid and its derivatives, maltitol, soluble collagen or sodium lactate; thickening agents such as quince mucilage, carboxyvinylpolymer or xanthan gum; antioxidants; ultraviolet absorbers: coloring agents; water; stabilizers; and the like, which are generally compounded in hair growth composition, can be compounded within the range provided that the effects of the present invention are not spoiled.

EXAMPLES

In the following, the present invention will be explained by using specific examples. However, the present invention should not be restricted thereto.

Hair Regrowth Test (1) Test Method

By using C3H/HeNCrj mice, whose hair cycle was in resting stage, the experiment was performed according to the method of Ogawa et. al. (Normal and Abnormal Epidermal Differentiation, Edited by M. Seiji and I. A. Bernstein, Pages 159–170, 1982, Todai Shuppan). 10 mice were used in a group and the mice's hair within the area of 3×4 cm of the regions of back was shaved by a clipper and a shaver. 0.1 ml of ethanol (negative contrast) or ethanol solution of the tested compound was applied on the shaved portion once a day. For hair regrowth effect of the tested compound, the hair regrowth area of mice's region of back was measured and ratio of the hair regrowth area with respect to the shaved area was evaluated as hair regrowth area rate.

(2) Result

Hair regrowth area rates (%) after the following tested compounds were applied for 18–25 days are shown in TABLE 1:

Compound 2: [2-[[N-[3-(Dimethylamino)propyl] carbamoyloxy]methyl]phenyl]-N-octadecylformamide

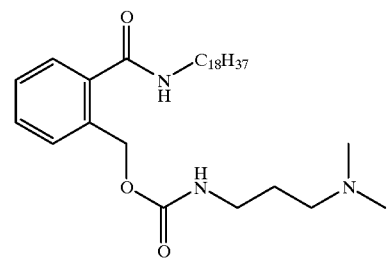

Compound 3: [2-[[N-[3-(Dimethylamino)propyl] carbamoyloxy]methyl]phenyl]-N-octadecylformamide hydrochloride

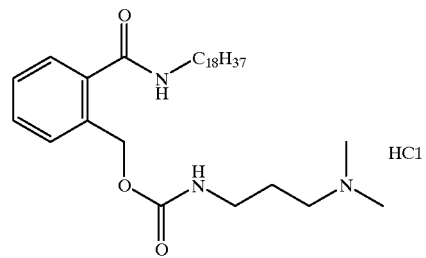

Compound 4: [2-[[N-[3-(Dimethylamino)propyl] carbamoyloxy]methyl]phenyl]-N-hexadecylformamide

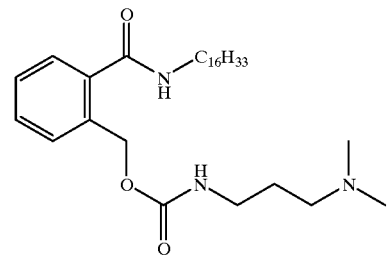

Compound 6: [2-[[N-[3-(Dimethylamino)propyl] carbamoyloxy]methyl]phenyl]-N-tetradecylformamide

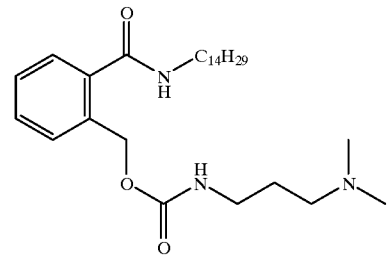

Compound 12: [2-[[N-(3-Morpholinopropyl)carbamoyloxy] methyl]phenyl]-N-octadecylformamide

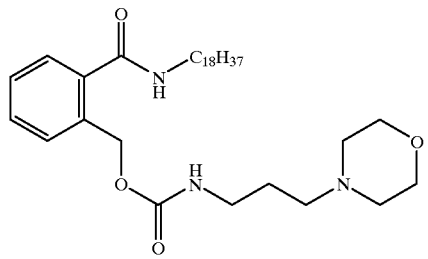

Compound 14: [2-[[N-[2-(Dimethylamino)ethyl] carbamoyloxy]methyl]phenyl]-N-octadecylformamide

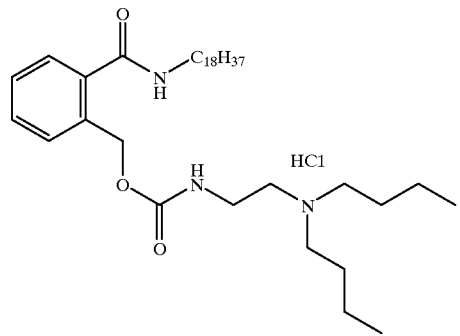

Compound 29: [2-[[N-[2-(Diethylamino)ethyl] carbamoyloxy]methyl]phenyl]-N-octadecylformamnide hydrochloride

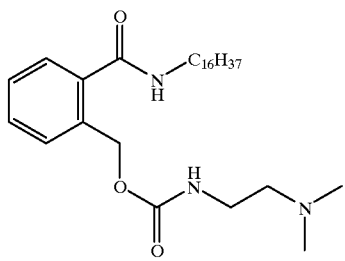

Compound 15: [2-[[N-[2-(Dimethylamino)ethyl] carbamoyloxy]methyl]phenyl]-N-octadecylformamide hydrochloride

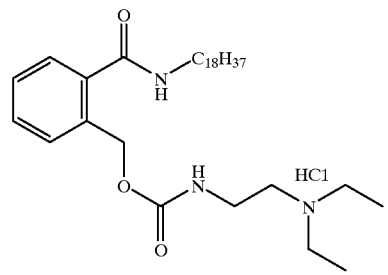

Compound 31: [2-[[N-[2-(Diisopropylamino)ethyl] carbamoyloxy]methyl]phenyl]-N-octadecylformamide hydrochloride

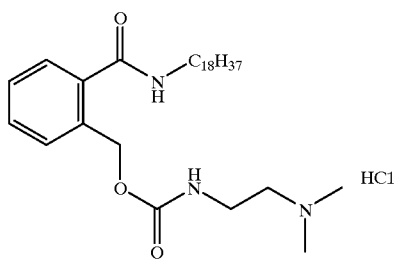

Compound 22: N-[3-(Dimethylamino)propyl]-{2-[(N-octadecylcarbamoyloxy)methyl]phenyl}formamide

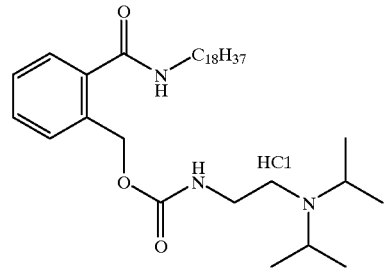

Compound 34: [2-(N-octadecylcarbamoyl)phenyl]methyl-4-methylpiperazinecarboxylate

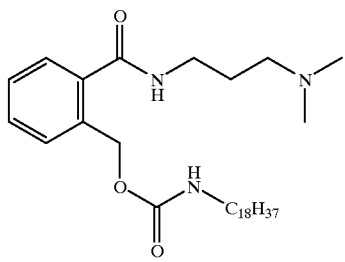

Compound 27: [2-[[N-[2-(Dibutylamino)ethyl] carbamoyloxy]methyl]phenyl]-N-octadecylformamide hydrochloride

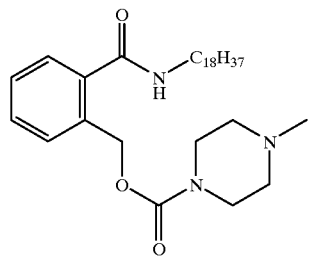

Compound 35: [2-(N-Octadecylcarbamoyl)phenyl]methyl-4-methylpiperazinecarboxylate hydrochloride

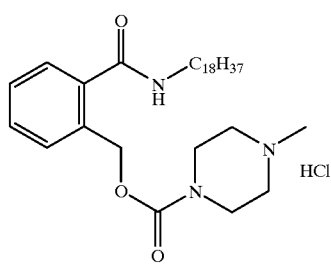

Compound 37: [2-(N-Octadecylcarbamoyl)phenyl]methyl-4-(2-hydroxyethyl)piperazinecarboxylate hydrochloride

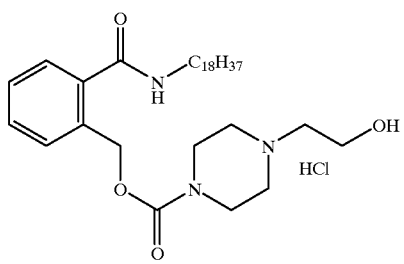

Compound 38: [[2-[(4-Methylpiperazinyl)carbonyl]phenyl]methoxy]-N-octadecylformamide

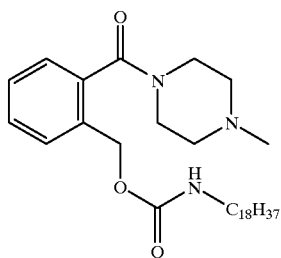

Compound 39: [[2-[(4-Methylpiperazinyl)carbonyl]phenyl]methoxy]-N-octadecylformamide hydrochloride

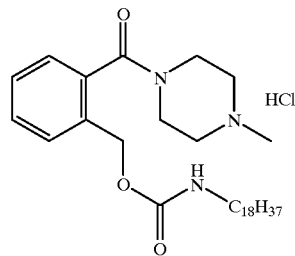

Compound 41: [2-[[N-[3-(Dibutylamino)propyl]carbamoyloxy]methyl]phenyl]-N-octadecylformamide hydrochloride

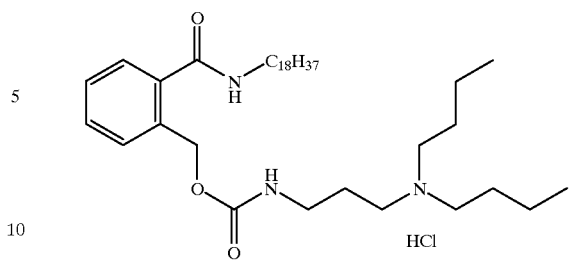

TABLE 1

| Compound | Conc. of Compd. (w/v %) | Days of Application (days) | Hair Regrowth Area Rate (%) |
| --- | --- | --- | --- |
| Ethanol (negative contrast) | — | 24 | 0 |
| Compound 2 | 0.1 | 24 | 97 |
| Compound 3 | 0.1 | 24 | 58 |
| Compound 4 | 0.1 | 24 | 89 |
| Compound 6 | 0.2 | 24 | 85 |
| Compound 12 | 0.2 | 25 | 97 |
| Compound 14 | 0.1 | 24 | 100 |
| Compound 15 | 0.1 | 23 | 46 |
| Compound 22 | 0.1 | 24 | 92 |
| Compound 27 | 0.1 | 24 | 100 |
| Compound 29 | 0.1 | 24 | 85 |
| Compound 31 | 0.1 | 18 | 100 |
| Compound 34 | 0.1 | 25 | 100 |
| Compound 35 | 0.1 | 23 | 98 |
| Compound 37 | 0.1 | 24 | 18 |
| Compound 38 | 0.1 | 24 | 100 |
| Compound 39 | 0.1 | 23 | 81 |
| Compound 41 | 0.1 | 18 | 100 |

As is clear from the TABLE 1, 1,2-di-substituted benzenecarboxamide derivatives and their pharmacologically acceptable salts in accordance with the present invention show excellent hair regrowth and growth promoting effects.

In the following, examples of compounds and compositions in accordance with the present invention will be explained. However, the present invention should not be restricted thereto.

Example 1-1

[2-(Hydroxymethyl)phenyl]-N-octadecylformamide (Compound 1)

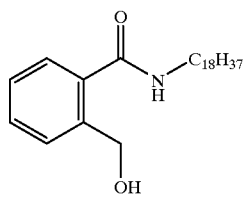

Octadecylamine (1.01 g) was added to phthalide (0.50 g). After being stirred for 10 hours at 70° C., the reaction mixture was purified by silica gel column chromatography (silica gel 20 g, chloroform:methanol=50:1), thereby yielding 1.40 g of the aimed compound as white crystals.

$^1$H-NMR (CDCl$_3$) δ:0.88 (3H, t, J=6.8 Hz), 1.2–1.4 (30H, m), 1.62 (2H, m), 3.45 (2H, td, J=7.1, 5.9 Hz), 4.42 (1H, brs), 4.60 (2H, s), 6.32 (1H, brt), 7.35 (1H, td, J=7.3, 1.5 Hz),

Example 1-2

[2-(Hydroxymethyl)phenyl]-N-octadecylformamide (Compound 1)

(1) 2-Octadecylisoindoline-1,3-dione

Phthalic anhydride (1.00 g) and octadecylamine (1.82 g) were stirred for 1 hour at 110° C. The reaction mixture was purified by silica gel column chromatography (silica gel 34 g, chloroform:methanol=20:1), thereby yielding 2.40 g of the aimed compound as white crystals.

$^1$H-NMR (CDCl$_3$) δ:0.88 (3H, t, J=6.8 Hz), 1.2–1.4 (30H, m), 1.67 (2H, m), 3.67 (2H, t, J=7.3 Hz), 7.70 (2H, dd, J=5.4, 2.9 Hz), 7.84 (2H, dd, J=5.4, 2.9 Hz).

(2) [2-(Hydroxymethyl)phenyl]-N-octadecylformamide

2-Octadecylisoindoline-1,3-dione (2.40 g) was suspended into a mixture of 2-propanol (96 ml) and water (16 ml) and then sodium borohydride (1.13 g) was added thereto at room temperature. After being stirred for 12 hours at room temperature, the reaction mixture was acidified with diluted hydrochloric acid and then concentrated. The residue, with chloroform added thereto, was washed with diluted hydrochloric acid, water, and saturated sodium hydrogencarbonate aqueous solution successively, dried over sodium sulfate anhydride, and then concentrated. The residue was purified by silica gel column chromatography (silica gel 40 g, chloroform:methanol=20:1), thereby yielding 2.35 g of product containing the aimed compound and 3-hydroxy-2-octadecylisoindoline-1-one at the ratio of 2:1 as white crystals. According to the comparison of $^1$H-NMR spectrum between this product and Compound 1 obtained by Example 1-1, it was confirmed that this product contained the aimed compound at the concentration of 60 to 70%.

Example 2

[2-[[N-[3-(Dimethylamino)propyl]carbamoyloxy] methyl]phenyl]-N-octadecylformamide (Compound 2)

Pyrdine (0.46 ml) and phenyl chlorocarbonate (0.52 ml) were added to a suspension of [2-(hydroxymethyl)phenyl]-N-octadecylformamide (1.52 g) in dichloromethane (15 ml) while being cooled with ice. After being stirred for 1 hour at room temperature, the reaction mixture, with chloroform added thereto, was washed with saturated sodium hydrogencarbonate aqueous solution and water successively, dried over sodium sulfate anhydride, and then concentrated. N,N-dimethyl-1,3-propanediamine (0.52 ml) was added to the residue. After being stirred for 14 hours at 70° C., the reaction mixture was purified by silica gel column chromatography (silica gel 50 g, chloroform:methanol=1:0–10:1), thereby yielding 1.23 g of the aimed compound as white crystals.

$^1$H-NMR (CDCl$_3$) δ:0.88 (3H, t, J=6.8 Hz), 1.2–1.4 (30H, m), 1.61 (2H, m), 1.64 (2H, m), 2.21 (6H, s), 2.34 (2H, t, J=6.3 Hz), 3.24 (2H, q, J=5.9 Hz), 3.42 (2H, td, J=7.3, 5.9 Hz), 5.21 (2H, s), 5.89 (1H, brt), 6.90 (1H, brt), 7.33 (1H, td, J=7.3, 1.5 Hz), 7.40 (1H, td, J=7.3, 1.5 Hz), 7.44 (1H, dd, J=7.3, 1.5 Hz), 7.51 (1H, dd, J=7.3, 1.5 Hz).

Example 3

[2-[[N-[3-(Dimethylamino)propyl]carbamoyloxy] methyl]phenyl]-N-octadecylformamide hydrochloride (Compound 3)

4N Hydrochloric acid—ethyl acetate solution (0.19 ml) was added to a solution of [2-[[N-[3-(dimethylamino) propyl]carbamoyloxy]methyl]phenyl]-N-octadecylformamide (0.20 g) in ethyl acetate (4 ml) while being cooled with ice. After being stirred for 10 minutes, the deposited crystals were dissolved with ethanol and the solution was concentrated. The residue was recrystallized from ethyl acetate, thereby yielding 0.21 g of the aimed compound as white crystals.

$^1$H-NMR (CDCl$_3$) δ:0.88 (3H, t, J=6.8 Hz), 1.2–1.4 (30H, m), 1.63 (2H, m), 2.03 (2H, m), 2.71 (3H, s), 2.72 (3H, s), 3.00 (2H, m), 3.33 (2H, m), 3.43 (2H, m), 5.25 (2H, s), 6.07 (1H, brs), 6.84 (1H, brs), 7.34 (1H, t, J=7.3 Hz), 7.40 (1H t, J=7.3 Hz), 7.45 (1H, t, J=7.3 Hz), 7.49 (1H, d, J=7.3 Hz), 12.07 (1H, brs).

Example 4

[2-[[N-[3-(Dimethylamino)propyl]carbamoyloxy] methyl]phenyl]-N-hexadecylformamide (Compound 4)

(1) N-Hexadecyl-[2-(hydroxymethyl)phenyl]formamide

Phthalide (2.03 g) was added to hexadecylamine (3.65 g) in argon gas atmosphere. After being stirred for 15 hours at 70° C., the reaction mixture was purified by silica gel column chromatography (silica gel 125 g, chloroform:methanol=80:1), thereby yielding 5.55 g of the aimed compound as white crystals.

$^1$H-NMR (CDCl$_3$) δ:0.88 (3H, t, J=6.8 Hz), 1.2–1.4 (26H, m), 1.63 (2H, m), 3.45 (2H, td, J=7.3, 5.9 Hz), 4.39 (1H, t, J=7.3 Hz), 4.60 (2H, d, J=7.3 Hz), 6.28 (1H, brt), 7.36 (1H, td, J=7.3, 1.5 Hz), 7.40 (1H, dd, J=7.3, 1.5 Hz), 7.45 (1H, td, J=7.3, 1.5 Hz), 7.51 (1H, d, J=7.3 Hz).

(2) [2-[[N-[3-(Dimethylamino)propyl]carbamoyloxy] methyl]phenyl]-N-hexadecyl formamide In argon gas atmosphere, pyridine (0.38 ml) and phenyl chlorocarbonate (0.44 ml) were added to a solution of N-hexadecyl-[2-(hydroxymethyl)phenyl]formamide (1.16 g) in chloroform (12 ml) while being cooled with ice. After being stirred for 2 hours at room temperature, the reaction mixture, with chloroform added thereto, was washed with 1N hydrochloric acid, saturated sodium hydrogencarbonate aqueous solution and water successively, dried over sodium sulfate anhydride, and then concentrated. In argon gas atmosphere, N,N-dimethyl-1,3-propanediamine (0.44 ml) was added to the residue. After being stirred for 2 hours at 70° C., the reaction mixture was purified by silica gel column chromatography (silica gel 50 g, chloroform:methanol=30:1–10:1), thereby yielding 1.38 g of the aimed compound as white crystals.

$^1$H-NMR (CDCl$_3$) δ:0.88 (3H, t, J=6.8 Hz), 1.2–1.4 (26H, m), 1.57–1.67 (4H, m), 2.21 (6H, s), 2.33 (2H, t, J=6.6 Hz), 3.24 (2H, m), 3.42 (2H, td, J=7.3, 5.9 Hz), 5.21 (2H, s), 5.88 (1H, brt), 6.89 (1H, brt), 7.34 (1H, td, J=7.3, 1.5 Hz), 7.40 (1H, td, J=7.3, 1.5 Hz), 7.44 (1H, dd, J=7.3, 1.5 Hz), 7.51 (1H, dd, J=7.3, 1.5 Hz).

7.39 (1H, dd, J=7.3, 1.5 Hz), 7.45 (1H, td, J=7.3, 1.5 Hz), 7.51 (1H, dd, J=7.3, 1.5 Hz).

Example 5

[2-[[N-[3-(Dimethylamino)propyl]carbamoyloxy]
methyl]phenyl]-N-hexadecylformamide
hydrochloride (Compound 5)

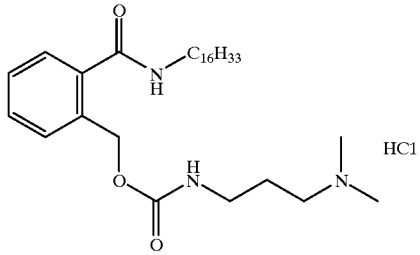

4N Hydrochloric acid—ethyl acetate solution (0.12 ml) was added to a solution of [2-[[N-[3-(dimethylamino) propyl]carbamoyloxy]methyl]phenyl]-N-hexadecylformamide (0.20 g) in ethyl acetate (2 ml) at room temperature. After being stirred for 15 minutes, the reaction mixture was concentrated. The residue was recrystallized from ethyl acetate, thereby yielding 0.19 g of the aimed compound as white crystals.

$^1$H-NMR (CDCl$_3$) δ:0.88 (3H, t, J=6.8 Hz), 1.2–1.4 (26H, m), 1.63 (2H, m), 2.03 (2H, m), 2.72 (6H, s), 3.01 (2H, m), 3.32 (2H, m), 3.42 (2H, m), 5.25 (2H, s), 6.13 (1H, brt), 6.79 (1H, brt), 7.33 (1H, t, J=7.3 Hz), 7.40 (1H, t, J=7.3 Hz), 7.45 (1H, d, J=7.3 Hz), 7.48 (1H, d, J=7.3 Hz), 12.01 (1H, brs).

Example 6

[2-[[N-[3-(Dimethylamino)propyl]carbamoyloxy]
methyl]phenyl]-N-tetradecylformamide (Compound 6)

(1) [2-(Hydroxymethyl)phenyl]-N-tetradecylformamide

Tetradecylamine (3.504 g) was added to phthalide (2.201 g) in argon gas atmosphere. After being stirred for 15.5 hours at 70° C., the reaction mixture was purified by silica gel column chromatography (silica gel 125 g, chloroform:methanol=1:0–70:1), thereby yielding 5.343 g of the aimed compound as white crystals.

$^1$H-NMR (CDCl$_3$) δ:0.88 (3H, t, J=6.8 Hz), 1.2–1.4 (22H, m), 1.61 (2H, m), 3.45 (2H, td, J=7.3, 5.9 Hz), 4.42 (1H, t, J=6.8 Hz), 4.60 (2H, d, J=6.8 Hz), 6.31 (1H, brt), 7.35 (1H, td, J=7.3, 1.5 Hz), 7.39 (1H, d, J=7.3 Hz), 7.45 (1H, td, J=7.3, 1.5 Hz), 7.51 (1H, dd, J=7.3, 1.5 Hz).

(2) [2-[[N-[3-(Dimethylamino)propyl]carbamoyloxy]methyl]phenyl]-N-tetradecyl formamide In argon gas atmosphere, pyridine (0.40 ml) and phenyl chlorocarbonate (0.46 ml) were added to a suspension of [2-(hydroxymethyl)phenyl]-N-tetradecylformamide (1.146 g) in dichloromethane (12 ml) while being cooled with ice. After being stirred for 2.5 hours at room temperature, the reaction mixture, with chloroform added thereto, was washed with 1N hydrochloric acid, saturated sodium hydrogencarbonate aqueous solution and water successively, dried over sodium sulfate anhydride, and then concentrated. In argon gas atmosphere, N,N-dimethyl-1,3-propanediamine (0.46 ml) was added to the residue. After being stirred for 2.5 hours at 70° C., the reaction mixture was purified by silica gel column chromatography (silica gel 50 g, chloroform:methanol=30:1–10:1), thereby yielding 1.382 g of the aimed compound as white crystals.

$^1$H-NMR (CDCl$_3$) δ:0.88 (3H, t, J=6.8 Hz), 1.2–1.4 (22H, m), 1.57–1.67 (4H, m), 2.21 (6H, s), 2.33 (2H, t, J=6.6 Hz), 3.24 (2H, m), 3.43 (2H, td, J=7.3, 5.9 Hz), 5.21 (2H, s), 5.88 (1H, brt), 6.89 (1H, brt), 7.34 (1H, td, J=7.3, 1.5 Hz), 7.40 (1H, td, J=7.3, 1.5 Hz), 7.44 (1H, dd, J=7.3, 1.5 Hz), 7.51 (1H, dd, J=7.3, 1.5 Hz).

Example 7

[2-[[N-[3-(Dimethylamino)propyl]carbamoyloxy]
methyl]phenyl]-N -tetradecylformamide
hydrochloride (Compound 7)

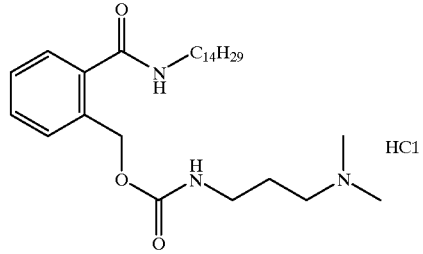

4N Hydrochloric acid—ethyl acetate solution (0.12 ml) was added to a solution of [2-[[N-[3-(dimethylamino) propyl]carbamoyloxy]methyl]phenyl]-N-tetradecylformamide (0.200 g) in ethyl acetate (2 ml) at room temperature. After being stirred for 15 minutes, the reaction mixture was concentrated. The residue was recrystallized from ethyl acetate, thereby yielding 0.197 g of the aimed compound as white crystals.

$^1$H-NMR (CDCl$_3$) δ:0.88 (3H, t, J=6.8 Hz), 1.2–1.4 (22H, m), 1.63 (2H, m), 2.03 (2H, m), 2.72 (6H, s), 3.01 (2H, t, J=7.1 Hz), 3.32 (2H, m), 3.42 (2H, m), 5.25 (2H, s), 6.12 (1H, brt), 6.79 (1H, brt), 7.33 (1H, t, J=7.3 Hz), 7.40 (1H, t, J=7.3 Hz), 7.45 (1H, d, J=7.3 Hz), 7.48 (1H, d, J=7.3 Hz), 12.02 (1H, brs).

Example 8

[2-[[N-[3-(Dimethylamino)prolpyl]carbamoyloxy]
methyl]phenyl]-N-dodecylformamide (Compound 8)

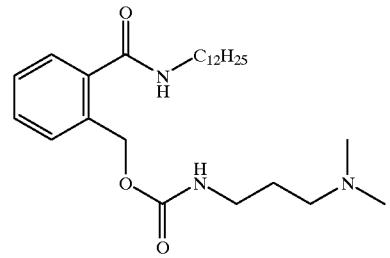

(1) N-Dodecyl-[2-(hydroxymethyl)phenyl]formamide

Dodecylamine (3.321 g) was added to phthalide (2.405 g) in argon gas atmosphere. After being stirred for 8 hours at 70° C., the reaction mixture was purified by silica gel column chromatography (silica gel 125 g, chloroform:methanol=1:0–60:1), thereby yielding 5.163 g of the aimed compound as white crystals.

$^1$H-NMR (CDCl$_3$) δ:0.88 (3H, t, J=6.8 Hz), 1.2–1.4 (18H, m), 1.61 (2H, m), 3.45 (2H, td J=7.3, 5.9 Hz), 4.42 (1H, t, J=6.8 Hz), 4.60 (2H, d, J=6.8 Hz), 6.31 (1H, brt), 7.35 (1H, td, J=7.3, 1.5 Hz), 7.39 (1H, dd, J=7.3, 1.5 Hz), 7.45 (1H, td, J=7.3, 1.5 Hz), 7.51 (1H, dd, J=7.3, 1.5 Hz).

(2) [2-[[N-[3-(Dimethylamino)propyl]carbamoyloxy] methyl]phenyl]-N-dodecyl formamide In argon gas atmosphere, pyridine (0.42 ml) and phenyl chlorocarbonate (0.48 ml) were added to a solution of N-dodecyl-[2-(hydroxymethyl)phenyl]formamide (1.102 g) in dichloromethane (12 ml) while being cooled with ice. After being stirred for 2.3 hours at room temperature, the reaction mixture, with chloroform added thereto, was washed with 1N hydrochloric acid, saturated sodium hydrogencarbonate aqueous solution and water successively, dried over sodium sulfate anhydride, and then concentrated. In argon gas atmosphere, N,N-dimethyl-1,3-propanediamine (0.48 ml) was added to the residue. After being stirred for 3 hours at 70° C., the reaction mixture was purified by silica gel column chromatography (silica gel 50 g, chloroform:methanol=30:1–10:1), thereby yielding 1.295 g of the aimed compound as white crystals.

$^1$H-NMR (CDCl$_3$) δ:0.88 (3H, t, J=6.8 Hz), 1.2–1.4 (18H, m), 1.58–1.67 (4H, m), 2.21 (6H, s), 2.33 (2H, t, J=6.6 Hz), 3.24 (2H, m), 3.43 (2H, td, J=7.3, 5.9 Hz), 5.21 (2H, s), 5.88 (1H, brt), 6.88 (1H, brt), 7.34 (1H, td, J=7.3, 1.5 Hz), 7.40 (1H, td, J=7.3, 1.5 Hz), 7.44 (1H, dd, J=7.3, 1.5 Hz), 7.52 (1H, dd, J=7.3, 1.5 Hz).

Example 9

[2-[[N-[3-(Dimethylarnino)propyl]carbamoyloxy] methyl]phenyl]-N-dodecylformamide hydrochloride (Compound 9)

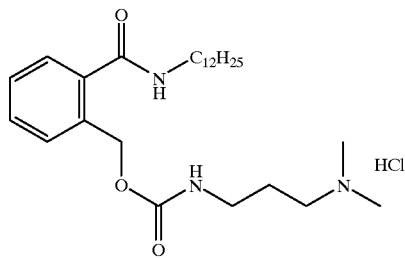

4N Hydrochloric acid—ethyl acetate solution (0.13 ml) was added to a solution of [2-[[N-[3-(dimethylamino) propyl]carbamoyloxy]methyl]phenyl]-N-dodecylformamide (0.200 g) in ethyl acetate (2 ml) at room temperature. After being stirred for 15 minutes, the reaction mixture was concentrated, thereby yielding 0.217 g of the aimed compound as white solid.

$^1$H-NMR (CDCl$_3$) δ:0.88 (3H, t, J=6.8 Hz), 1.2–1.4 (18H, m), 1.63 (2H, m), 2.04 (2H, m), 2.72 (6H, s), 2.99 (2H, t, J=7.1 Hz), 3.34 (2H, m), 3.43 (2H, m), 5.26 (2H, s), 6.03 (1H, brt), 6.76 (1H, brt), 7.34 (1H, td, J=7.3, 1.5 Hz), 7.40 (1H, td, J=7.3, 1.5 Hz), 7.45 (1H, dd J=7.3, 1.5 Hz), 7.49 (1H, dd, J=7.3, 1.5 Hz), 12.12 (1H, brs).

Example 10

N-Decyl-[2-[[N-[3-(dimethylamino)propyl] carbamoyloxy]methyl]phenyl]formamide (Compound 10)

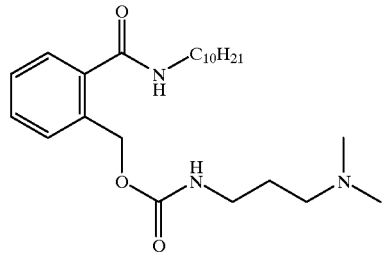

(1) N-Decyl-[2-(hydroxymethyl)phenyl]formamide

Decylamine (3.060 g) was added to phthalide (2.602 g) in argon gas atmosphere. After being stirred for 7.5 hours at 70° C., the reaction mixture was purified by silica gel column chromatography (silica gel 125 g, chloroform:methanol=1:0–50:1), thereby yielding 5.118 g of the aimed compound as white crystals.

$^1$H-NMR (CDCl$_3$) δ:0.88 (3H, t, J=6.8 Hz), 1.2–1.4 (14H, m), 1.62 (2H, m), 3.45 (2H, q, J=6.7 Hz), 4.41 (1H, brt), 4.60 (2H, d, J=6.8 Hz), 6.32 (1H, brt), 7.35 (1H, td, J=7.3, 1.5 Hz), 7.39 (1H, dd, J=7.3, 1.5 Hz), 7.44 (1H, td, J=7.3, 1.5 Hz), 7.51 (1H, dd, J=7.3, 1.5 Hz).

(2) N-Decyl-[2-[[N-[3-(dimethylamino)propyl] carbamoyloxy]methyl]phenyl]formamide In argon gas atmosphere, pyridine (0.46 ml) and phenyl chlorocarbonate (0.52 ml) were added to a solution of N-decyl-[2-(hydroxymethyl)phenyl]formamide (1.104 g) in dichloromethane (11 ml) while being cooled with ice. After being stirred for 2 hours at room temperature, the reaction mixture, with chloroform added thereto, was washed with 1N hydrochloric acid, saturated sodium hydrogencarbonate aqueous solution and water successively, dried over sodium sulfate anhydride, and then concentrated. In argon gas atmosphere, N,N-dimethyl-1,3-propanediamine (0.52 ml) was added to the residue. After being stirred for 2.5 hours at 70° C., the reaction mixture was purified by silica gel column chromatography (silica gel 50 g, chloroform:methanol=30:1–10:1), thereby yielding 1.390 g of the aimed compound as white crystals.

$^1$H-NMR (CDCl$_3$) δ:0.88 (3H, t, J=6.8 Hz), 1.2–1.4 (14H, m), 1.57–1.68 (4H, m), 2.20 (6H, s), 2.33 (2H, t, J=6.6 Hz), 3.24 (2H, m), 3.43 (2H, td, J=7.3, 5.9 Hz), 5.21 (2H, s), 5.88 (1H, brt), 6.89 (1H, brt), 7.33 (1H, td, J=7.3, 1.5 Hz), 7.40 (1H, td, J=7.3, 1.5 Hz), (1H, dd, J=7.3, 1.5 Hz), 7.51 (1H, dd, J=7.3, 1.5 Hz).

Example 11

N-Decyl-[2-[[N-[3-(dimethylamino)propyl]
carbamoyloxy]methyl]phenyl]formamide
hydrochloride (Compound 11)

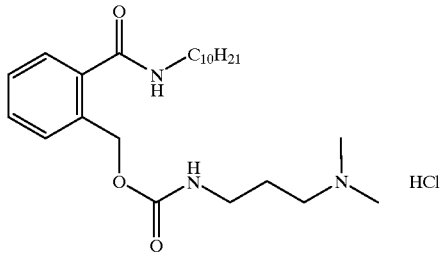

4N Hydrochloric acid—ethyl acetate solution (0.14 ml) was added to a solution of N-decyl-[2-[[N-[3-(dimethylamino)propyl]carbamoyloxy]methyl]phenyl] formamide (0.200 g) in ethyl acetate (2 ml) at room temperature. After being stirred for 10 minutes, the reaction mixture was concentrated, thereby yielding 0.209 g of the aimed compound as white syrup.

$^1$H-NMR (CDCl$_3$) δ:0.88 (3H, t, J=6.8 Hz), 1.2–1.4 (14H, m), 1.63 (2H, m), 2.04 (2H, m), 2.72 (6H, s), 3.02 (2H, m), 3.32 (2H, m), 3.42 (2H, m), 5.24 (2H, s), 6.17 (1H, brt), 6.81 (1H, brt), 7.33 (1H, t, J=7.3 Hz), 7.40 (1H, t, J=7.3 Hz), 7.45 (1H, d, J=7.3 Hz), 7.48 (1H, J=7.3 Hz).

Example 12

2-[[N-(3-Morpholinopropyl)carbamoyloxy]methyl]
phenyl]-N-octadecylformamide (Compound 12)

Pyridine (0.30 ml) and phenyl chlorocarbonate (0.34 ml) were added to a suspension of [2-(hydroxymethyl)phenyl]-N-octadecylformamide (1.00 g), which was synthesized in Example 1-1, in dichloromethane (10 ml) while being cooled with ice. After being stirred for 1 hour at room temperature, the reaction mixture, with chloroform added thereto, was washed with saturated sodium hydrogencarbonate aqueous solution and water successively, dried over sodium sulfate anhydride, and then concentrated. N-(3-Aminopropyl)morpholine (0.40 ml) was added to the residue. After being stirred for 4 hours at 70° C., the reaction mixture was purified by silica gel column chromatography (silica gel 30 g, chloroform:methanol=50:1). The resulting white solid (1.76 g) was recrystallized from n-hexane-ethyl acetate mixed solvent, thereby yielding 1.30 g of the aimed compound as white crystals.

$^1$H-NMR (CDCl$_3$) δ:0.88 (3H, t, J=6.8 Hz), 1.2–1.4 (30H, m), 1.60 (2H, m), 1.66 (2H, m), 2.40 (6H, t, J=6.6 Hz), 3.23 (2H, m), 3.40 (2H, td, J=7.3, 5.9 Hz), 3.69 (4H, m), 5.21 (2H, s), 5.93 (1H, brt), 6.94 (1H, brt), 7.31 (1H, m), 7.39 (1H, m), 7.41 (1H, m), 7.48 (1H, m).

Example 13

[2-[[N-(3-Morpholinopropyl)carbamoyloxy]methyl]
phenyl]-N-octadecylformamide hydrochloride
(Compound 13)

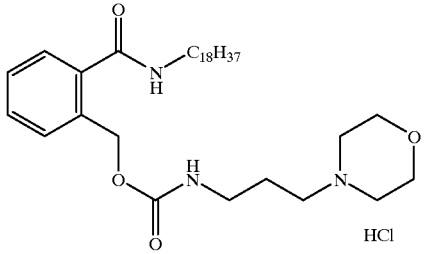

4N Hydrochloric acid—ethyl acetate solution (0.26 ml) was added to a solution of [2-[[N-(3-morpholinopropyl) carbamoyloxy]methyl]phenyl]-N-octadecylformamide (0.30 g) in ethyl acetate (4 ml) at room temperature. After being stirred for 10 minutes, the reaction mixture was concentrated. The residue was recrystallized from ethyl acetate-ethanol mixed solvent, thereby yielding 0.27 g of the aimed compound as white crystals.

$^1$H-NMR (CDCl$_3$) δ:0.88 (3H, t, J=6.8 Hz), 1.2–1.4 (30H, m), 1.63 (2H, m), 2.08 (2H, m), 2.79 (2H, m), 2.99 (2H, m), 3.32 (4H, m), 3.42 (2H, m), 3.92 (2H, m), 4.22 (2H, m), 5.25 (2H, s), 6.09 (1H, brt), 6.77 (1H, brt), 7.33 (1H, m), 7.40 (1H, m), 7.45 (1H, m), 7.48 (1H, m), 12.54 (1H, brs).

Example 14

[2-[[N-[2-(Dimethylamino)ethyl]carbamoyloxy]
methyl]phenyl]-N-octadecylformamide (Compound
14)

In argon gas atmosphere, pyridine (0.38 ml) and phenyl chlorocarbonate (0.44 ml) were added to a solution of [2-(hydroxymethyl)phenyl]-N-octadecylformamide (1.270 g), which was synthesized in Example 1-1, in chloroform (13 ml) while being cooled with ice. After being stirred for 2 hours at room temperature, the reaction mixture, with chloroform added thereto, was washed with 1N hydrochloric acid, saturated sodium hydrogencarbonate aqueous solution and water successively, dried over sodium sulfate anhydride, and then concentrated. In argon gas atmosphere, N,N-dimethylethylenediamine (0.38 ml) was added to the residue. After being stirred for 3.5 hours at 70° C, the reaction mixture was purified by silica gel column chromatography (silica gel 50 g, chloroform:methanol=30:1–20:1), thereby yielding 1.531 g of the aimed compound as white crystals.

$^1$H-NMR (CDCl$_3$) δ:0.88 (3H, t, J=6.8 Hz), 1.2–1.4 (30H, m), 1.61 (2H, m), 2.20 (6H, s), 2.38 (2H, t, J=5.9 Hz), 3.24 (2H, q, J=5.9 Hz), 3.43 (2H, td, J=7.3, 5.9 Hz), 5.23 (2H,s), 5.33 (1H, brt), 6.78 (1H, brt), 7.34 (1H, td, J=7.3, 1.5 Hz), 7.40 (1H, td, J=7.3, 1.5 Hz), 7.45 (1H, dd, J=7.3, 1.5 Hz), 7.50 (1H, dd, J=7.3, 1.5 Hz).

Example 15

[2-[[N-[2-(Dimethylamino)ethyl]carbamoyloxy]
methyl]phenyl]-N-octadecylformamide
hydrochloride (Compound 15)

4N Hydrochloric acid - ethyl acetate solution (0.12 ml) was added to a solution of [2-[[N-[2-(dimethylamino)ethyl]

carbamoyloxy]methyl]phenyl]-N-octadecylformamide (0.200 g) in ethyl acetate (2 ml) at room temperature. After being stirred for 15 minutes, the reaction mixture was concentrated. The residue was recrystallized from ethyl acetate-ethanol mixed solvent, thereby yielding 0.205 g of the aimed compound as white crystals.

¹H-NMR (CDCl₃) δ:0.88 (3H, t, J=6.8 Hz), 1.2–1.4 (30H, m), 1.63 (2H, m), 2.80 (6H, s), 3.17 (2H, t, J=5.4 Hz), 3.42 (2H, m), 3.59 (2H, m), 5.25 (2H, s), 6.79 (1H, brt), 70.1 (1H, brt), 7.33 (1H, t, J=7.3 Hz), 7.39 (1H, t, J=7.3 Hz), 7.47 (2H, d, J=7.3 Hz), 11.88 (1H, brs).

Example 16

[2-[[N-[3-(1-Imidazolyl)propyl]carbamoyloxy] methyl]phenyl]-N-octadecylformamide (Compound 16)

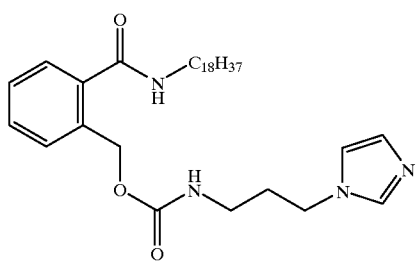

In argon gas atmosphere, pyridine (0.36 ml) and phenyl chlorocarbonate (0.42 ml) were added to a solution of [2-(hydroxymethyl)phenyl]-N-octadecylformamide (1.200 g), which was synthesized in Example 1-1, in chloroform (12 ml) while being cooled with ice. After being stirred for 2.5 hours at room temperature, the reaction mixture, with chloroform added thereto, was washed with 1N hydrochloric acid, saturated sodium hydrogencarbonate aqueous solution and water successively, dried over sodium sulfate anhydride, and then concentrated. In argon gas atmosphere, 1-(3-aminopropyl)imidazole (0.39 ml) was added to the residue. After being stirred for 2.5 hours at 100° C., the reaction mixture was purified by silica gel column chromatography (silica gel 50 g, chloroform:methanol=30:1), thereby yielding 1.073 g of the aimed compound as white crystals.

¹H-NMR (CDCl₃) δ:0.88 (3H, t, J=6.8 Hz), 1.2–1.4 (30H, m), 1.60 (2H, quintet, J=7.3 Hz), 1.97 (2H, quintet, J=6.8 Hz), 3.18 (2H, m), 3.42 (2H, m), 3.96 (2H, t, J=6.8 Hz), 4.98 (1H, brs), 5.26 (2H, s), 6.62 (1H, brs), 6.90 (1H, s), 7.03 (1H, s), 7.32–7.45 (3H, m), 7.43 (1H, s), 7.49 (1H, d, J=7.3 Hz).

Example 17

[2-[[N-[3-(1-Imidazolyl)propyl]carbamoyloxy] methyl]phenyl]-N-octadecylformamide hydrochloride (Compound 17)

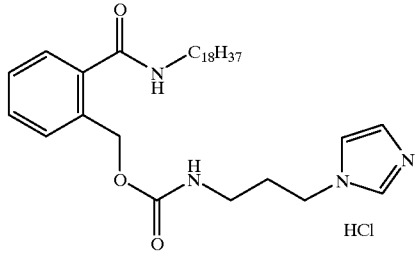

4N Hydrochloric acid—ethyl acetate solution (0.10 ml) was added to a solution of [2-[[N-[3-(1-imidazolyl)propyl] carbamoyloxy]methyl]phenyl]-N-octadecylformamide (0.200 g) in ethanol (2 ml) at room temperature. After being stirred for 20 minutes, the reaction mixture was concentrated. The residue was recrystallized from ethyl acetate-ethanol mixed solvent, thereby yielding 0.201 g of the aimed compound as white crystals.

¹H-NMR (CDCl₃) δ:0.88 (3H, t, J=6.8 Hz), 1.2–1.4 (30H, m), 1.62 (2H, m), 2.08 (2H, m), 3.17 (2H, m), 3.40 (2H, m), 4.35 (2H, t, J=6.4 Hz), 5.19 (2H, s), 6.76 (1H, brs), 6.98 (1H, brs), 7.22–7.47 (7H, m), 9.59 (1H, brs).

Example 18

[2-[[N-(Dimethylamino)carbamoyloxy]methyl] phenyl]-N-octadecylformamide (Compound 18)

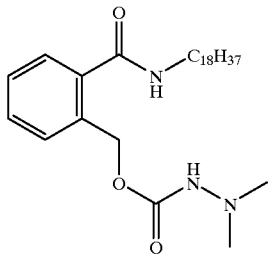

In argon gas atmosphere, pyridine (0.39 ml) and phenyl chlorocarbonate (0.46 ml) were added to a solution of [2-(hydroxymethyl)phenyl]-N-octadecylformamide (1.302 g), which was synthesized in Example 1-1, in chloroform (13 ml) while being cooled with ice. After being stirred for 2.5 hours at room temperature, the reaction mixture, with chloroform added thereto, was washed with 1N hydrochloric acid, saturated sodium hydrogencarbonate aqueous solution and water successively, dried over sodium sulfate anhydride, and then concentrated. In argon gas atmosphere, 1,1-dimethylhydrazine (1.23 ml) was added to the residue. After being stirred for 2 hours at 70° C., the reaction mixture was purified by silica gel column chromatography (silica gel 63 g, chloroform:ethyl acetate=5:1), thereby yielding 0.750 g of the aimed compound as white crystals.

¹H-NMR (CDCl₃) δ:0.88 (3H, t, J=6.8 Hz), 1.2–1.4 (30H, m), 1.61 (2H, m), 2.57 (6H, s), 3.43 (2H, td, J=7.3, 5.9 Hz), 5.27 (2H, brs), 5.66 (1H, brs), 6.70 (1H, brs), 7.30–7.51 (4H, m).

Example 19

[2-[[N-(Dimethylamino)carbamoyloxy]methyl]phenyl]-N-octadecylformamide hydrochloride (Compound 19)

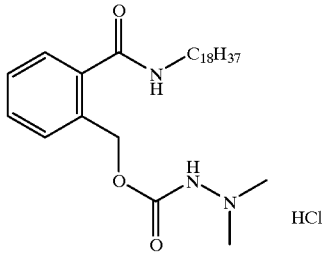

4N Hydrochloric acid—ethyl acetate solution (0.11 ml) was added to a solution of [2-[[N-(dimethylamino)carbamoyloxy]methyl]phenyl]-N-octadecylformamide (0.200 g) in ethyl acetate (6 ml) while being cooled with ice. After being stirred for 30 minutes at room temperature, the reaction mixture was concentrated. The residue was recrystallized from ethyl acetate-ethanol mixed solvent, thereby yielding 0.195 g of the aimed compound as white crystals.

$^1$H-NMR (CDCl$_3$) δ:0.88 (3H, t, J=6.8 Hz), 1.2–1.4 (30H, m), 1.60 (2H, m), 3.18 (6H, s), 3.34 (2H, m), 5.26 (2H, s), 7.06 (1H, brs), 7.23–7.42 (5H, m), 10.73 (1H, brs).

Example 20

[2-[[N-[1-(4-Methyl)piperazinyl]carbamoyloxy]methyl]phenyl]-N -octadecylformamide (Compound 20)

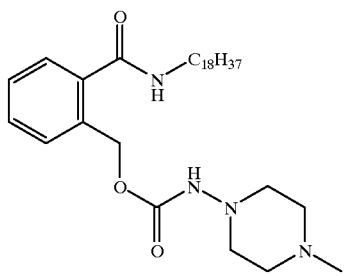

In argon gas atmosphere, pyridine (0.36 ml) and phenyl chlorocarbonate (0.42 ml) were added to a solution of [2-(hydroxymethyl)phenyl]-N-octadecylformamide (1.200 g), which was synthesized in Example 1-1, in chloroform (12 ml) while being cooled with ice. After being stirred for 2 hours at room temperature, the reaction mixture, with chloroform added thereto, was washed with 1N hydrochloric acid, saturated sodium hydrogencarbonate aqueous solution and water successively, dried over sodium sulfate anhydride, and then concentrated. In argon gas atmosphere, 1-amino-4-methylpiperazine (1.78 ml) was added to the residue. After being stirred for 4.25 hours at 70° C., the reaction mixture was purified by silica gel column chromatography (silica gel 75 g, chloroform:methanol=60:1–40:1), thereby yielding 0.671 g of the aimed compound as white crystals.

$^1$H-NMR (CDCl$_3$) δ:0.88 (3H, t, J=6.8 Hz), 1.2–1.4 (30H, m), 1.62 (2H, m), 2.29 (3H, s), 2.54 (4H, m), 2.81 (4H, m), 3.43 (2H, td, J=7.3, 5.9 Hz), 5.27 (2H, s), 5.68 (1H, brs), 6.63 (1H, brs), 7.34 (1H, td, J=7.3, 2.0 Hz), 7.40 (1H, td, J=7.3, 1.5 Hz), 7.44 (1H, d, J=7.3 Hz), 7.49 (1H, d, J=7.3 Hz).

Example 21

[2-[[N-[1-(4-Methyl)piperazinyl]carbamoyloxy]methyl]phenyl]-N-octadecylformamide monohydrochloride (Compound 21)

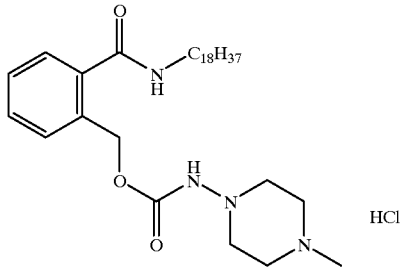

4N Hydrochloric acid—ethyl acetate solution (0.10 ml) was added to a solution of [2-[[N-[1-(4-methyl)piperazinyl]carbamoyloxy]methyl]phenyl]-N-octadecylformamide (0.200 g) in ethanol (4 ml) while being cooled with ice. After being stirred for 1 hour, the reaction mixture was concentrated. The residue was recrystallized from ethyl acetate-ethanol mixed solvent, thereby yielding 0.176 g of the aimed compound as white crystals.

$^1$H-NMR (CDCl$_3$) δ:0.88 (3H, t, J=6.8 Hz), 1.2–1.4 (30H, m), 1.61 (2H, m), 2.77 (3H, s), 3.17 (4H, m), 3.41 (6H, m), 5.29 (2H, s), 6.62 (1H, brs), 6.99 (1H, brs), 7.31–7.42 (3H, m), 7.47 (1H, d, J=7.3 Hz).

Example 22

N-[3-(Dimethylamino)propyl]-{2-[(N-octadecylcarbamoyloxy)methyl]phenyl}formamide (Compound 22)

(1) N-[3-(Dimethylamino)propyl]-[2-(hydroxymethyl)phenyl]formamide

N,N-Dimethyl-1,3-propanediamine (1.02 g) was added to phthalide (1.34 g) and then the mixture was stirred for 13 hours at 70° C. The reaction mixture (2.36 g) was used for the next reaction without purification.

$^1$H-NMR (CDCl$_3$) δ:1.76 (2H, quintet, J=6.4 Hz), 2.23 (6H, s), 2.45 (2H, t, J=6.4 Hz), 3.51 (2H, td, J=6.4, 4.9 Hz), 4.59 (2H, s), 7.30–7.55 (4H, m), 8.30 (1H, brt).

(2) N-[3-(Dimethylamino)propyl]-{2[(N-octadecylcarbamoyloxy)methyl]phenyl}formamide Triethylamine (0.65 ml) and octadecyl isocyanate (1.47 ml) were added to a solution of N-[3-(dimethylamino)propyl]-[2-(hydroxymethyl)phenyl]formamide (1.01 g) in dichloromethane (10 ml). After being stirred for 19 hours at room temperature, the reaction mixture, with chloroform added thereto, was washed with water, dried over sodium sulfate anhydride, and then concentrated. The residue was purified by silica gel column chromatography (silica gel 40 g, chloroform:methanol=50:1–10:1), thereby yielding 1.36 g of the aimed compound as white wax.

$^1$H-NMR (CDCl$_3$) δ:0.88 (3H, t, J=6.8 Hz), 1.2–1.4 (30H, m), 1.47 (2H, m), 1.78 (2H, quintet, J=6.4 Hz), 2.23 (6H, s), 2.44 (2H, t, J=6.4 Hz), 3.15 (2H, m), 3.51 (2H, m), 5.01 (1H, brt), 5.29 (2H, s), 7.33 (1H, td, J=7.3, 1.5 Hz), 7.40 (1H, td, J=7.3, 1.5 Hz), 7.45 (1H, dd, J=7.3, 1.5 Hz), 7.47 (1H, dd, J=7.3, 1.5 Hz), 7.52 (1H, brt).

Example 23

N-[3-(Dimethylamino)propyl]-{2-[(N-octadecylcarbamoyloxy)methyl]phenyl}formamide hydrochloride (Compound 23)

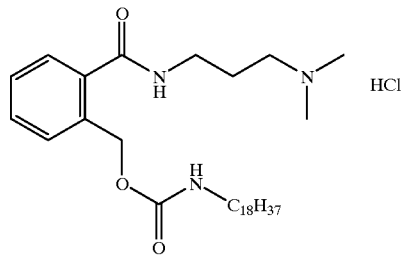

4N Hydrochloric acid—ethyl acetate solution (0.35 ml) was added to a solution of N-[3-(dimethylamino)propyl]-{2-[(N-octadecylcarbamoyloxy)methyl]phenyl}formamide (0.49 g) in ethyl acetate (10 ml) at room temperature. After being stirred for 5 minutes, the reaction mixture was concentrated. The residue was recrystallized from ethyl acetate, thereby yielding 0.41 g of the aimed compound as white crystals.

$^1$H-NMR (CDCl$_3$) δ:0.88 (3H, t, J=6.8 Hz), 1.2–1.4 (30H, m), 1.49 (2H, m), 2.21 (2H, m), 2.80 (3H, s), 2.81 (3H, s), 3.12 (2H, t, J=7.3 Hz), 3.18 (2H, m), 3.66 (2H, m), 5.24 (2H, s), 7.36 (1H, td, J=7.3, 1.5 Hz), 7.41 (1H, td, J=7.3, 1.5 Hz), 7.50 (1H, dd, J=7.3, 1.5 Hz), 7.55 (1H, dd, J=7.3, 1.5 Hz), 7.57 (1H, brt), 12.05 (1H, brs).

Example 24

[2-[[N-(2-Aminoethyl)carbamoyloxy]methyl]phenyl]-N-octadecylformamide (Compound 24)

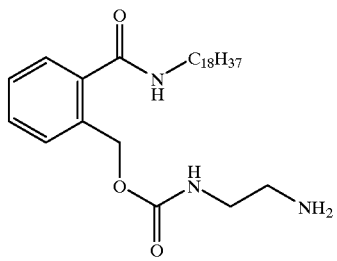

Pyridine (0.46 ml) and phenyl chlorocarbonate (0.52 ml) were added to a suspension of [2-hydroxymethyl)phenyl]-N-octadecylformamide (1.53 g) in dichloromethane (16 ml) while being cooled with ice. After being stirred for 1 hours at room temperature, the reaction mixture, with chloroform added thereto, was washed with saturated sodium hydrogencarbonate aqueous solution and water successively, dried over sodium sulfate anhydride, and then concentrated. Ethylenediamine (0.38 ml) was added to the residue. After being stirred for 5 hours at 70° C., the reaction mixture was purified by silica gel column chromatography (silica gel 40 g, chloroform:methanol=20:1–10:1), thereby yielding 1.04 g of the aimed compound as white solid.

$^1$H-NMR (CDCl$_3$) δ:0.88 (3H, t, J=6.8 Hz), 1.2–1.4 (30H, m), 1.59 (4H, m), 2.79 (2H, t, J=5.9 Hz), 3.20 (2H, q, J=5.9 Hz), 3.42 (2H, td, J=7.8, 5.9 Hz), 5.23 (2H, s), 5.34 (1H, brs), 6.72 (1H, brs), 7.32 (1H, td, J=7.3, 1.5 Hz), 7.39 (1H, td, J=7.3, 1.5 Hz), 7.43 (1H, dd, J=7.3 1.5 Hz), 7.48 (1H, dd, J=7.3, 1.5 Hz).

Example 25

[2-[[N-(2-Aminoethyl)carbamoyloxy]methyl]phenyl]-N-octadecylformamide hydrochloride (Compound 25)

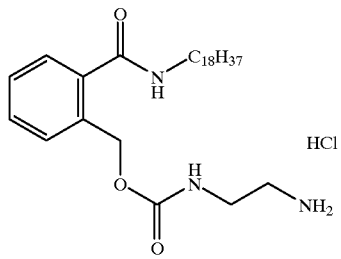

4N Hydrochloric acid—ethyl acetate solution (0.30 ml) was added to a solution of [2-[[N-(2-Aminoethyl)carbamoyloxy]methyl]phenyl]-N-octadecylformamide (0.33 g) in a mixture of ethyl acetate (10 ml) and ethanol (2 ml) at room temperature. After being stirred for 10 minutes, the reaction mixture was concentrated. The residue was recrystallized from ethyl acetate-ethanol mixed solvent, thereby yielding 0.30 g of the aimed compound as white crystals.

$^1$H-NMR (DMSO-d$_6$) δ:0.85 (3H, t, J=6.8 Hz), 1.1–1.4 (30H, m), 1.50 (2H, m), 2.86 (2H, t, J=6.8 Hz), 3.21 (2H, q, J=6.8 Hz), 3.27 (2H, dt, J=6.8, 5.9 Hz), 5.20 (2H, s), 7.3–7.5 (5H, m), 8.00 (3H, brs), 8.28 (1H, brt).

Example 26

[2-[[N-[2-(Dibutylamino)ethyl]carbamoyloxy]methyl]phenyl]-N-octadecylformamide (Compound 26)

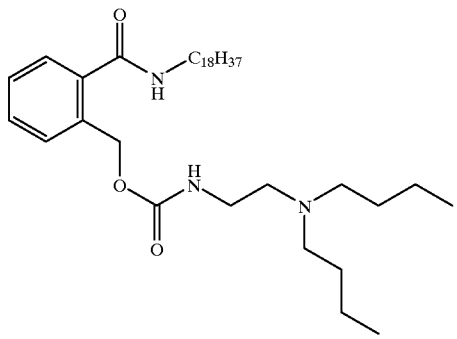

Pyridine (0.30 ml) and phenyl chlorocarbonate (0.35 ml) were added to a suspension of [2-(hydroxymethyl)phenyl]-N-octadecylformamide (1.38 g) in dichloromethane (10 ml) while being cooled with ice. After being stirred for 1 hours at room temperature, the reaction mixture, with chloroform added thereto, was washed with saturated sodium hydrogencarbonate aqueous solution and water successively, dried over sodium sulfate anhydride, and then concentrated. N,N-Di-n-butylethylenediamine (0.57 ml) was added to the residue. After being stirred for 3 hours at 70° C., the reaction mixture was purified by silica gel column chromatography (silica gel 40 g, chloroform:methanol=50:1), thereby yielding 1.31 g of the aimed compound as white solid.

¹H-NMR (CDCl₃) δ:0.88 (3H, t, J=7.3 Hz), 0.90 (6H, t, J=7.3 Hz), 1.1–1.5 (38H, m), 1.62 (2H, m), 2.38 (4H, t, J=7.3 Hz), 2.49 (2H, t, J=5.9 Hz), 3.19 (2H, q, J=5.9 Hz), 3.43 (2H, q, J=6.8 Hz), 5.23 (2H, s), 5.34 (1H, brs), 6.87 (1H, brs), 7.34 (1H, td, J=7.3, 1.5 Hz), 7.40 (1H, td, J=7.3, 1.5 Hz), 7.45 (1H, dd, J=7.3, 1.5 Hz), 7.52 (1H, dd, J=7.3, 1.5 Hz).

Example 27

[2-[[N-[2-(Dibutylamino)ethyl]carbamoyloxy]methyl]phenyl]-N-octadecylformamide hydrochloride (Compound 27)

4N Hydrochloric acid—ethyl acetate solution (0.90 ml) was added to a solution of [2-[[N-[2-(dibutylamino)ethyl]carbamoyloxy]methylphenyl]-N-octadecylformamide (1.09 g) in ethyl acetate (10 ml) at room temperature. After being stirred for 10 minutes, the reaction mixture was concentrated. The residue was recrystallized from ethyl acetate, thereby yielding 0.91 g of the aimed compound as white crystals.

¹H-NMR (CDCl₃) δ:0.88 (3H, t, J=7.3 Hz), 0.96 (6H, t, J=7.3 Hz), 1.2–1.5 (34H, m), 1.65 (2H, m), 1.74 (4H, m), 2.98(4H, m), 3.11 (2H, m), 3.44 (2H, q, J=6.8 Hz), 3.60 (2H, m), 5.26 (2H, s), 6.79 (1H, brt), 7.14 (1H, brt), 7.33 (1H, td, J=7.3, 1.5 Hz), 7.38 (1H, td, J=7.3, 1.5 Hz), 7.47 (1H, dd, J=7.3, 1.5 Hz), 7.48 (1H, dd, J=7.3, 1.5 Hz), 11.69 (1H, brs).

Example 28

[2-[[N-[2-(Diethylamino)ethyl]carbamoyloxy]methyl]phenyl]-N-octadecylformamide (Compound 28)

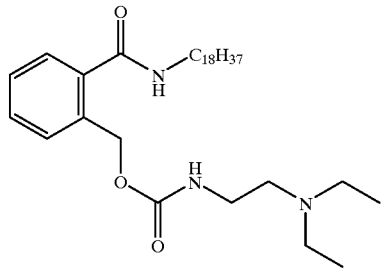

Pyridine (2.43 ml) and phenyl chlorocarbonate (2.76 ml) were added to a solution of [2-(hydroxymethyl)phenyl]-N-octadecylformamide (8.07 g) in chloroform (80 ml) while being cooled with ice. After being stirred for 4 hours at room temperature, the reaction mixture, with chloroform added thereto, was washed with saturated sodium hydrogencarbonate aqueous solution, 1N hydrochloric acid and saturated brine successively, dried over sodium sulfate anhydride, and then filtrated. The solvent was evaporated out from the filtrate to obtain white solid (9.46 g) as intermediate (a). N,N-Diethylethylenediamine (0.64 g) was added to this intermediate (a) (2.62 g). After being stirred for 2 hours at 70° C., the reaction mixture, with chloroform added thereto, was washed with 1N sodium hydroxide aqueous solution and saturated brine successively, and then dried over sodium sulfate anhydride. The solvent was evaporated out and the residue was purified by silica gel column chromatography (silica gel 80 g, chloroform:methanol=50:1), thereby yielding 1.46 g of the aimed compound as white solid.

¹H-NMR (CDCl₃) δ:0.88 (3H, t, J=6.6 Hz), 0.99 (6H, t, J=7.1 Hz), 1.1–1.5 (30H, m), 1.61 (2H, m), 2.50 (2H, t, J=7.3 Hz), 2.51 (4H, q, J=6.8 Hz), 3.20 (2H, q, J=5.4 Hz), 3.43 (2H, td, J=6.8, 6.4 Hz), 5.22 (2H, s), 5.39 (1H, brs), 6.86 (1H, brs), 7.33 (1H, t, J=6.8 Hz), 7.40 (1H, t, J=7.1 Hz), 7.44 (1H, d, J=7.3 Hz), 7.50 (1H, d, J=7.8 Hz).

Example 29

[2-[[N-[2-(Diethylamino)ethyl]carbamoyloxy]methyl]phenyl]-N-octadecylformamide hydrochloride (Compound 29)

4N Hydrochloric acid—ethyl acetate solution (0.20 ml) was added to a solution of [2-[[N-[2-(diethylamino)ethyl]carbamoyloxy]methyl]phenyl]-N-octadecylformamide (0.42 g) in ethyl acetate (5 ml) at room temperature. After being stirred for 15 minutes, the reaction mixture was concentrated. The residue was recrystallized from ethyl acetate-ethanol mixed solvent, thereby yielding 0.35 g of the aimed compound as white crystals.

¹H-NMR (CDCl₃) δ:0.88 (3H, t, J=6.8 Hz), 1.1–1.5 (30H, m), 1.32 (6H, t, J=7.1 Hz), 1.64 (2H, m), 3.0–3.2 (6H, m), 3.43 (2H, brs), 3.57 (2H, brs), 5.24 (2H, s), 7.10 (1H, brs), 7.16 (1H, brs), 7.32 (1H, brt, J=6.8 Hz), 7.38 (1H, brt, J=6.8 Hz), 7.46 (2H, m), 11.35 (1H, brs).

Example 30

[2-[[N-[2-(Diisopropylamino)ethyl]carbamoyloxy]methyl]phenyl]-N-octadecylformamide (Compound 30)

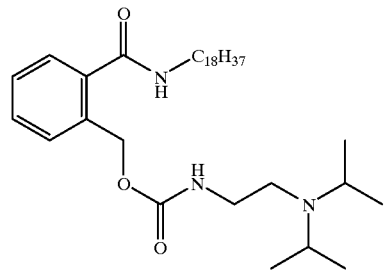

N,N-Diisopropylethylenediamine (0.79 g) was added to the intermediate (a) (2.62g) obtained in Example 28. After being stirred for 2 hours at 70° C., the reaction mixture, with chloroform added thereto, was washed with 1N sodium hydroxide aqueous solution and saturated brine successively, dried over sodium sulfate anhydride, and then filtrated. The solvent was evaporated out and the residue was purified by silica gel column chromatography (silica gel 85 g, chloroform:methanol=100:1), thereby yielding 1.45 g of the aimed compound as white solid.

¹H-NMR (CDCl₃) δ:0.88 (3H, t, J=6.8 Hz), 0.98 (12H, d, J=6.3 Hz), 1.2–1.5 (30H, m), 1.61 (2H, m), 2.54 (2H, t, J=6.1 Hz), 2.98 (2H, m), 3.12 (2H, q, J=5.4 Hz), 3.43 (2H, td, J=7.3, 5.9 Hz), 5.21 (2H, s), 5.33 (1H, brs), 6.94 (1H, brs), 7.33 (1H, t, J=7.3 Hz), 7.40 (1H, t, J=6.8 Hz), 7.43 (1H, d, J=7.3 Hz), 7.51 (1H, d, J=7.8 Hz).

Example 31

[2-[[N-[2-(Diisopropylamino)ethyl]carbamoyloxy]methyl]phenyl]-N-octadecylformamide hydrochloride (Compound 31)

4N Hydrochloric acid—ethyl acetate solution (0.20 ml) was added to a solution of [2-[[N-[2-(diisopropylamino)

ethyl]carbamoyloxy]methyl]phenyl]-N-octadecylformamide (0.44 g) in ethyl acetate (5 ml) at room temperature. After being stirred for 15 minutes, the reaction mixture was concentrated. The residue was recrystallized from ethyl acetate-ethanol mixed solvent, thereby yielding 0.37 g of the aimed compound as white crystals.

$^1$H-NMR (CDCl$_3$) δ:0.88 (3H, t, J=6.8 Hz), 1.2–1.5 (30H, m), 1.34 (6H, d, J=6.4 Hz), 1.40 (6H, d, J=6.3 Hz), 1.65 (2H, m), 3.05 (2H, brs), 3.45 (2H, q, J=6.3 Hz), 3.54 (2H, m), 3.58 (2H, brs), 5.24 (2H, s), 7.12 (1H, brs), 7.32 (1H, brt, J=7.3 Hz), 7.33 (1H, brs), 7.37 (1H, brt, J=7.3 Hz), 7.43 (1H, d, J=7.3 Hz), 7.48 (1H, d, J=7.8 Hz), 10.81 (1H, brs).

Example 32

[2-[[N-[3-[Bis(2-hydroxyethyl)amino]propyl]carbamoyloxy]methyl]phenyl]-N-octadecylformamide (Compound 32)

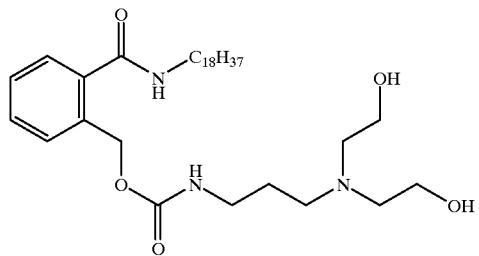

N-(3-Aminopropyl)diethanolamine (0.89 g) was added to the intermediate (a) (2.62g) obtained in Example 28. After being stirred for 2.5 hours at 70° C., the reaction mixture, with chloroform added thereto, was washed with 1N sodium hydroxide aqueous solution and saturated brine successively, dried over sodium sulfate anhydride, and then filtrated. The solvent was evaporated out and the residue was purified by silica gel column chromatography (silica gel 70 g, chloroform:methanol=50:1–30:1), thereby yielding 1.17 g of the aimed compound as white solid.

$^1$H-NMR (CDCl$_3$) δ:0.88 (3H, t, J=6.8 Hz), 1.2–1.4 (30H, m), 1.60 (2H, m), 1.67 (2H, m), 2.3–2.9 (8H, m), 3.28 (2H, q, J=6.0 Hz), 3.40 (2H, td, J=6.8, 6.4 Hz), 3.58 (4H, m), 5.18 (2H, s), 6.06 (1H, brs), 6.65 (1H, brs), 7.33 (1H, brt, J=7.3 Hz), 7.39 (1H, brt, J=7.3 Hz), 7.4–7.5 (2H, m).

Example 33

[2-[[N-[3-[Bis(2-hydroxyethyl)amino]propyl]carbamoyloxy]methyl]phenyl]-N-octadecylformamide hydrochloride (Compound 33)

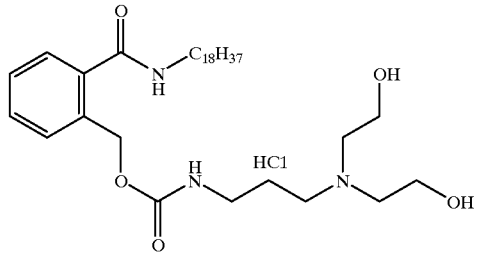

4N Hydrochloric acid—ethyl acetate solution (0.20 ml) was added to a solution of [2-[[N-[3-[bis(2-hydroxyethyl)amino]propyl]carbamoyloxy]methyl]phenyl]-N-octadecylformamide (0.47 g) in a mixture of ethyl acetate (5 ml) and chloroform (2 ml) at room temperature. After being stirred for 10 minutes, the reaction mixture was concentrated. The residue was recrystallized from ethyl acetate-ethanol-chloroform mixed solvent, thereby yielding 0.44 g of the aimed compound as white crystals.

$^1$H-NMR (CDCl$_3$) δ:0.88 (3H, t, J=6.8 Hz), 1.1–1.4 (30H, m), 1.57 (2H, m), 1.94 (2H, m), 3.1–3.4 (8H, m), 3.86 (4H, brs), 4.59 (4H, brs), 5.11 (2H, s), 6.73 (1H, brs), 7.2–7.5 (5H, m), 9.15 (1H, brs).

Example 34

[2-(N-Octadecylcarbamoyl)phenyl]methyl-4-methylpiperazinecarboxylate (Compound 34)

Pyridine (0.46 ml) and phenyl chlorocarbonate (0.52 ml) were added to a suspension of [12-(hydroxymethyl)phenyl]-N-octadecylformamide (1.52 g), which was synthesized in Example 1-1, in dichloromethane (15 ml) while being cooled with ice. After being stirred for 2 hour at room temperature, the reaction mixture, with chloroform added thereto, was washed with saturated sodium hydrogencarbonate aqueous solution and saturated brine successively, dried over sodium sulfate anhydride, and then concentrated. N-Methylpiperazine (0.47 ml) was added to the residue. After being stirred for 5 hours at 70° C., the reaction mixture was purified by silica gel column chromatography (silica gel 40 g, chloroform:methanol=50:1) and then recrystallized from n-hexane-ethyl acetate mixed solvent, thereby yielding 1.72 g of the aimed compound as white solid.

$^1$H-NMR (CDCl$_3$) δ:0.88 (3H, t, J=6.8 Hz), 1.2–1.4 (30H, m), 1.60 (2H, m), 2.29 (3H, s), 2.36 (4H, m), 3.43 (2H, m), 3.51(4H, m), 5.28 (2H, s), 6.80 (1H, brs), 7.34 (1H, m) 7.39–7.43 (2H, m), 7.50 (1H, d, J=7.3 Hz).

Example 35

[2-(N-Octadecylcarbamoyl)phenyl]methyl-4-methylpiperazinecarboxylate hydrochloride (Compound 35)

4N Hydrochloric acid—ethyl acetate solution (0.28 ml) was added to a solution of [2-(N-octadecylcarbamoyl)phenyl]methyl-4-methylpiperazinecarboxylate (0.30 g) in ethyl acetate (4 ml) at room temperature. After being stirred for 10 minutes, the reaction mixture was concentrated. The residue was recrystallized from ethyl acetate-ethanol mixed solvent, thereby yielding 0.32 g of the aimed compound as white solid.

$^1$H-NMR (CDCl$_3$) δ:0.88 (3H, t, J=6.8 Hz), 1.2–1.4 (30H, m), 1.60 (2H, m), 2.80 (3H, d, J=4.4 Hz), 2.85 (2H, m), 3.37–3.42 (4H, m), 3.71 (2H, m), 4.22 (2H, m), 5.3 (2H, brs), 6.31 (1H, brt), 7.35–7.46 (4H, m), 13.21 (1H, brs).

Example 36

[2-(N-Octadecylcarbamoyl)phenyl]methyl-4-(2-hydroxyethyl)piperazinecarboxylate (Compound 36)

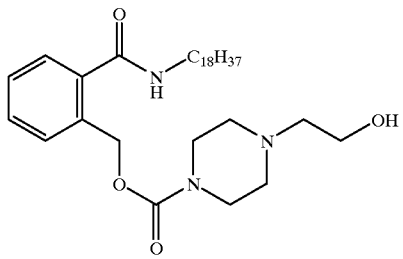

Pyridine (1.15 ml) and phenyl chlorocarbonate (1.31 ml) were added to a suspension of [2-(hydroxymethyl)phenyl]-N-octadecylformamide (3.83 g), which was synthesized in Example 1-1, in dichloromethane (40 ml) while being cooled with ice. After being stirred for 1 hour at room temperature, the reaction mixture, with chloroform added thereto, was washed with 1N hydrochloric acid, saturated sodium hydrogencarbonate aqueous solution and saturated brine successively, dried over sodium sulfate anhydride, and then concentrated. N-(Hydroxyethyl)piperazine (0.40 g) was added to the residue (1.55 g). After being stirred for 2 hours at 70° C., the reaction mixture was dissolved in toluene and the solution was washed with 1N sodium hydroxide aqueous solution, dried over sodium sulfate anhydride, and then concentrated. The residue was purified by silica gel column chromatography (silica gel 40 g, chloroform:methanol=20:1), thereby yielding 1.31 g of the aimed compound as white solid.

$^1$H-NMR (CDCl$_3$) δ:0.88 (3H, t, J=6.8 Hz), 1.2–1.4 (30H, m), 1.60 (2H, m), 2.47 (4H, m), 2.55 (2H, t, J=5.4 Hz), 3.41 (2H, td, J=7.3, 5.9 Hz), 3.51(4H, m), 3.63 (2H, t, J=5.4 Hz), 5.28 (2H, s), 6.81 (1H, t, J=5.9 Hz), 7.32–7.36 (1H, m), 7.40–7.42 (2H, m), 7.49 (1H, d, J=7.8 Hz).

Example 37

[2-(N-Octadecylcarbamoyl)phenyl]methyl-4-(2-hydroxyethyl)piperazinecarboxylate hydrochloride (Compound 37)

4N Hydrochloric acid—ethyl acetate solution (0.40 ml) was added to a solution of [2-(N-octadecylcarbamoyl)phenyl]methyl 4-(2-hydroxyethyl)piperazinecarboxylate (0.45 g) in ethyl acetate (10 ml) at room temperature. After being stirred for 10 minutes, the reaction mixture was concentrated. The residue was recrystallized from ethyl acetate-ethanol mixed solvent, thereby yielding 0.39 g of the aimed compound as white solid.

$^1$H-NMR (CDCl$_3$) δ:0.88 (3H, t, J=7.1 Hz), 1.2–1.4 (30H, m), 1.60 (2H, m), 2.8–4.4 (8H, m), 3.20 (2H, m), 3.38 (2H, m), 4.01 (2H, m), 4.76 (1H, brs), 5.32 (2H, s), 6.48 (1H, t J=5.9 Hz), 7.32–7.44 (4H, m).

Example 38

[[2-[(4-Methylpiperazinyl)carbonyl]phenyl]methoxyl]-N-octadecylformamide (Compound 38)

(1) 2-(Hydroxymethyl)phenyl-4-methylpiperazinyl ketone

N-Methylpiperazine (5.27 g) was added to phthalide (7.05 g) and then the mixture was stirred for 38.5 hours at 70° C. The reaction mixture was suspended in saturated brine and extracted with ethyl acetate. The organic layer was dried over sodium sulfate anhydride and concentrated, thereby yielding 9.83 of product containing the aimed compound as light brown syrup.

(2) [[2-[(4-Methylpiperazinyl)carbonyl]phenyl]methoxy]-N-octadecylformamide

Triethylamine (6.50 ml) and octadecyl isocyanate (14.40 ml) were added to a solution of the syrup containing 2-(hydroxymethyl)phenyl 4-methylpiperazinyl ketone (9.83 g) in dichloromethane (100 ml). After being stirred for 14.5 hours at room temperature, the insoluble material was filtrated out under a vacuum. The filtrate was concentrated. The residue was purified by silica gel column chromatography (silica gel 225 g, chloroform:methanol=80:1), thereby yielding 12.00 g of the aimed compound as white solid.

$^1$H-NMR (CDCl$_3$) δ:0.88 (3H, t, J=6.8 Hz), 1.2–1.35 (30H, m), 1.48 (2H, m), 2.31 (3H, s & 2H, m), 2.48 (2H, m), 3.16 (2H, td, J=7.3, 5.9 Hz), 3.27(2H, m), 3.82 (2H, m), 4.72 (1H, brt), 5.10 (1H, brs), 5.16 (1H, brs), 7.22 (1H, dd, J=7.3, 1.5 Hz), 7.33 (1H, td, J=7.3, 1.5 Hz), 7.38 (1H, td, J=7.3, 1.5 Hz), 7.44 (1H, d, J=7.3 Hz).

Example 39

[[2-[(4-Methylpiperazinyl)carbonyl]phenyl]methoxy]-N-octadecylformamide hydrochloride (Compound 39)

4N Hydrochloric acid—ethyl acetate solution (8.50 ml) was added to a solution of [[2-[(4-methylpiperazinyl)carbonyl]phenyl]methoxy]-N-octadecylformamide (11.98 g) in ethyl acetate (120 ml) while being cooled with ice. After being stirred for 30 minutes at room temperature, the reaction mixture was concentrated. The residue was recrystallized from ethyl acetate-ethanol mixed solvent, thereby yielding 12.12 g of the aimed compound as white solid.

$^1$H-NMR (CDCl$_3$) δ:0.88 (3H, t, J=6.8 Hz), 1.2–1.35 (30H, m), 1.48 (2H, m), 2.82 (3H, brs), 2.9–4.1 (10H, m), 4.88 (2H, m), 5.37 (1H, m), 7.20 (1H, d, J=7.3 Hz), 7.36 (1H, t, J=7.3 Hz), 7.43 (1H, t, J=7.3 Hz), 7.49 (1H, d, J=7.3 Hz), 13.18 (1H, brs).

Example 40

[2-[[N-[3-(Dibutylamino)propyl]carbamoyloxy]methyl]phenyl]-N-octadecylformamide (Compound 40)

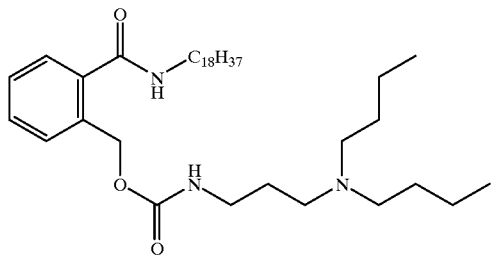

Pyridine (0.67 ml) and phenyl chlorocarbonate (0.76 ml) were added to a suspension of [2-(hydroxymethyl)phenyl]-N-octadecylformamide (2.20 g), which was synthesized in Example 1-1, in chloroform (22 ml) while being cooled with ice. After being stirred for 2 hours at room temperature, the reaction mixture, with chloroform added thereto, was washed with 1N hydrochloric acid, saturated sodium hydrogencarbonate aqueous solution and saturated brine successively, dried over sodium sulfate anhydride, and then concentrated. 3-(Dibutylamino)propylamine (1.36 ml) was added to the residue. After being stirred for 3 hours at 70° C., the reaction mixture was purified by silica gel column chromatography (silica gel 100 g, chloroform:methanol= 60:1–30:1), thereby yielding 3.11 g of the aimed compound as white solid.

$^1$H-NMR (CDCl$_3$) δ:0.88 (3H, t, J=6.8 Hz), 0.91 (6H, t, J=7.1 Hz), 1.2–1.5 (36H, m), 1.61 (6H, m), 2.39 (4H, m), 2.49 (2H, m), 3.25 (2H, q, J=5.7 Hz), 3.43 (2H, q, J=6.7 Hz), 5.21 (2H, s), 6.49 (1H, brt), 7.03 (1H, brt), 7.33 (1H, td, J=7.3, 1.5 Hz), 7.38 (1H, dd, J=7.3, 1.5 Hz), 7.42 (1H, td, J=7.3, 1.5 Hz), 7.52 (1H, dd, J=7.3, 1.5 Hz).

Example 41

[2-[[N-[3-(Dibutylamino)propyl]carbamoyloxy] methyl]phenyl]-N-octadecylformamide hydrochloride (Compound 41)

4N Hydrochloric acid—ethyl acetate solution (1.36 ml) was added to a solution of [2-[[N-[3-(dibutylamino)propyl]carbamoyloxy]methyl]phenyl]-N-octadecylformamide (2.60 g) in ethyl acetate (26 ml) while being cooled with ice. After being stirred for 30 minutes, the reaction mixture was concentrated, thereby yielding 2.75 g of the aimed compound as white solid.

$^1$H-NMR (CDCl$_3$) δ:0.88 (3H, t, J=6.8 Hz), 0.97 (6H, t, J=7.3 Hz), 1.2–1.4 (36H, m), 1.6–1.8 (4H, m), 2.04 (2H, m), 2.85–3.0 (6H, m), 3.31 (2H, q, J=6.0 Hz), 3.43 (2H, q, J=6.8 Hz), 5.25 (2H, s), 6.02 (1H, brt), 6.84 (1H, brt), 7.33 (1H, td, J=7.3, 1.5 Hz), 7.39 (1H, td, J=7.3, 1.5 Hz), 7.45 (1H, dd, J=7.3, 1.5 Hz), 7.49 (1H, dd, J=7.3, 1.5 Hz), 11.68 (1H, brs).

Example 42

2-[2-(Octadecylamino)-2-oxoethyl]benzyl-4-methyl-1-piperazinecarboxylate (Compound 42)

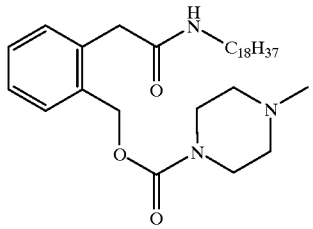

(1) 2-[2-(Hydroxymethyl)phenyl]-N-octadecylacetamide

Octadecylamine (3.71 g) was added to 3-isochromanone (2.04 g) and then the mixture was stirred for 4.5 hours at 110° C., thereby yielding 5.75 g of the aimed compound as light brown solid.

$^1$H-NMR (CDCl$_3$) δ:0.88 (3H, t, J=6.8 Hz), 1.2–1.35 (30H, m), 1.44 (2H, m), 3.19 (2H, q, J=6.7 Hz), 3.62 (2H, s), 3.83 (1H, brs), 4.67 (2H, s), 5.90 (1H, brt), 7.22–7.31 (3H, m), 7.40 (1H, m).

(2) 2-[2-(Octadecylamino)-2-oxoethyl]benzyl-4-methyl-1-piperazinecarboxylate

Pyridine (0.80 ml) and phenyl chlorocarbonate (0.92 ml) were added to a suspension of 2-[2-(hydroxymethyl)phenyl]-N-octadecylacetamide (2.73 g) in chloroform (42 ml) while being cooled with ice. After being stirred for 2.5 hours at room temperature, the reaction mixture, with chloroform added thereto, was washed with 1N hydrochloric acid, saturated sodium hydrogencarbonate aqueous solution and saturated brine successively, dried over sodium sulfate anhydride, and then concentrated. N-Methylpiperazine (0.80 ml) was added to the residue. After being stirred for 2 hours at 80° C., the reaction mixture was purified by silica gel column chromatography (silica gel 100 g, ethyl acetate (380 ml) and then chloroform:methanol=40:1–30:1), thereby yielding 3.21 g of the aimed compound as light yellow solid.

$^1$H-NMR (CDCl$_3$) δ:0.88 (3H, t, J=6.8 Hz), 1.15–1.35 (30H, m), 1.39 (2H, m), 2.29 (3H, s), 2.34 (4H, m), 3.16 (2H, q, J=6.7 Hz), 3.48 (4H, J=4.9 Hz), 3.65 (2H, s), 5.16 (2H, s), 5.62 (1H, brt), 7.27–7.35 (3H, m), 7.40 (1H, m).

Example 43

2-[2-(Octadecylamino)-2-oxoethyl]benzyl-4-methyl-1-piperazinecarboxylate hydrochloride (Compound 43)

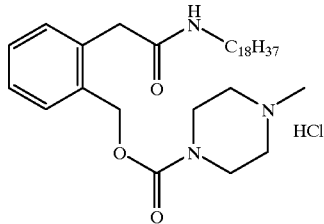

4N Hydrochloric acid—ethyl acetate solution (1.44 ml) was added to a solution of 2-[2-(octadecylamino)-2-oxoethyl]benzyl-4methyl-1-piperazinecarboxylate (2.60 g) in ethyl acetate (39 ml) at room temperature. After being stirred for 30 minutes, the reaction mixture was concentrated. The residue was recrystallized from ethyl acetate-ethanol mixed solvent, thereby yielding 2.42 g of the aimed compound as white solid.

$^1$H-NMR (CDCl$_3$) δ:0.88 (3H, t, J=6.8 Hz), 1.15–1.35 (30H, m), 1.41 (2H, m), 2.79 (3H, s), 2.84 (2H, m), 3.12 (2H, m), 3.38 (2H, m), 3.63 (2H, s), 3.70 (2H, m), 4.05–4.35 (2H, m), 5.17 (2H, brs), 5.51 (1H, brt), 7.27 (1H, d, J=8.8 Hz), 7.31–7.39 (3H, m), 13.23 (1H, brs).

Example 44

4,5-Dimethoxy-2-[2-(4-methylpiperazinyl)-2-oxoethyl]benzyl N-octadecylcarbamate (Compound 44)

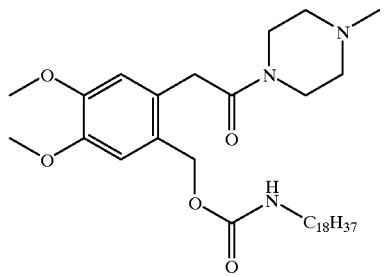

(1) 2-[2-(Hydroxymethyl)-4,5-dimethoxyphenyl]-1-(4-methylpiperazinyl)-1-ethanone N-Methylpiperazine (0.51 ml) was added to 6,7-dimethoxy-3-isochromanone (0.94 g) and then the mixture was stirred for 7.75 hours at 120° C. The reaction mixture was purified by silica gel column chromatography (silica gel 50 g, chloroform:methanol=100:1–10:1), thereby yielding 0.83 g of the aimed compound as light brown solid.

$^1$H-NMR (CDCl$_3$) δ:2.32 (3H, s), 2.39 (2H, brt), 2.44 (2H, brt), 3.68 (4H, t, J=4.6 Hz), 3.75 (2H, s), 3.86 (3H, s), 3.89 (3H, s), 3.8–3.95 (1H, brs), 4.53 (2H, s), 6.63 (1H, s), 6.94 (1H, s).

(2) 4,5-Dimethoxy-2-[2-(4-methylpiperazinyl)-2-oxoethyl] benzyl N-octadecylcarbamate Triethylamine (0.41 ml) and octadecyl isocyanate (0.91 ml) were added to a solution of 2-[2-(hydroxymethyl)-4,5-dimethoxyphenyl]-1-(4-methylpiperazinyl)-1-ethanone (0.82 g) in dichloromethane (8.5 ml) at room temperature. After being stirred for 15 hours, resulting insoluble materials were filtrated out under a vacuum and washed with chloroform. A mixture of the filtrate and chloroform used for washing was washed with saturated sodium hydrogencarbonate aqueous solution and saturated brine successively, dried over sodium sulfate anhydride, and then concentrated. The residue was purified by silica gel column chromatography (silica gel 50 g, chloroform:methanol=50:1–30:1), thereby yielding 0.83 g of the aimed compound as light brown solid.

$^1$H-NMR (CDCl$_3$) δ:0.88 (3H, t, J=6.8 Hz), 1.15–1.35 (30H, m), 1.47 (2H, m), 2.28 (3H, s), 2.30 (2H, t, J=4.9 Hz), 2.38 (2H, t, J=4.9 Hz), 3.15 (2H, q, J=6.3 Hz), 3.47 (2H, t, J=4.9 Hz), 3.67 (2H, t, J=4.9 Hz), 3.75 (2H, s), 3.86 (3H, s) 3.88 (3H, s), 4.66 (1H,brt), 5.02 (2H, s), 6.71 (1H, s), 6.89 (1H, s).

Example 45

4,5-Dimethoxy-2-[2-(4-methylpiperazinyl)-2-oxoethyl]benzyl N-octadecylcarbamate hydrochloride (Compound 45)

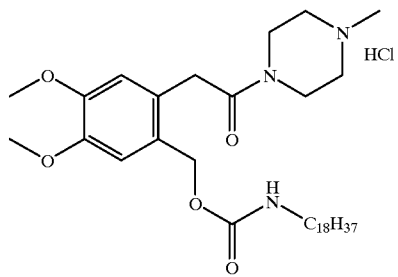

4N Hydrochloric acid—ethyl acetate solution (0.41 ml) was added to a solution of 4,5-dimethoxy-2-2-(4-methylpiperazinyl)-2-oxoethyl]benzyl N-octadecylcarbamate (0.82 g) in ethyl acetate (24 ml) at room temperature. After being stirred for 30 minutes, the solvent was evaporated out. The residue was recrystallized from ethyl acetate-ethanol mixed solvent, thereby yielding 0.73 g of the aimed compound as white crystals.

$^1$H-NMR (CDCl$_3$) δ:0.88 (3H, t, J=6.8 Hz), 1.2–1.4 (30H, m), 1.48 (2H, m), 2.7–2.9 (2H, m), 2.79 (3H, s), 3.13 (2H, q, J=6.8 Hz), 3.3–3.6 (4H, m), 3.70 (1H, m), 3.86 (3H, s), 3.88 (3H, s), 4.01 (2H, m), 4.74 (1H, m), 4.89 (2H, m), 5.07 (1H, m), 6.68 (1H, s), 6.89 (1H, s), 13.17 (1H, brs).

| Compounding Example 1 Hair growth tonic | |
|---|---|
| Compound 12 | 0.5 wt % |
| Pyridoxine dioctanoate | 0.1 |
| Pantothenyl ethylether | 0.2 |

| -continued | |
|---|---|
| Compounding Example 1 Hair growth tonic | |
| Hinokitiol | 0.05 |
| Polyoxyethylene (12) polyoxypropylene (6) decyl tetradecyl | 1.0 |
| 1-Menthol | 0.1 |
| Disinfectants | Q.S. |
| 1,3-Butylene glycol | 3.0 |
| Ethanol | 70.0 |
| Purified water | Balance |

Preparation Method

Ethanol-soluble ingredients were added and dissolved into ethanol at room temperature while being stirred. Water-soluble ingredients were dissolved in purified water. The aqueous solution was added to the ethanol solution. After being uniformly mixed, the mixture was filtrated.

| Compounding Example 2 Hair regrowth promoting liquid lotion | |
|---|---|
| Compound 2 | 0.2 wt % |
| Carpronium chloride | 1.0 |
| Pantothenyl ethylether | 0.5 |
| Diphenhydramine hydrochloride | 0.1 |
| Hinokitiol | 0.1 |
| dl-α-tocopheryl acetate | 0.1 |
| Salicylic acid | 0.2 |
| 1-Menthol | 0.2 |
| Glycyrrhizinic acid | 0.1 |
| Sodium dl-pyrrolidonecarboxylate solution | 1.0 |
| Ethanol | 70.0 |
| Purified water | Balance |

Preparation Method

Ethanol-soluble ingredients were added and dissolved into ethanol at room temperature while being stirred. Water-soluble ingredients were dissolved in purified water. The aqueous solution was added to the ethanol solution. After being uniformly mixed, the mixture was filtrated.

| Compounding Example 3 Hair tonic | |
|---|---|
| Compound 14 | 0.1 wt % |
| Paeony root extract (1,3-butylene glycol extract) | 0.01 |
| Hinokitiol | 1.0 |
| Vitamin B$_6$ | 0.2 |
| Vitamin E acetate | 0.02 |
| Menthol | 0.2 |
| Swertia herb extract | 1.0 |
| Salicylic acid | 0.1 |
| Rosae rugosae flos extract (ethanol extract) | 0.5 |
| Propylene glycol | 2.0 |
| Sodium hyaluronate | 0.01 |
| Polyoxyethylene (10 mol) monostearate | 2.0 |
| 75% Ethanol | Balance |

Preparation Method

Each of the above ingredients was added and dissolved into 75% ethanol successively with stirring to obtain a hair tonic.

| Compounding Example 4 Hair tonic | |
|---|---|
| Paeonia extract (ethanol extract) | 5.0 wt % |
| Compound 12 | 0.05 |
| Compound 27 | 0.05 |

| Compounding Example 4 Hair tonic | |
| --- | --- |
| Hinokitiol | 1.0 |
| Vitamin B$_6$ | 0.2 |
| Vitamin E acetate | 0.02 |
| Menthol | 0.2 |
| Salicylic acid | 0.1 |
| Pueraria root extract (ethanol extract) | 0.5 |
| Propylene glycol | 2.0 |
| Sodium hyaluronate | 0.01 |
| Polyoxyethylene (10) monostearate | 2.0 |
| 75% Ethanol | Balance |

Preparation Method

Each of the above ingredients was added and dissolved into 75% ethanol successively with stirring to obtain a hair tonic.

| Compounding Example 5 Hair tonic | |
| --- | --- |
| Compound 31 | 0.05 wt % |
| 95% Ethanol | 50.0 |
| Monoammonium glycyrrhizinate | 0.05 |
| Paeonia extract (ethanol extract) | 0.05 |
| Paeony root extract (1,3-butylene glycol extract) | 0.02 |
| Saffron extract (ethanol extract) | 0.02 |
| Rosemary extract (ethanol extract) | 0.02 |
| Peppermint extract (ethanol extract) | 0.02 |
| Japanese angelica root extract (ethanol extract) | 0.02 |
| Althea extract (ethanol extract) | 0.02 |
| Rehmannia root extract (ethanol extract) | 0.02 |
| Coix extract (ethanol extract) | 0.02 |
| Sodium lauryl sulfate | 0.1 |
| N,N-dimethyl-2-decyltetradecylamineoxide | 0.5 |
| Polyoxyethylene (40) hydrogenated castor oil | 0.5 |
| Succinic acid | Q.S. |
| Perfume and coloring agent | Q.S. |
| Purified water | Balance |

Preparation Method

A hair tonic was prepared according to Compounding Example 1.

| Compounding Example 6 Hair lotion | |
| --- | --- |
| 95% Ethanol | 90.0 wt % |
| Vitamin E acetate | 0.05 |
| Compound 41 | 0.01 |
| Sodium lauryl sulfate | 0.06 |
| Propylene glycol | 0.1 |
| Polyoxyethylene (40) hydrogenated castor oil | 0.5 |
| Lactic acid | Q.S. |
| Sodium lactate | Q.S. |
| Perfume and coloring agent | Q.S. |
| Purified water | Balance |

Preparation Method

Polyoxyethylene (40) hydrogenated castor oil and perfume were dissolved in 95% ethanol. Then, purified water and the other ingredients were added and dissolved into the mixture successively with stirring to obtain a transparent liquid lotion.

| Compounding Example 7 Hair tonic | |
| --- | --- |
| Compound 4 | 0.1 wt % |
| Hinokitiol | 1.0 |
| Vitamin B$_6$ | 0.2 |
| Vitamin E acetate | 0.02 |
| Menthol | 0.2 |
| Swertia herb extract | 1.0 |
| Salicylic acid | 0.1 |
| Propylene glycol | 2.0 |
| Polyoxyethylene (10) monostearate | 2.0 |
| 75% Ethanol | Balance |

Preparation Method

Each of the above ingredients was added and dissolved into 75% ethanol successively with stirring to obtain a hair tonic.

| Compounding Example 8 Hair tonic | |
| --- | --- |
| Compound 6 | 0.5 wt % |
| Compound 12 | 0.1 |
| Hinokitiol | 1.0 |
| Vitamin B$_6$ | 0.2 |
| Vitamin E | 0.02 |
| Menthol | 0.2 |
| Salicylic acid | 0.1 |
| Propylene glycol | 2.0 |
| Sodium hyaluronate | 0.01 |
| Polyoxyethylene (10 mol) monostearate | 2.0 |
| 70% Ethanol | Balance |

Preparation Method

Each of the above ingredients was added and dissolved into 70% ethanol successively with stirring to obtain a hair tonic.

| Compounding Example 9 O/W type milky lotion | |
| --- | --- |
| (Phase A) | |
| Polyoxyethylene (60) hydrogenated castor oil | 2.0 wt % |
| Glycerin | 10.0 |
| Dipropylene glycol | 10.0 |
| 1,3-Butylene glycol | 4.0 |
| Compound 29 | 0.1 |
| Polyethylene glycol 1500 | 5.0 |
| (Phase B) | |
| Isocetyl octanoate | 10.0 |
| Squalane | 5.0 |
| Vaseline | 2.0 |
| Propyl paraben | 2.0 |
| (Phase C) | |
| 1% Carboxyvinylpolymer aqueous solution | 30.0 |
| Sodium hexametaphosphate | 0.03 |
| Ion-exchanged water | 8.35 |
| (Phase D) | |
| Ion-exchanged water | 4.5 |
| (Phase E) | |
| Potassium hydroxide | 0.12 |
| Ion-exchanged water | Balance |

Preparation Method

Phases A and B were heated and dissolved, separately. Both were mixed and treated with a homomixer, thereby obtaining a gel. Phase D was then gradually added to this gel and dispersed by the homomixer. Then, Phases C and E were added to this gel dispersion successively, which were mixed and dissolved in advance separately. The mixture was emulsified by the homomixer to obtain an O/W type milky lotion.

| Compounding Example 10 Cream | |
|---|---|
| (Phase A) | |
| N,N-Dimethyl-2-tetradecylamineoxide | 2.5 wt % |
| Liquid paraffin | 5.0 |
| Cetostearyl alcohol | 5.5 |
| Glyceryl monostealate | 3.0 |
| Polyoxyethylene (20) 2-octyldodecyl ether | 3.0 |
| Propyl paraben | 0.3 |
| Perfume | 0.1 |
| (Phase B) | |
| Compound 3 | 1.0 |
| Glycerin | 8.0 |
| Dipropylene glycol | 20.0 |
| Polyethylene glycol 4000 | 5.0 |
| Sodium hexametaphosphate | 0.005 |
| Ion-exchanged water | Balance |

Preparation Method

Phases A and B were heated and dissolved, separately. Both were mixed and emulsified by a homomixer to obtain a cream.

| Compounding Example 11 Aerosol spray | |
|---|---|
| (Stock solution) | |
| 95% Ethanol | 50.0 wt % |
| Glycyrrhizic acid | 0.1 |
| Compound 34 | 0.5 |
| Swertia herb extract | 0.1 |
| Sodium lauryl sulfate | 0.1 |
| Polyoxyethylene (40) hydrogenated castor oil | 0.5 |
| Lactic acid | Q.S. |
| Sodium lactate | Q.S. |
| Perfume | Q.S. |
| Ion-exchanged water | Balance |
| (Filling formulation) | |
| Stock solution | 50.0 |
| Liquefied petroleum gas | 50.0 |

Preparation Method

A stock solution was prepared by mixing and dissolving the ingredients of stock solution. This stock solution was filled into a can and a valve was fit thereto. Liquefied petroleum gas was filled into the can to obtain an aerosol spray.

| Compounding Example 12 Shampoo | |
|---|---|
| (1) Sodium cocoylmethyltaurate | 2.0 wt % |
| (2) Polyoxyethylene (8) oleyl ether | 2.0 |
| (3) Lauric acid diethanolamine | 4.0 |
| (4) Ethylene glycol fatty acid ester | 1.0 |
| (5) Glycerine | 0.2 |
| (6) Menthol | 0.1 |
| (7) Compound 35 | 0.1 |
| (8) Disodium edetate | 0.1 |
| (9) Perfume | Q.S. |
| (10) Purified water | Balance |

Preparation Method

The ingredient (10) was heated up to 70° C. The ingredients (1)–(9) were added to the heated ingredient (10) successively and the mixture was mixed and dissolved with stirring. The mixture was cooled to obtain a shampoo.

| Compounding Example 13 Rinse | |
|---|---|
| (1) Stearyl trimethyl ammonium chloride | 1.5 wt % |
| (2) Dimethyl polysiloxane(20 cs) | 3.0 |
| (3) Polyoxyethylene (10) oleyl ether | 1.0 |
| (4) Glycerine | 5.0 |
| (5) Compound 38 | 0.5 |
| (6) 4-tert-Butyl-4'-methoxydibenzoylmethane | Q.S. |
| (7) Ultraviolet absorber | Q.S. |
| (8) Purified water | Balance |

Preparation Method

The water phase was prepared by adding the ingredients (1), (3) and (4) to the ingredient (8) and heating up to 70° C. The oil phase was prepared by heating and dissolving the other ingredients up to 70° C. The oil phase was added to the water phase and the mixture was mixed with stirring by an emulsifier. The mixture was cooled to obtain a rinse.

| Compounding Example 14 Scalp treatment | |
|---|---|
| (Stock solution) | |
| (1) Liquid paraffin | 27.0 wt % |
| (2) Stearic acid | 5.0 |
| (3) Cetanol | 5.0 |
| (4) Sorbitan monooleate | 2.0 |
| (5) Polyoxyethylene sorbitan monooleate | 3.0 |
| (6) Compound 39 | 0.1 |
| (7) 1,3-Butylene glycol | 5.0 |
| (8) Antiseptic | Q.S. |
| (9) Purified water | Balance |
| (Filling formulation) | |
| Stock solution | 50.0 |
| Liquefied petroleum gas | 50.0 |

Preparation Method

The ingredients (5) and (6) were dissolved into ingredients (1) to (4). After being dissolved with heating up to 80° C., the mixture was cooled down. This mixture was added to the mixed solution of the ingredients (7) to (9), which was maintained at 30° C., and mixed with stirring to obtain a stock solution. This stock solution was filled into a can together with a propellant to obtain a scalp treatment.

| Compounding Example 15 Scalp treatment | |
|---|---|
| (Stock solution) | |
| (1) Hinokitiol | 0.1 wt % |
| (2) Swertia herb extract | 1.0 |
| (3) Vitamin $B_6$ | 0.1 |
| (4) Vitamin E | 0.01 |
| (5) Menthol | 0.1 |
| (6) Salicylic acid | 0.001 |
| (7) Compound 15 | 0.1 |
| (8) Polyoxyethylene sorbitan monooleate | 0.1 |
| (8) Propylene glycol | 2.0 |

-continued

| Compounding Example 15 Scalp treatment | |
|---|---|
| (10) 75% Ethanol (Filling formulation) | Balance |
| Stock solution | 50.0 |
| Dimethyl ether | 50.0 |

Preparation Method

A scalp treatment was prepared according to Compounding Example 14.

In the following, the compounds and manufacturing processes thereof in accordance with the present invention are exemplified.

Compound 46

[2-[[N-[3-(N-Methyl-N-phenylamino)propyl]carbamoyloxy]methyl]phenyl]-N-octadecylformamide

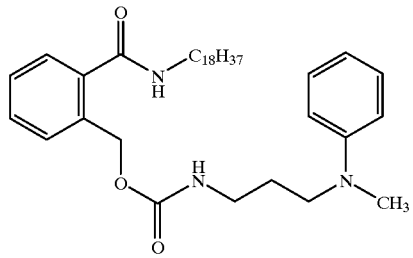

In Example 2, N-(3-aminopropyl)-N-methylaniline is used in place of N,N-dimethyl-1,3-propanediamine to obtain the aimed compound.

Compound 47

2-[[N-[3-(Dibenzylamino)propyl]carbamoyloxy]methyl]phenyl]-N-octadecylformamide

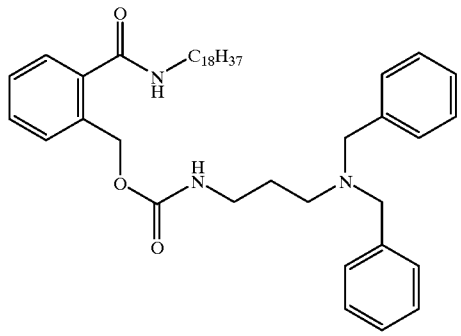

In Example 2, N,N-dibenzyl-1,3-propanediamine is used in place of N,N-dimethyl-1,3-propanediamine to obtain the aimed compound.

Compound 48

[4-Chloro-2-[[N-3-(dimethylamino)propyl]carbamoyloxy]methyl]phenyl]-N-octadecylformamide

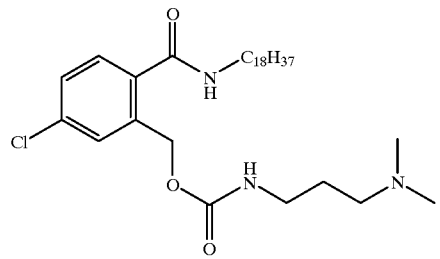

In Example 1-1, 5-chlorophthalide is used in place of phthalide to obtain [4-chloro-2-(hydroxymethyl)phenyl]-N-octadecylformamide.

In Example 2, this compound is used in place of [2-(hydroxymethyl)phenyl]-N-octadecylformamide to obtain the aimed compound.

Compound 49

[2-[[N-[3-(Dimethylamino)propyl]carbamoyloxy]methyl]-3-methylphenyl]-N-octadecylformamide

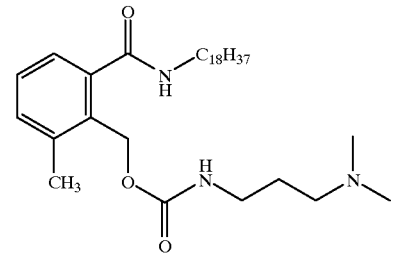

In Example 1-1, 4-methylphthalide is used in place of phthalide to obtain [2-(hydroxymethyl)-3-methylphenyl]-N-octadecylformamide.

In Example 2, this compound is used in place of [2-(hydroxymethyl)phenyl]-N-octadecylformamide to obtain the aimed compound.

Compound 50

[3-Acetyl-2-[[N-[3-(dimethylamino)propyl]carbamoyloxy]methyl]-5-methoxyphenyl]-N-octadecylformamide

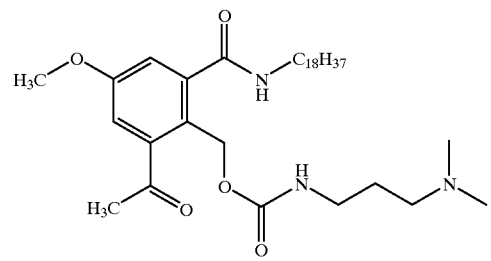

In Example 1-1, 4-acetyl-6-methoxyphthalide is used in place of phthalide to obtain [3-acetyl-2-(hydroxymethyl)-5-methoxylphenyl]-N-octadecylformamide.

In Example 2, this compound is used in place of [2-(hydroxymethyl)phenyl]-N-octadecylformamide to obtain the aimed compound.

Compound 51

[2-[[N-[4-(Dimethylamino)butyl]carbamoyloxy]methyl]-5-nitrophenyl]-N-octadecylformamide

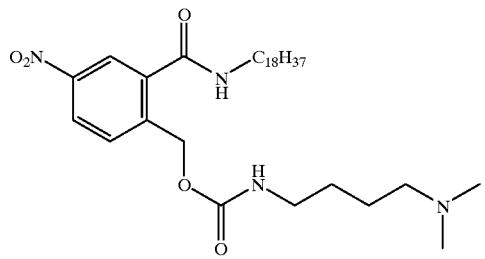

In Example 1-1, 6-nitrophthalide is used in place of phthalide to obtain [2-(hydroxymethyl)-5-nitrophenyl]-N-octadecylformamide.

In Example 2, this compound is used in place of (2-(hydroxymethyl)phenyl]-N-octadecylformamide and N,N,-dimethyl-1,4-butanediamine is used in place of N,N-dimethyl-1,3-propanediamine to obtain the aimed compound.

Compound 52
[5-Cyano-2-[[N-[5-(dimethylamino)pentyl]carbamoyloxy] methyl]phenyl]-N-octadecylformamide

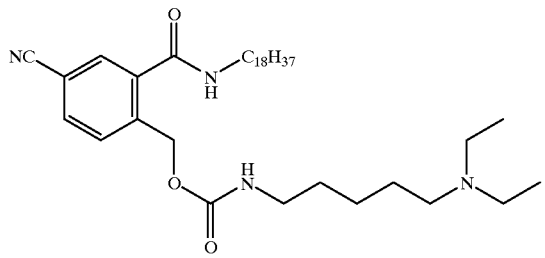

In Example 1-1, 6-cyanophthalide is used in place of phthalide to obtain [5-cyano-2-(hydroxymethyl)phenyl]-N-octadecylformamide.

In Example 2, this compound is used in place of [2-(hydroxymethyl)phenyl]-N-octadecylformamide and 5-diethylaminoamylamine is used in place of N,N-dimethyl-1,3-propanediamine to obtain the aimed compound.

Compound 53
[2-[[N-[3-(Dimethylamino)propyl]carbamoyloxy]methyl]-4-(methoxycarbonyl)phenyl]-N-octadecylformamide

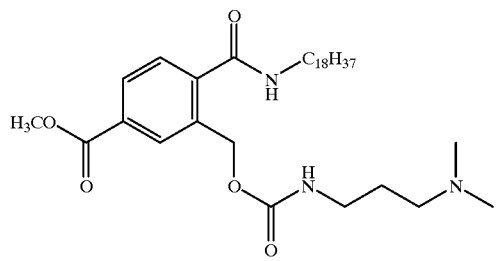

In Example 1-1, 5-(methoxycarbonyl)phthalide is used in place of phthalide to obtain [2-(hydroxymethyl)-4-(methoxycarbonyl)phenyl]-N-octadecylformamide.

In Example 2, this compound is used in place of 12-(hydroxymethyl)phenyl]-N-octadecylformamide to obtain the aimed compound.

Compound 54
[4-(Aminocarbonyl)-2-[[N-[3-(dimethylamino)propyl] carbamoyloxy]methyl]phenyl]-N-octadecylformamide

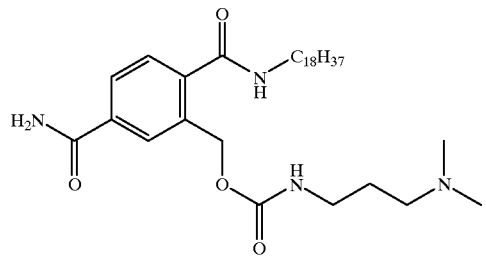

In Example 1-1, 5-(aminocarbonyl)phthalide is used in place of phthalide to obtain [4-(aminocarbonyl)-2-(hydroxymethyl)phenyl]-N-octadecylformamide.

In Example 2, this compound is used in place of [2-(hydroxymethyl)phenyl]-N-octadecylformamide to obtain the aimed compound.

Compound 55
[2-[[N-[3-(Dimethylamino)propyl]carbamoyloxy]methyl]-4-(N-methylcarbamoyl)phenyl]-N-octadecylformamide

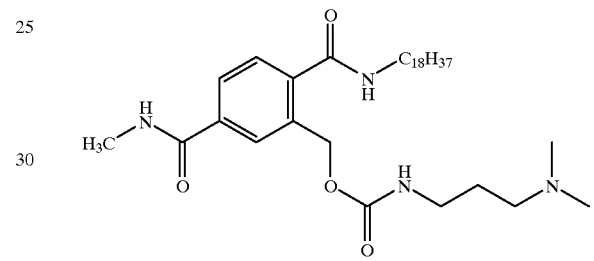

In Example 1-1, 5-(N-methylcarbamoyl)phthalide is used in place of phthalide to obtain [2-(hydroxymethyl)-4-(N-methylcarbamoyl)phenyl]-N-octadecylformamide.

In Example 2, this compound is used in place of [2-(hydroxymethyl)phenyl]-N-octadecylformamide to obtain the aimed compound.

Compound 56
[2-[[N-[3-(Dimethylamino)propyl]carbamoyloxy]methyl]-5-(dimethylamino)phenyl]-N-octadecylformamide

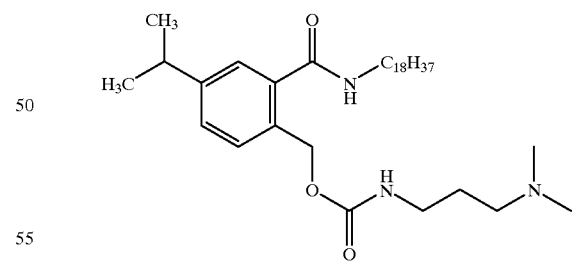

In Example 1-1, 6-(dimethylamino)phthalide is used in place of phthalide to obtain [2-(hydroxymethyl)-5-(dimethylamino)phenyl]-N-octadecylformamide.

In Example 2, this compound is used in place of [2-(hydroxymethyl)phenyl]-N-octadecylformamide to obtain the aimed compound.

Compound 57
[5-(Benzoylamino)-2-[[N-[3-(dimethylamino)propyl] carbamoyloxy]methyl]phenyl]-N-octadecylformamide

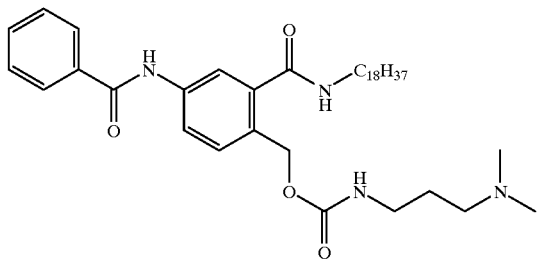

In Example 1-1, 6-(benzoylamino)phthalide is used in place of phthalide to obtain [5-(benzoylamino)-2-(hydroxymethyl)phenyl]-N-octadecylformamide.

In Example 2, this compound is used in place of [2-(hydroxymethyl)phenyl]-N-octadecylformamide to obtain the aimed compound.

Compound 58
[2-[[N-[3-(Dimethylamino)propyl]carbamoyloxy]methyl]-5-methoxyphenyl]-N-octadecylformamide

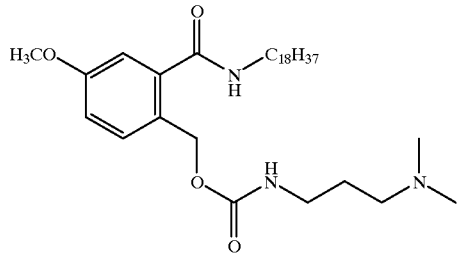

In Example 1-1, 6-methoxyphthalide is used in place of phthalide to obtain [2-(hydroxymethyl)-5-methoxyphenyl]-N-octadecylformamide.

In Example 2, this compound is used in place of [2-(hydroxymethyl)phenyl]-N-octadecylformamide to obtain the aimed compound.

Compound 59
[3-(Acetoxy)-2-[[N-[3-(dimethylamino)propyl]carbamoyloxy]methyl]phenyl]-N-octadecylformamide

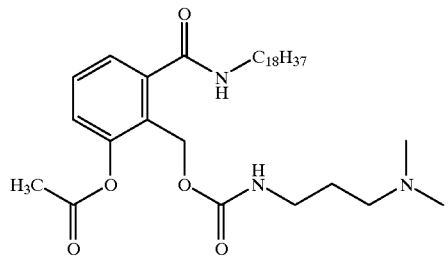

In Example 1-1, 4-(acetoxy)phthalide is used in place of phthalide to obtain [3-(acetoxy)-2-(hydroxymethyl)phenyl]-N-octadecylformamide.

In Example 2, this compound is used in place of [2-(hydroxymethyl)phenyl]-N-octadecylformamide to obtain the aimed compound.

Compound 60
[2-[[N-[3-(Dimethylamino)propyl]carbamoyloxy]methyl]phenyl]-N-methyl-N-octadecylformamide

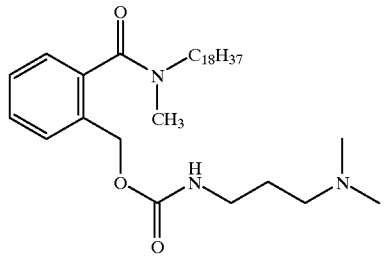

In Example 1-1, N-methyl-N-octadecylamine is used in place of octadecylamine to obtain [2-(hydroxymethyl)phenyl]-N-methyl-N-octadecylformamide.

In Example 2, this compound is used in place of [2-(hydroxymethyl)phenyl]-N-octadecylformamide to obtain the aimed compound.

Compound 61
N-Acetyl-[2-[[N-acetyl-N-[3-(dimethylamino)propyl]carbamoyloxy]methyl]phenyl]-N-octadecylformamide

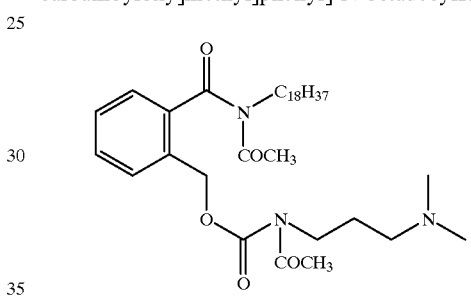

[2-[[N-[3-(Dimethylamino)propyl]carbamoyloxy]methyl]phenyl]-N-octadecylformamide synthesized in Example 2 is acetylated to obtain the aimed compound.

Compound 62
[2-[[N-[3-(Dimethylamino)propyl]-N-(methylcarbamoyl)carbamoyloxy]methyl]phenyl]-N-(methylcarbamoyl)-N-octadecylformamide

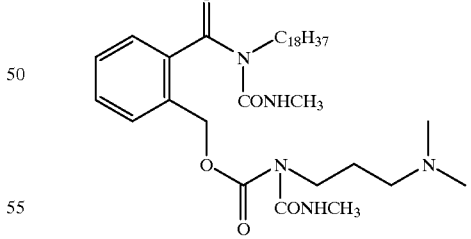

[2-[[N-[3-(Dimethylamino)propyl]carbamoyloxy]methyl]phenyl]-N-octadecylformamide synthesized in Example 2 is methylcarbamoylated to obtain the aimed compound.

Compound 63
[2-[[N-[3-(Dimethylamino)propyl]-N-methylcarbamoyloxy]methyl]phenyl]-N-methyl-N-octadecylformamide

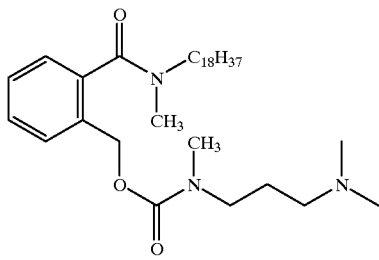

In Example 1-1, N-methyl-N-octadecylamine is used in place of octadecylamine to obtain [2-(hydroxymethyl)phenyl]-N-methyl-N-octadecylformamide.

In Example 2, this compound is used in place of [2-(hydroxymethyl)phenyl]-N-octadecylformamide and N,N,N'-trimethyl-1,3-propanediamine is used in place of N,N-dimethyl-1,3-propanediamine to obtain the aimed compound.

Compound 64
[2-[[N-[2-(N-Ethyl-N-butylamino)ethyl]carbamoyloxy]methyl]phenyl]-N-octadecylformamide

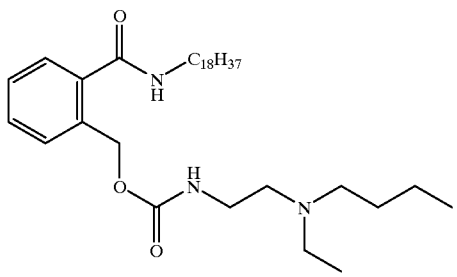

In Example 2, N-ethyl-N-butylethylenediamine is used in place of N,N-dimethyl-1,3-propanediamnine to obtain the aimed compound.

Compound 65
{2-[4-(Dimethylamino)butoxymethyl]phenyl}-N-methyl-N-octadecylformamide

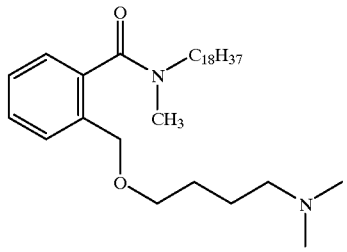

[2-(Hydroxymethyl)phenyl]-N-methyl-N-octadecylformamide is reacted with 1-bromo-4-chlorobutane in acetone in the presence of potassium carbonate at the reflux temperature of the solvent to obtain [2-(4-chlorobutoxymethyl)phenyl]-N-methyl-N-octadecylformamide.

This compound is reacted with dimethylamine in acetone in the presence of potassium carbonate at the reflux temperature of the solvent to obtain the aimed compound.

Compound 66
{2-[4-(Morpholino)butoxymethyl]phenyl}-N-methyl-N-octadecylformamide

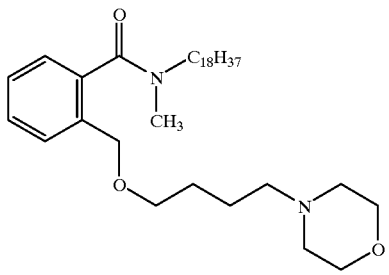

[2-(Hydroxymethyl)phenyl]-N-methyl-N-octadecylformamide is reacted with 1-bromo-4-chlorobutane in acetone in the presence of potassium carbonate at the reflux temperature of the solvent to obtain [2-(4-chlorobutoxymethyl)phenyl]-N-methyl-N-octadecylformamide.

This compound is reacted with morpholine in acetone in the presence of potassium carbonate at the reflux temperature of the solvent to obtain the aimed compound.

Compound 67
[2-[[3-(Dimethylamino)propyl]carbonyloxymethyl]phenyl]-N-octadecylformamide

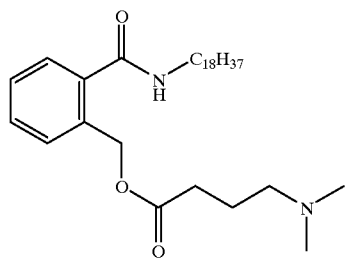

DCC is added to a solution of [2-(hydroxymethyl)phenyl]-N-octadecylformamide and 4-(N,N-dimethylamino)butyric acid in N,N-dimethylformamide and then the reaction is effected at room temperature to obtain the aimed compound.

Compound 68
[2-[[N-[3-(Dimethylamino)propyl]amino]methyl]phenyl]-N-methyl-N-octadecylformamide

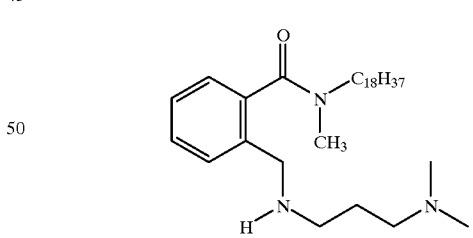

A solution of [2-(hydroxymethyl)phenyl]-N-methyl-N-octadecylformamide and p-toluenesulfonyl chloride in 1,4-dioxane is added to sodium hydroxide solution and the reaction is effected at room temperature to obtain [2-(tosyloxymethyl)phenyl]-N-methyl-N-octadecylformamide.

This compound is reacted with N,N-dimethyl-1,3-propanediamine in acetone in the presence of potassium carbonate at the reflux temperature of the solvent to obtain the aimed compound.

Compound 69
[2-[[N-[3-(Piperidino)propyl]-amino]methyl]phenyl]-N-methyl-N-octadecylformamide

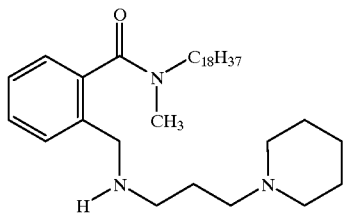

A solution of [2-(hydroxymethyl)phenyl]-N-methyl-N-octadecylformamide and p-toluenesulfonyl chloride in 1,4-dioxane is added to sodium hydroxide solution and the reaction is effected at room temperature to obtain [2-(tosyloxymethyl)phenyl]-N-methyl-N-octadecylformamide.

This compound is reacted with 1-(3-aminopropyl) piperidine in acetone in the presence of potassium carbonate at the reflux temperature of the solvent to obtain the aimed compound.
Compound 70
N-Dodecyl-[2-[[N-[3-(morpholino)propyl]amino]methyl]phenyl]-N-methylformamide

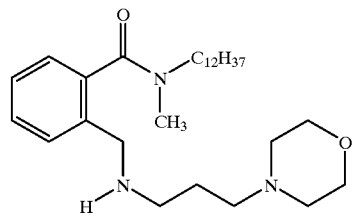

In Example 8, N-methyl-N-dodecylamine is used in place of dodecylamine to obtain N-dodecyl-[1 2-(hydroxymethyl)phenyl]-N-methylformamide.

A solution of this compound and p-toluenesulfonyl chloride in 1,4-dioxane is added to sodium hydroxide solution and the reaction is effected at room temperature to obtain N-dodecyl-[2-(tosyloxymethyl)phenyl]-N-methylformamide.

This compound is reacted with 1-(3-aminopropyl) morpholine in acetone in the presence of potassium carbonate at the reflux temperature of the solvent to obtain the aimed compound.
Compound 71
N-[3-(Dimethylamino)propyl]-{2-[(N-dodecylcarbamoyloxy)methyl]phenyl}formamide

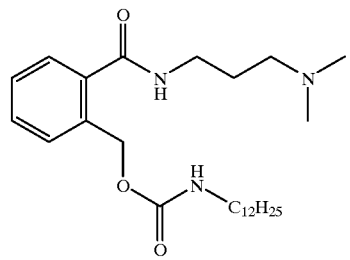

In Example 22 (2), dodecyl isocyanate is used in place of octadecyl isocyanate to obtain the aimed compound.
Compound 72
N-[3-(4-Methylpiperazinyl)propyl]-{2-[(N-octadecylcarbamoyloxy)methyl]phenyl}formamide

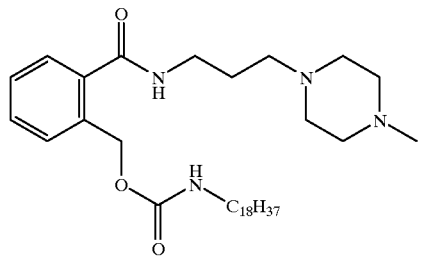

In Example 22 (1), 1-(3-aminopropyl)-4-methylpiperazine is used in place of N,N-dimethyl-1,3-propanediamine to obtain N-[3-(4-methylpiperazinyl)propyl]-[2-(hydroxymethyl)phenyl]formamide.

In the similar manner to Example 22 (2), this compound is reacted with octadecyl isocyanate to obtain the aimed compound.

Compound 73

N-[3-(Dimethylamino)propyl]-[2-(octadecyloxymethyl)phenyl]formamide

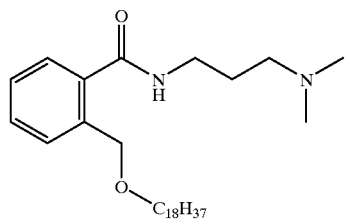

N-[3-(Dimethylamino)propyl]-[2-(hydroxymethyl)phenyl]formamide is reacted with 1-bromooctadecane in acetone in the presence of potassium carbonate at the reflux temperature of the solvent to obtain the aimed compound.

Compound 74

[2-[N-[3-(Dimethylamino)propyl]carbamoyl]phenyl]methyl octadecanoate

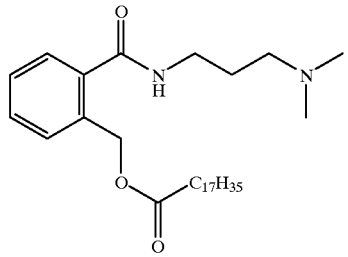

DCC is added to a solution of N-[3-(dimethylamino)propyl]-[2-(hydroxymethyl)phenyl]formamide and stearic acid in N,N-dimethylformamide and then the reaction is effected at room temperature to obtain the aimed compound.

Compound 75

N-[3-(Dimethylamino)propyl]-N-methyl-{[2-(octadecylamino)methyl]phenyl}formamide

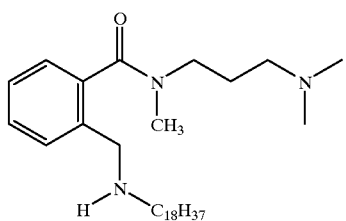

In Example 22 (1), N,N,N'-trimethyl-1,3-propanediamine is used in place of N,N-dimethyl-1,3-propanediamine to obtain N-[3-(dimethylamino)propyl]-N-methyl-[2-(hydroxymethyl)phenyl]formamide.

A solution of this compound and p-toluenesulfonyl chloride in 1,4-dioxane is added to sodium hydroxide solution and the mixture is reacted at room temperature to obtain N-[3-(dimethylamino)propyl]-N-methyl-[2-(tosyloxymethyl)phenyl]formamide.

This compound is reacted with octadecylamine in acetone in the presence of potassium carbonate at the reflux temperature of the solvent to obtain the aimed compound.
Compound 76
N-Methyl-[3-(morpholino)propyl]-{2-[(octadecylamino)methyl]phenyl}formamide

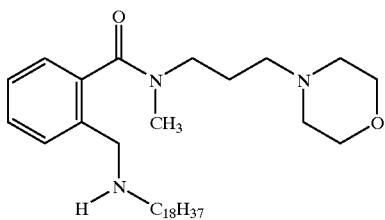

In Example 22 (1), 4-[3-(methylamino)propyl]morpholine is used in place of N,N-dimethyl-1,3-propaneamine to obtain N-methyl-N-[3-(morpholino)propyl]-[2-(hydroxymethyl)phenyl]formamide.

A solution of this compound and p-toluenesulfonyl chloride in 1,4-dioxane is added to sodium hydroxide solution and the reaction is effected at room temperature to obtain N-methyl-N-[3-(morpholino)propyl]-[2-(tosyloxymethyl)phenyl]formamide.

This compound is reacted with octadecylamine in acetone in the presence of potassium carbonate at the reflux temperature of the solvent to obtain the aimed compound.

What is claimed is:

1. A 1,2-di-substituted benzene-carboxamide derivative or a salt thereof expressed by the following Formula (I):

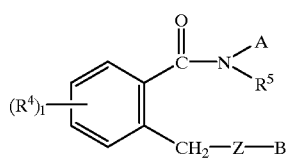

wherein
each of A and B is $R^1$ or —$(CH_2)n$-$NR^2R^3$, wherein when A is $R^1$, B is —$(CH_2)n$-$NR^2R^3$ and when A is —$(CH_2)n$-$NR^2R^3$, B is $R^1$;
Z is —O—, —OCO—, —OCONR$^6$— or —NR$^6$—;
$R^1$ is a hydrocarbon group of $C_{10-30}$;

$R^2$ and $R^3$ individually represent a hydrogen atom, a lower alkyl group, a phenyl group or a benzyl group, or together represent a heterocyclic ring having 3–7 members;

when A is —$(CH_2)n$-$NR^2R^3$, $R^2$ may be a hydrogen atom, a lower alkyl group, a phenyl group or a benzyl group, and $R^3$ and $R^5$ together may represent a heterocyclic ring of 6 or 7 members including two nitrogen atoms;

when —Z—B is —OCONR$^6$—$(CH_2)n$-$NR^2R^3$ or —NR$^6$—$(CH_2)n$-$NR^2R^3$, $R^2$ may be a hydrogen atom, a lower alkyl group, a phenyl group or a benzyl group, and $R^3$ and $R^6$ together may represent a heterocyclic ring of 6 or 7 members including two nitrogen atoms;

$R^4$ is selected from the group consisting of a halogen atom, a lower alkyl group, a lower acyl group, a nitro group, a cyano group, a lower alkoxycarbonyl group, a carbamoyl group, a lower alkylcarbamoyl group, a lower alkylamino group, a lower acylamino group, a lower alkoxy group and a lower acyloxy group;

$R^5$ is a hydrogen atom, a lower alkyl group, a lower acyl group or a lower alkylcarbamoyl group, or when A is —$(CH_2)n$-$NR^2R^3$, $R^5$ and $R^3$ together may represent a heterocyclic ring of 6 or 7 members including two nitrogen atoms;

$R^6$ is a hydrogen atom, a lower alkyl group, a lower acyl group or a lower alkylcarbamoyl group, or when —Z—B is —OCONR$^6$—$(CH_2)n$-$NR^2R^3$ or —NR$^6$—$(CH_2)n$-$NR^2R^3$, $R^6$ and $R^3$ together may represent a heterocyclic ring of 6 or 7 members including two nitrogen atoms;

l is an integer of 0–2; and n is an integer of 0–5.

2. A 1,2-di-substituted benzene-carboxamide derivative or a salt thereof according to claim 1, wherein A is $R^1$ and B is —$(CH_2)n$-$NR^2R^3$.

3. A 1,2-di-substituted benzene-carboxamide derivative or a salt thereof according to claim 2, wherein Z is —OCONR$^6$—, wherein $R^6$ is a hydrogen atom, a lower alkyl group, a lower acyl group or a lower alkylcarbamoyl group.

4. A 1,2-di-substituted benzene-carboxamide derivative or a salt thereof according to claim 3, wherein $R^6$ is a hydrogen atom.

5. A 1,2-di-substituted benzene-carboxamide derivative or a salt thereof according to claim 2, wherein n is an integer of 2–5.

6. A 1,2-di-substituted benzene-carboxamide derivative or a salt thereof according to claim 2, which is expressed by the following Formula (IA) or (IB):

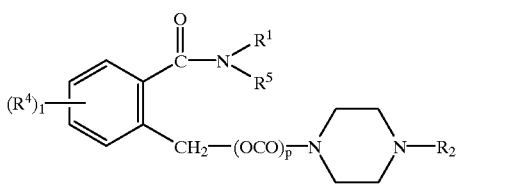

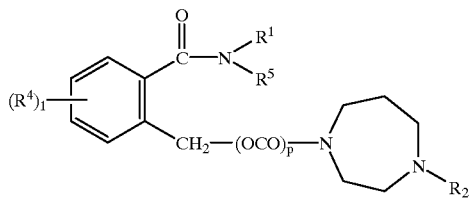

(IB)

wherein
$R^1$ is a hydrocarbon group of $C_{10-30}$;
$R^2$ is a hydrogen atom, a lower alkyl group, a phenyl group or a benzyl group;
$R^4$ is selected from the group consisting of a halogen atom, a lower alkyl group, a lower acyl group, a nitro group, a cyano group, a lower alkoxycarbonyl group, a carbamoyl group, a lower alkylcarbamoyl group, a lower alkylamino group, a lower acylamino group, a lower alkoxy group and a lower acyloxy group;
$R^5$ is a hydrogen atom a lower alkyl group, a lower acyl group or a lower alkylcarbamoyl group;
l is an integer of 0–2; and
p is 0 or 1.

7. A 1,2-di-substituted benzene-carboxamide derivative or a salt thereof according to claim 2, wherein $R^5$ is a hydrogen atom.

8. A 1,2-di-substituted benzene-carboxamide derivative or a salt thereof according to claim 1, wherein A is —($CH_2$)n-$NR^2R^3$ and B is $R^1$.

9. A 1,2-di-substituted benzene-carboxamide derivative or a salt thereof according to claim 8, wherein $R^5$ is a hydrogen atom.

10. A 1,2-di-substituted benzene-carboxamide derivative or a salt thereof according to claim 8, wherein n is an integer of 2–5.

11. A 1,2-di-substituted benzene-carboxamide derivative or a salt thereof according to claim 8, which is expressed by the following Formula (IC) or (ID):

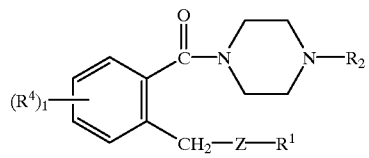

(IC)

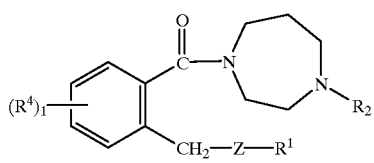

(ID)

wherein
$R^1$ is a hydrocarbon group of $C_{10-30}$;
$R^2$ is a hydrogen atom, a lower alkyl group, a phenyl group or a benzyl group;
$R^4$ is selected from the group consisting of a halogen atom, a lower alkyl group, a lower acyl group, a nitro group, a cyano group, a lower alkoxycarbonyl group, a carbamoyl group, a lower alkylcarbamoyl group, a lower alkylamino group, a lower acylamino group, a lower alkoxy group and a lower acyloxy group;
Z is —O—, —OCO—, —OCONR$^6$— or —NR$^6$—, wherein $R^6$ is a hydrogen atom, a lower alkyl group, a lower acyl group or a lower alkylcarbamoyl group; and
l is an integer of 0–2.

12. A 1,2-di-substituted benzene-carboxamide derivative or a salt thereof according to claim 8, wherein Z is —OCONR$^6$—.

13. A 1,2-di-substituted benzene-carboxamide derivative or a salt thereof according to claim 12, wherein $R^6$ is a hydrogen atom.

14. A 1,2-di-substituted benzene-carboxamide derivative or a salt thereof according to claim 1, wherein $R^1$ is an alkyl group of $C_{10-30}$.

15. A 1,2-di-substituted benzene-carboxamide derivative or a salt thereof according to claim 1, wherein l is 0.

16. A hair growth promoting composition comprising an effective amount of the 1,2-di-substituted benzene-carboxamide derivative or the pharmacologically acceptable salt thereof according to claim 1 and a carrier.

17. An external preparation for skin comprising the 1,2-di-substituted benzene-carboxamide derivative or the pharmacologically acceptable salt thereof according to claim 1 and a carrier.

18. A method for promoting hair growth, which comprises applying an effective amount of the 1,2-di-substituted benzene-carboxamide derivative or the pharmacologically acceptable salt thereof according to claim 1 on skin of mammals.

19. A method for promoting hair growth according to claim 18, wherein the skin of mammals is human scalp.

* * * * *